(12) United States Patent
Shah et al.

(10) Patent No.: US 6,855,809 B2
(45) Date of Patent: Feb. 15, 2005

(54) METHODS FOR THE SIMULTANEOUS DETECTION OF HCV ANTIGENS AND HCV ANTIBODIES

(75) Inventors: Dinesh O. Shah, Libertyville, IL (US); George J. Dawson, Libertyville, IL (US); A. Scott Muerhoff, Kenosha, WI (US); Lily Jiang, Mundelein, IL (US); Robin A. Gutierrez, Gurnee, IL (US); Thomas P. Leary, Kenosha, WI (US); Suresh Desai, Libertyville, IL (US); James L. Stewart, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/753,910

(22) Filed: Jan. 7, 2004

(65) Prior Publication Data

US 2004/0185436 A1 Sep. 23, 2004

Related U.S. Application Data

(60) Division of application No. 10/173,480, filed on Jun. 17, 2002, now Pat. No. 6,727,092, which is a continuation-in-part of application No. 09/891,983, filed on Jun. 26, 2001.

(51) Int. Cl.[7] .................. C07K 14/00; C07K 14/08; C07H 21/00; A61K 39/00; C12N 15/62
(52) U.S. Cl. ............... 530/350; 424/184.1; 424/189.1; 424/192.1; 424/204.1; 536/23.4; 536/23.72; 435/7.1; 435/7.92; 435/69.1; 435/325; 435/320.1
(58) Field of Search .................. 435/4, 5, 7.1, 7.6, 435/7.9, 7.92, 69.1, 69.3, 69.7, 70.1, 71.1, 455, 325, 320.1; 424/130.1, 139.1, 141.1, 147.1, 149.1, 184.1, 185.1, 189.1, 192.1, 204.1, 228.1; 530/300, 350, 388.1, 388.3, 402, 403; 536/23.1, 23.4, 23.7, 23.72

(56) References Cited

U.S. PATENT DOCUMENTS

| 5,322,769 A | 6/1994 | Bolling et al. |
| 5,443,965 A | 8/1995 | Reyes et al. |
| 5,627,026 A | 5/1997 | O'Connor et al. |
| 5,705,330 A | 1/1998 | Shah et al. |
| 5,753,430 A | 5/1998 | Mehta et al. |
| 6,172,189 B1 | 1/2001 | Devare et al. |
| 6,312,889 B1 | 11/2001 | Houghton et al. |
| 6,383,740 B2 | 5/2002 | Collins |

FOREIGN PATENT DOCUMENTS

| GB | 2313666 | * | 1/1981 |
| GB | 2051357 | * | 3/1997 |
| WO | 97/01758 | | 1/1997 |
| WO | 01/96875 A2 | | 12/1997 |
| WO | 99/06836 | | 11/1999 |

OTHER PUBLICATIONS

Chien et al., Clinical Microbiology, vol. 37 No 5, pp. 1393–1397 (May 1999).*
Frank Quinn, *The Immunoassay Handbook, Second Edition*, pp. 363–367 (2001).
G. Reyes, et al., *Mol. Cell. Probes*, 5:473:481 (1991).
Kashiwakuma, et al., Detection of hepatitic C virus specific core protein in serum of patients by a sensitive fluorescence enzyme immunoassay (FEIA), *Journ of Immun Methods*, 190:79–89 (1996).
Dawson, G.J. et al "Detection of Exposure to *Hepatitis C* Virus Utilizing a Prototype HCV Antigen Test" *Transfusion*, vol. 40, No. 10S (Oct. 2000) p. 83S.
Masalova, O.V. et al. "Detection of *Hepatitis C* Virus Core Protein Circulating Within Different Virus Particle Populations" *Journal of Medical Virology*, vol. 55 (1998) pp. 1–6.
Jolivet–Reynaud, C et al., "HCV Core Immunodominant Region Analysis Using Mouse Monoclonal Antibodies and Human Sera: Characterization of Major Epitopes Useful for Antigen Detection" *Journal of Medical Virology*, vol. 56 (1998) pp. 300–309.
Major, et al., *Hepatology*, 25:1527 (1997).
Muerhoff A.S., et al., *J. Virol*, 69;5621 (1995).
Choo, et al., *Proc. Natl. Acad. Sci. USA*, 88:2451 (1991).
Grakoui, et al., *J. Virol*, 67:1385 (1993.
Busch, et al., *Transfusion*, 40:143 (2000).
Choo, et al., *Science*, 244:359 (1989).
Kuo, et al., *Science*, 244:362 (1989).
Mimms, et al., *Lancet*, 336:1590 (1990).
Bresters, et al., *Vox Sang*, 62:213 (1992).
Kleinman, et al., *Transfusion*, 32:805 (1992).
Hino K., *Intervirology*, 37:77 (1994).
Alter, et al., *N. Engl. J. Med.*, 327:1899 (1992).
Lee, et al., *Transfusion*, 35:845 (*1995*).
Courouce, et al., *Transfusion*, 34:790–795 (1994).
Courouce, et al., *Lancet*, 343:853 (1994).
Aoyagi, et al., *J. Clin Microbiol.*, 37:1802 (1999).
Peterson, et al., *Vox Sang*, 78:80 (2000).
Dawson, et al., *Transfusion*, SD161, 40 (2000).
Tanaka, et al., *Hepatology*, 32:388 (2000).
Tanaka, et al., *J. Hepatology*, 23:742 (1995).
Kohler and Milstein, *Nature*, 256:494 (1975).

* cited by examiner

*Primary Examiner*—James Housel
*Assistant Examiner*—Zachariah Lucas
(74) *Attorney, Agent, or Firm*—Cheryl L. Becker

(57) ABSTRACT

The subject invention relates to methods for the simultaneous detection of Hepatitis C Virus (HCV) antigens as well as antibodies produced in response to HCV antigens. Furthermore, the subject invention allows one to detect antigens in the early, acute stage of infection, even prior to the development of antibodies, thereby allowing for early detection of infected blood and blood products, thus improving the safety of the blood supply.

4 Claims, 14 Drawing Sheets

A PROTOTYPE ABBOTT PRISM* HCV Ag/Ab COMBO
ASSAY FORMAT

STEP: 1

STEP: 2

- ANTI-HCV CORE MONOCLONAL ANTIBODIES MICROPARTICLES
- γ-Ag AND PEPTIDE-COATED MICROPARTICLES
- HCV CORE ANTIGEN
- HCV Ab ANTIBODY
- AC* ACRIDINYLATED ANTI-HCV CORE MONOCLONAL ANTIBODIES
- AC* ACRIDINIUM LABELED MOUSE ANTI-HUMAN IgG (mouse MAb)

SD  SPECIMEN DILUENT

SEQ ID NO:1

5'HO- ata gaa ttc cat gca gaa aaa aaa caa acg taa cac caa c -3'OH

SEQ ID NO:2

5'HO- cgg ctg aga acg ttc aga ggt ttt aac gat ctg acc acc acc cgg g -3'OH

SEQ ID NO:3

5'HO- aaa acc tct gaa cgt tct cag ccg -3'OH

SEQ ID NO:4

5'HO- tat gga tcc tta tta cgg aga cag cag cca acc agc -3'OH

SEQ ID NO:5

```
  1  GAATTCCATG CAGAAAAAAA ACAAACGTAA CACCAACCGT CGTCCGCAGG
 51  ACGTTAAATT CCCGGGTGGT GGTCAGATCG TTAAAACCTC TGAACGTTCT
101  CAGCCGCGTG GCGTCGTCA GCCGATCCCG AAAGCTCGTC GTCCGGAAGG
151  TCGTACCTGG GCTCAGCCGG GTTACCCGTG GCCGCTGTAC GGTAACGAAG
201  GTTGCGGTTG GCAGGTTGG CTGCTGTCTC CGTAATAAGG ATCC
```

SEQ ID NO:6

```
  1  MQKKNKRNTN RRPQDVKFPG GGQIVKTSER SQPRGRRQPI PKARRPEGRT
 51  WAQPGYPWPL YGNEGCGWAG WLLSP**
```

SEQ ID NO:7

```
  1  GAATTCCATG CAGAAAAAAA ACAAACGTAA CACCAACCGT CGTCCGCAGG
```

FIG.4A

```
 51  ACGTTAAATT CCCGGGTGGT GGTCAGATCG TTGGTCTGCT GCCGCGTCGT
101  GGTCCGCGTC TGGGTCGTAA AACCTCTGAA CGTTCTCAGC CGCGTGGGCG
151  TCGTCAGCCG ATCCCGAAAG CTCGTCGTCC GGAAGGTCGT ACCTGGGCTC
201  AGCCGGGTTA CCCGTGGCCG CTGTACGGTA ACGAAGGTTG CGGTTGGGCT
251  GGTTGGCTGC TGTCTCCGTA ATAAGGATCC
```

SEQ ID NO:8

```
  1  MQKKNKRNTN RRPQDVKFPG GGQIVGLLPR RGPRLGRKTS ERSQPRGRRQ
 51  PIPKARRPEG RTWAQPGYPW PLYGNEGCGW AGWLLSP**
```

SEQ ID NO:9

5'HO- acc cag acg cgg acc acg acg cgg cag cag acc aac gat ctg acc acc acc c -3'OH

SEQ ID NO:10

5'HO- ccg cgt cgt ggt ccg cgt ctg ggt cgt aaa acc tct gaa cgt tct cag -3'OH

SEQ ID NO:11

```
  1  GAATTCCATG CAGAAAAAAA ACAAACGTAA CACCAACCGT CGTCCGCAGG
 51  ACGTTAAATT CCCGGGTGGT GGTCAGATCG TTGGTGGTGT TACGTTCTG
101  CCGCGTCGTG GTCCGCGTCT GGGTGTTCTG GCTACGCGTA AAACCTCTGA
151  ACGTTCTCAG CCGCGTGGGC GTCGTCAGCC GATCCCGAAA GCTCGTCGTC
201  CGGAAGGTCG TACCTGGGCT CAGCCGGGTT ACCCGTGGCC GCTGTACGGT
251  AACGAAGGTT GCGGTTGGGC TGGTTGGCTG CTGTCTCCGT AATAAGGATC
301  C
```

FIG.4B

SEQ ID NO:12

1  MQKKNKRNTN RRPQDVKFPG GGQIVGGVYV LPRRGPRLGV LATRKTSERS

51 QPRGRRQPIP KARRPEGRTW AQPGYPWPLY GNEGCGWAGW LLSP**

SEQ ID NO:13

5'HO- acc cag acg cgg acc acg acg cgg cag aac gta aac acc acc aac -3'OH

SEQ ID NO:14

5'HO- ccg cgt cgt ggt ccg cgt ctg ggt gtt ctg gct acg cgt aaa acc -3'OH

SEQ ID NO:15

1   GAATTCCATG CAGAAAAAAA ACAAACGTAA CACCAACCGT CGTCCGCAGG

51  ACGTTAAATT CCCGGGTGGT GGTCAGATCG TTGGTGGTGT TTACCTGCTN

101 CCGCGTCGTG GTCCGCGTCT GGGTGTTCGT GCTACGCGTA AAACCTCTGA

151 ACGTTCTCAG CCGCGTGGGC GTCGTCAGCC GATCCGAAAG CTCGTCGTCC

201 GGAAGGTCGT ACCTGGGCTC AGCCGGGTTA CCCGTGGCCG CTGTACGGTA

251 ACGAAGGTTG CGGTTGGGCT GGTTGGCTGC TGTCTCCGTA ATAAGGATCC

SEQ ID NO:16

1  MQKKNKRNTN RRPQDVKFPG GGQIVGGVYL LPRRGPRLGV RATRKTSERS

51 QPRGRRQPIP KARRPEGRTW AQPGYPWPLY GNEGCGWAGW LLSP**

SEQ ID NO:17

1   GAATTCCATG GCTGTTGACT TTATCCCGGT TGAAAATCTC GAGACTACTA

51  TGCGTTCTCC GGTTTTCACT GACAACTCTT CTCCGCCGGT TGTTCCGCAG

101 TCTTTCCAGG TTGCTCACCT GCATGCTCCG ACTGGTTCTG GTAAATCTAC

151 TAAAGTTCCA GCTGCTTACG CTGCTCAGGG TTACAAAGTT CTGGTTCTGA

201 ACCCGTCTGT TGCTGCTACT CTGGGTTTCG GCGCCTACAT GTCTAAAGCT

FIG.4C

```
251  CACGGTATCG ACCCGAACAT TCGTACTGGT GTACGTACTA TCACTACTGG
301  TTCTCCGATC ACTTACTCTA CTTACGGTAA ATTCCTGGCT GACGGTGGTT
351  GCTCTGGTGG TGCTTACGAT ATCATCATCT GCGACGAATG CCACTCTACT
401  GACGCTACTT CTATCCTGGG TATCGGTACC GTTCTGGACC AGGCTGAAAC
451  TGCAGGTGCT CGTCTGGTTG TTCTGGCTAC TGCTACTCCG CCGGGTTCTG
501  TTACTGTTCC GCACCCGAAC ATCGAAGAAG TTGCTCTGTC GACTACTGGT
551  GAAATCCCGT TCTACGGTAA AGCTATCCCG CTCGAGGTTA TCAAAGGTGG
601  TCGTCACCTG ATTTTCTGCC ACTCTAAAAA AAAATGCGAC GAACTGGCTG
651  CTAAGCTTGT TGCTCTGGGT ATCAACGCTG TTGCTTACTA CCGTGGTCTG
701  GACGTTTCTG TTATCCCGAC TTCTGGTGAC GTTGTTGTTG TGGCCACTGA
751  CGCTCTGATG ACTGGTTACA CTGGTGACTT CGACTCTGTT ATCGATTGCA
801  ACACTTGCAA TTCCATGTCT ACCAACCCGA AACCGCAGAA AAAAAACAAA
851  CGTAACACCA ACCGTCGTCC GCAGGACGTT AAATTCCCGG GTGGTGGTCA
901  GATCGTTAAA ACCTCTGAAC GTTCTCAGCC GCGTGGGCGT CGTCAGCCGA
951  TCCCGAAAGC TCGTCGTCCG GAAGGTCGTA CCTGGGCTCA GCCGGGTTAC
1001 CCGTGGCCGC TGTACGGTAA CGAAGGTTGC GGTTGGGCTG CTTGGCTGCT
1051 GTCTCCGTAA TAAGGATCC
```

SEQ ID NO:18

```
  1  MAVDFIPVEN LETTMRSPVF TDNSSPPVVP QSFQVAHLHA PTGSGKSTKV
 51  PAAYAAQGYK VLVLNPSVAA TLGFGAYMSK AHGIDPNIRT GVRTITTGSP
101  ITYSTYGKFL ADGGCSGGAY DIIICDECHS TDATSILGIG TVLDQAETAG
151  ARLVVLATAT PPGSVTVPHP NIEEVALSTT GEIPFYGKAI PLEVIKGGRH
201  LIFCHSKKKC DELAAKLVAL GINAVAYYRG LDVSIPTSG DVVVATDAL
251  MTGYTGDFDS VIDCNTCNSM STNPKPQKKN KRNTNRRPQD VKFPGGGQIV
301  KTSERSQPRG RRQPIPKARR PEGRTWAQPG YPWPLYGNEG CGWAGWLLSP
```

FIG.4D

SEQ ID NO:19

```
   1 GAATTCCATG GCTGTTGACT TTATCCCGGT TGAAAATCTC GAGACTACTA
  51 TGCGTTCTCC GGTTTTCACT GACAACTCTT CTCCGCCGGT TGTTCCGCAG
 101 TCTTTCCAGG TTGCTCACCT GCATGCTCCG ACTGGTTCTG GTAAATCTAC
 151 TAAAGTTCCA GCTGCTTACG CTGCTCAGGG TTACAAAGTT CTGGTTCTGA
 201 ACCCGTCTGT TGCTGCTACT CTGGGTTTCG GCGCCTACAT GTCTAAAGCT
 251 CACGGTATCG ACCCGAACAT TCGTACTGGT GTACGTACTA TCACTACTGG
 301 TTCTCCGATC ACTTACTCTA CTTACGGTAA ATTCCTGGCT GACGGTGGTT
 351 GCTCTGGTGG TGCTTACGAT ATCATCATCT GCGACGAATG CCACTCTACT
 401 GACGCTACTT CTATCCTGGG TATCGGTACC GTTCTGGACC AGGCTGAAAC
 451 TGCAGGTGCT CGTCTGGTTG TTCTGGCTAC TGCTACTCCG CCGGGTTCTG
 501 TTACTGTTCC GCACCCGAAC ATCGAAGAAG TTGCTCTGTC GACTACTGGT
 551 GAAATCCCGT TCTACGGTAA AGCTATCCCG CTCGAGGTTA TCAAAGGTGG
 601 TCGTCACCTG ATTTTCTGCC ACTCTAAAAA AAAATGCGAC GAACTGGCTG
 651 CTAAGCTTGT TGCTCTGGGT ATCAACGCTG TTGCTTACTA CCGTGGTCTG
 701 GACGTTTCTG TTATCCCGAC TTCTGGTGAC GTTGTTGTTG TGGCCACTGA
 751 CGCTCTGATG ACTGGTTACA CTGGTGACTT CGACTCTGTT ATCGATTGCA
 801 ACACTTGCAA TTCCATGCAG AAAAAAAACA AACGTAACAC CAACCGTCGT
 851 CCGCAGGACG TTAAATTCCC GGGTGGTGGT CAGATCGTTA AAACCTCTGA
 901 ACGTTCTCAG CCGCGTGGGC GTCGTCAGCC GATCCCGAAA GCTCGTCGTC
 951 CGGAAGGTCG TACCTGGGCT CAGCCGGGTT ACCCGTGGCC GCTGTACGGT
1001 AACGAAGGTT GCGGTTGGGC TGGTTGGCTG CTGTCTCCGT AATAAGGATC
1051 C
```

SEQ ID NO:20

```
   1 MAVDFIPVEN LETTMRSPVF TDNSSPPVVP QSFQVAHLHA PTGSGKSTKV
  51 PAAYAAQGYK VLVLNPSVAA TLGFGAYMSK AHGIDPNIRT GVRTITTGSP
 101 ITYSTYGKFL ADGGCSGGAY DIIICDECHS TDATSILGIG TVLDQAETAG
 151 ARLVVLATAT PPGSVTVPHP NIEEVALSTT GEIPFYGKAI PLEVIKGGRH
 201 LIFCHSKKKC DELAAKLVAL GINAVAYYRG LDVSVIPTSG DVVVVATDAL
 251 MTGYTGDFDS VIDCNTCNSM QKKNKRNTNR RPQDVKFPGG GQIVKTSERS
 301 QPRGRRQPIP KARRPEGRTW AQPGYPWPLY GNEGCGWAGW LLSP
```

FIG.4E

SEQ ID NO:21

5'- TATAGAATTC CATGGCTGTT GACTTTATCC -3'

SEQ ID NO:22

5'- GGAATTGCAA GTGTTGCAAT CGATAAC -3'

SEQ ID NO:23

5'- GTTATCGATT GCAACACTTG CAATTCCATG CAGAAAAAAA ACAAACGTAA C -3'

SEQ ID NO:24

```
   1 GAATTCCATG GCTGTTGACT TTATCCCGGT TGAAAATCTC GAGACTACTA
  51 TGCGTTCTCC GGTTTTCACT GACAACTCTT CTCCGCCGGT TGTTCCGCAG
 101 TCTTTCCAGG TTGCTCACCT GCATGCTCCG ACTGGTTCTG GTAAATCTAC
 151 TAAAGTTCCA GCTGCTTACG CTGCTCAGGG TTACAAAGTT CTGGTTCTGA
 201 ACCCGTCTGT TGCTGCTACT CTGGGTTTCG GCGCCTACAT GTCTAAAGCT
 251 CACGGTATCG ACCCGAACAT TCGTACTGGT GTACGTACTA TCACTACTGG
 301 TTCTCCGATC ACTTACTCTA CTTACGGTAA ATTCCTGGCT GACGGTGGTT
 351 GCTCTGGTGG TGCTTACGAT ATCATCATCT GCGACGAATG CCACTCTACT
 401 GACGCTACTT CTATCCTGGG TATCGGTACC GTTCTGGACC AGGCTGAAAC
 451 TGCAGGTGCT CGTCTGGTTG TTCTGGCTAC TGCTACTCCG CCGGGTTCTG
 501 TTACTGTTCC GCACCCGAAC ATCGAAGAAG TTGCTCTGTC GACTACTGGT
 551 GAAATCCCGT TCTACGGTAA AGCTATCCCG CTCGAGGTTA TCAAAGGTGG
 601 TCGTCACCTG ATTTTCTGCC ACTCTAAAAA AAAATGCGAC GAACTGGCTG
 651 CTAAGCTTGT TGCTCTGGGT ATCAACGCTG TTGCTTACTA CCGTGGTCTG
 701 GACGTTTCTG TTATCCCGAC TTCTGGTGAC GTTGTTGTTG TGGCCACTGA
 751 CGCTCTGATG ACTGGTTACA CTGGTGACTT CGACTCTGTT ATCGATTGCA
 801 ACACTTGCAA TTCCGGTGGT GGTGGTTCTA TGCAGAAAAA AAACAAACGT
 851 AACACCAACC GTCGTCCGCA GGACGTTAAA TTCCCGGGTG GTGGTCAGAT
 901 CGTTAAAACC TCTGAACGTT CTCAGCCGCG TGGGCGTCGT CAGCCGATCC
 951 CGAAAGCTCG TCGTCCGGAA GGTCGTACCT GGGCTCAGCC GGGTTACCCG
1001 TGGCCGCTGT ACGGTAACGA AGGTTGCGGT TGGGCTGGTT GGCTGCTGTC
1051 TCCGTAATAA GGATCC
```

FIG.4F

SEQ ID NO:25

```
  1  MAVDFIPVEN LETTMRSPVF TDNSSPPVVP QSFQVAHLHA PTGSGKSTKV
 51  PAAYAAQGYK VLVLNPSVAA TLGFGAYMSK AHGIDPNIRT GVRTITTGSP
101  ITYSTYGKFL ADGGCSGGAY DIIICDECHS TDATSILGIG TVLDQAETAG
151  ARLVVLATAT PPGSVTVPHP NIEEVALSTT GEIPFYGKAI PLEVIKGGRH
201  LIFCHSKKKC DELAAKLVAL GINAVAYYRG LDVSVIPTSG DVVVVATDAL
251  MTGYTGDFDS VIDCNTCNSG GGGSMQKKNK RNTNRRPQDV KFPGGGQIVK
301  TSERSQPRGR RQPIPKARRP EGRTWAQPGY PWPLYGNEGC GWAGWLLSP
```

SEQ ID NO:26

5'- GTTATCGATT GCAACACTTG CAATTCCGGT GGTGGTGGTT CTATGCAGAA
AAAAAACAAA CGTAAC -3'

SEQ ID NO:27

```
  1  GAATTCCATG GCTGTTGACT TTATCCCGGT TGAAAATCTC GAGACTACTA
 51  TGCGTTCTCC GGTTTTCACT GACAACTCTT CTCCGCCGGT TGTTCCGCAG
101  TCTTTCCAGG TTGCTCACCT GCATGCTCCG ACTGGTTCTG GTAAATCTAC
151  TAAAGTTCCA GCTGCTTACG CTGCTCAGGG TTACAAAGTT CTGGTTCTGA
201  ACCCGTCTGT TGCTGCTACT CTGGGTTTCG GCGCCTACAT GTCTAAAGCT
251  CACGGTATCG ACCCGAACAT TCGTACTGGT GTACGTACTA TCACTACTGG
301  TTCTCCGATC ACTTACTCTA CTTACGGTAA ATTCCTGGCT GACGGTGGTT
351  GCTCTGGTGG TGCTTACGAT ATCATCATCT GCGACGAATG CCACTCTACT
401  GACGCTACTT CTATCCTGGG TATCGGTACC GTTCTGGACC AGGCTGAAAC
451  TGCAGGTGCT CGTCTGGTTG TTCTGGCTAC TGCTACTCCG CCGGGTTCTG
501  TTACTGTTCC GCACCCGAAC ATCGAAGAAG TTGCTCTGTC GACTACTGGT
551  GAAATCCCGT TCTACGGTAA AGCTATCCCG CTCGAGGTTA TCAAAGGTGG
601  TCGTCACCTG ATTTTCTGCC ACTCTAAAAA AAAATGCGAC GAACTGGCTG
```

FIG.4G

```
651  CTAAGCTTGT TGCTCTGGGT ATCAACGCTG TTGCTTACTA CCGTGGTCTG
701  GACGTTTCTG TTATCCCGAC TTCTGGTGAC GTTGTTGTTG TGGCCACTGA
751  CGCTCTGATG ACTGGTTACA CTGGTGACTT CGACTCTGTT ATCGATTGCA
801  ACACTTGCAA TTCCGGTGGT GGTGGTTCTA TGTCTACCAA CCCGAAACCG
851  CAGAAAAAAA ACAAACGTAA CACCAACCGT CGTCCGCAGG ACGTTAAATT
901  CCCGGGTGGT GGTCAGATCG TTGGTGGTGT TTACCTGCTG CCGCGTCGTG
951  GTCCGCGTCT GGGTGTTCGT GCTACGCGTA AAACCTCTGA ACGTTCTCAG
1001 CCGCGTGGGC GTCGTCAGCC GATCCCGAAA GCTCGTCGTC CGGAAGGTCG
1051 TACCTGGGCT CAGCCGGGTT ACCCGTGGCC GCTGTACGGT AACGAAGGTT
1101 GCGGTTGGGC TGGTTGGCTG CTGTCTCCGC GTGGATCTCG TCCGTCTTGG
1151 GGTCCGACCG ACCCGCGTCG TCGTTCTCGT AACCTTGGTA AAGTTATCGA
1201 TACCCTGACC TGCGGTTTCG CTGACCTGAT GGGTTACATA CCGCTGGTTG
1251 GAGCTCCGCT GGGTGGTGCT GCTCGTGCTT AACCCATGGA TCC
```

SEQ ID NO:28

```
  1  MAVDFIPVEN LETTMRSPVF TDNSSPPVVP QSFQVAHLHA PTGSGKSTKV
 51  PAAYAAQGYK VLVLNPSVAA TLGFGAYMSK AHGIDPNIRT GVRTITTGSP
101  ITYSTYGKFL ADGGCSGGAY DIIICDECHS TDATSILGIG TVLDQAETAG
151  ARLVVLATAT PPGSVTVPHP NIEEVALSTT GEIPFYGKAI PLEVIKGGRH
201  LIFCHSKKKC DELAAKLVAL GINAVAYYRG LDVSIPTSG DVVVATDAL
251  MTGYTGDFDS VIDCNTCNSG GGGSMSTNPK PQKKNKRNTN RRPQDVKFPG
301  GGQIVGGVYL LPRRGPRLGV RATRKTSERS QPRGRRQPIP KARRPEGRTW
351  AQPGYPWPLY GNEGCGWAGW LLSPRGSRPS WGPTDPRRRS RNLGKVIDTL
401  TCGFADLMGY IPLVGAPLGG AARA
```

FIG.4H

SEQ ID NO:29

5'- GTTATCGATT GCAACACTTG CAATTCCGGT GGTGGTGGTT CTATGTCTAC CAACCCGAAA CCGCAG -3'

SEQ ID NO:30

5'- TATAGGATCC ATGGGTTAAG CACGAGC-3'

SEQ ID NO:31

```
  1 GAATTCCATG GCTGTTGACT TTATCCCGGT TGAAAATCTC GAGACTACTA
 51 TGCGTTCTCC GGTTTTCACT GACAACTCTT CTCCGCCGGT TGTTCCGCAG
101 TCTTTCCAGG TTGCTCACCT GCATGCTCCG ACTGGTTCTG GTAAATCTAC
151 TAAAGTTCCA GCTGCTTACG CTGCTCAGGG TTACAAAGTT CTGGTTCTGA
201 ACCCGTCTGT TGCTGCTACT CTGGGTTTCG GCGCCTACAT GTCTAAAGCT
251 CACGGTATCG ACCCGAACAT TCGTACTGGT GTACGTACTA TCACTACTGG
301 TTCTCCGATC ACTTACTCTA CTTACGGTAA ATTCCTGGCT GACGGTGGTT
351 GCTCTGGTGG TGCTTACGAT ATCATCATCT GCGACGAATG CCACTCTACT
401 GACGCTACTT CTATCCTGGG TATCGGTACC GTTCTGGACC AGGCTGAAAC
451 TGCAGGTGCT CGTCTGGTTG TTCTGGCTAC TGCTACTCCG CCGGGTTCTG
501 TTACTGTTCC GCACCCGAAC ATCGAAGAAG TTGCTCTGTC GACTACTGGT
551 GAAATCCCGT TCTACGGTAA AGCTATCCCG CTCGAGGTTA TCAAAGGTGG
601 TCGTCACCTG ATTTTCTGCC ACTCTAAAAA AAAATGCGAC GAACTGGCTG
651 CTAAGCTTGT TGCTCTGGGT ATCAACGCTG TTGCTTACTA CCGTGGTCTG
701 GACGTTTCTG TTATCCCGAC TTCTGGTGAC GTTGTTGTTG TGGCCACTGA
751 CGCTCTGATG ACTGGTTACA CTGGTGACTT CGACTCTGTT ATCGATTGCA
801 ACACTTGCAA TTCCATGTCT ACCAACCCGA AACCGCAGAA AAAAAACAAA
```

FIG.41

```
 851 CGTAACACCA ACCGTCGTCC GCAGGACGTT AAATTCCCGG GTGGTGGTCA
 901 GATCGTTTAC CTGCTGCCGC GTCGTGGTCC GCGTCTGGGT GTTACGCGTA
 951 AAACCTCTGA ACGTTCTCAG CCGCGTGGGC GTCGTCAGCC GATCCCGAAA
1001 GCTCGTCGTC CGGAAGGTCG TACCTGGGCT CAGCCGGGTT ACCCGTGGCC
1051 GCTGTACGGT AACGAAGGTT GCGGTTGGGC TGGTTGGCTA CTGTCTCCGT
1101 AATAAGGATC C
```

SEQ ID NO:32

```
  1 MAVDFIPVEN LETTMRSPVF TDNSSPPVVP QSFQVAHLHA PTGSGKSTKV
 51 PAAYAAQGYK VLVLNPSVAA TLGFGAYMSK AHGIDPNIRT GVRTITTGSP
101 ITYSTYGKFL ADGGCSGGAY DIIICDECHS TDATSILGIG TVLDQAETAG
151 ARLVVLATAT PPGSVTVPHP NIEEVALSTT GEIPFYGKAI PLEVIKGGRH
201 LIFCHSKKKC DELAAKLVAL GINAVAYYRG LDVSVIPTSG DVVVVATDAL
251 MTGYTGDFDS VIDCNTCNSM STNPKPQKKN KRNTNRRPQD VKFPGGGQIV
301 YLLPRRGPRL GVTRKTSERS QPRGRRQPIP KARRPEGRTW AQPGYPWPLY
351 GNEGCGWAGW LLSP
```

SEQ ID NO:33

5'- ACCCAGACGC GGACCACGAC GCGGCAGCAG GTAAACGATC TGACCACCAC CC -3'

SEQ ID NO:34

5'- CCGCGTCGTG GTCCGCGTCT GGGTGTTACG CGTAAAACCT CTGAACGTTC TCAG -3'

SEQ ID NO:35

KTKRNTNRRPQDVKFPGGGQIVYLLPRRGPRLGVTRKTS

FIG.4J

SEQ ID NO:36

KTKRNTNRRPQDVKFPGGGQIVGGVYLLPRRGPRLGVRATRKTS

SEQ ID NO:37

KTKRNTNRRPQDVKFPGGGQIVKTS

FIG.4K

SEQUENCE LISTING

<160> NUMBER OF SEQ ID NOS: 63

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
atagaattcc atgcagaaaa aaaacaaacg taacaccaac                40

<210> SEQ ID NO 2
<211> LENGTH: 46
<212> TYPE: DNA
<213> ORGANISM: Artificial Sequence
<220> FEATURE:
<223> OTHER INFORMATION: Primer

<400> SEQUENCE: 2
cggctgagaa cgttcagagg ttttaacgat ctgaccacca cccggg          46

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
aaaacctctg aacgttctca gccg                                  24

<210> SEQ ID NO 4
<211> LENGTH: 36
<212> TYPE: DNA

<213> ORGANISM: Artificial Sequence
<220> FEATURE:
<223> OTHER INFORMATION: Primer

<400> SEQUENCE: 4

```
tatggatcct tattacggag acagcagcca accagc                                     36
```

<210> SEQ ID NO 5
<211> LENGTH: 244
<212> TYPE: DNA
<213> ORGANISM: Hepatitis C Virus

<400> SEQUENCE: 5

```
gaattccatg cagaaaaaaa acaaacgtaa caccaaccgt cgtccgcagg acgttaaatt           60
cccgggtggt ggtcagatcg ttaaaacctc tgaacgttct cagccgcgtg ggcgtcgtca          120
gccgatcccg aaagctcgtc gtccggaagg tcgtacctgg gctcagccgg gttacccgtg          180
gccgctgtac ggtaacgaag gttgcggttg ggcaggttgg ctgctgtctc cgtaataagg          240
atcc                                                                      244
```

<210> SEQ ID NO 6
<211> LENGTH: 75
<212> TYPE: PRT
<213> ORGANISM: Hepatitis C Virus

<400> SEQUENCE: 6

```
Met Gln Lys Lys Asn Lys Arg Asn Thr Asn Arg Arg Pro Gln Asp Val
  1               5                  10                  15
Lys Phe Pro Gly Gly Gly Gln Ile Val Lys Thr Ser Glu Arg Ser Gln
             20                  25                  30
Pro Arg Gly Arg Arg Gln Pro Ile Pro Lys Ala Arg Arg Pro Glu Gly
         35                  40                  45
Arg Thr Trp Ala Gln Pro Gly Tyr Pro Trp Pro Leu Tyr Gly Asn Glu
     50                  55                  60
Gly Cys Gly Trp Ala Gly Trp Leu Leu Ser Pro
 65                  70                  75
```

<210> SEQ ID NO 7
<211> LENGTH: 280
<212> TYPE: DNA
<213> ORGANISM: Artificial Sequence
<220> FEATURE:
<223> OTHER INFORMATION: Variant - HVC-Core Recombinant

<400> SEQUENCE: 7

```
gaattccatg cagaaaaaaa acaaacgtaa caccaaccgt cgtccgcagg acgttaaatt           60
cccgggtggt ggtcagatcg ttggtctgct gccgcgtcgt ggtccgcgtc tgggtcgtaa          120
aacctctgaa cgttctcagc cgcgtgggcg tcgtcagccg atcccgaaag ctcgtcgtcc          180
ggaaggtcgt acctgggctc agccgggtta cccgtggccg ctgtacggta acgaaggttg          240
cggttgggct ggttggctgc tgtctccgta ataaggatcc                                280
```

<210> SEQ ID NO 8
<211> LENGTH: 87
<212> TYPE: PRT
<213> ORGANISM: Artificial Sequence
<220> FEATURE:
<223> OTHER INFORMATION: Variant - HVC-Core Recombinant

<400> SEQUENCE: 8

```
Met Gln Lys Lys Asn Lys Arg Asn Thr Asn Arg Arg Pro Gln Asp Val
1               5                   10                  15

Lys Phe Pro Gly Gly Gly Gln Ile Val Gly Leu Leu Pro Arg Arg Gly
            20                  25                  30

Pro Arg Leu Gly Arg Lys Thr Ser Glu Arg Ser Gln Pro Arg Gly Arg
                35                  40                  45

Arg Gln Pro Ile Pro Lys Ala Arg Arg Pro Glu Gly Arg Thr Trp Ala
        50                  55                  60

Gln Pro Gly Tyr Pro Trp Pro Leu Tyr Gly Asn Glu Gly Cys Gly Trp
65                  70                  75                  80

Ala Gly Trp Leu Leu Ser Pro
                85
```

<210> SEQ ID NO 9
<211> LENGTH: 52
<212> TYPE: DNA
<213> ORGANISM: Artificial Sequence
<220> FEATURE:
<223> OTHER INFORMATION: Primer

<400> SEQUENCE: 9
acccagacgc ggaccacgac gcggcagcag accaacgatc tgaccaccac cc       52

<210> SEQ ID NO 10
<211> LENGTH: 48
<212> TYPE: DNA
<213> ORGANISM: Artificial Sequence
<220> FEATURE:
<223> OTHER INFORMATION: Primer

<400> SEQUENCE: 10
ccgcgtcgtg gtccgcgtct gggtcgtaaa acctctgaac gttctcag             48

<210> SEQ ID NO 11
<211> LENGTH: 301
<212> TYPE: DNA
<213> ORGANISM: Artificial Sequence
<220> FEATURE:
<223> OTHER INFORMATION: Variant - HVC-Core Recombinant

<400> SEQUENCE: 11
gaattccatg cagaaaaaaa acaaacgtaa caccaaccgt cgtccgcagg acgttaaatt    60
cccgggtggt ggtcagatcg ttggtggtgt ttacgttctg ccgcgtcgtg gtccgcgtct   120
gggtgttctg gctacgcgta aaacctctga acgttctcag ccgcgtgggc gtcgtcagcc   180
gatcccgaaa gctcgtcgtc cggaaggtcg tacctgggct cagccgggtt acccgtggcc   240
gctgtacggt aacgaaggtt gcggttgggc tggttggctg ctgtctccgt aataaggatc   300
c                                                                  301

<210> SEQ ID NO 12
<211> LENGTH: 94
<212> TYPE: PRT
<213> ORGANISM: Artificial Sequence
<220> FEATURE:
<223> OTHER INFORMATION: Variant - HVC-Core Recombinant

<400> SEQUENCE: 12

```
Met Gln Lys Lys Asn Lys Arg Asn Thr Asn Arg Arg Pro Gln Asp Val
1               5                   10                  15

Lys Phe Pro Gly Gly Gly Gln Ile Val Gly Gly Val Tyr Val Leu Pro
            20                  25                  30
```

Arg Arg Gly Pro Arg Leu Gly Val Leu Ala Thr Arg Lys Thr Ser Glu
              35                  40                  45

Arg Ser Gln Pro Arg Gly Arg Gln Pro Ile Pro Lys Ala Arg Arg
     50                  55                  60

Pro Glu Gly Arg Thr Trp Ala Gln Pro Gly Tyr Pro Trp Pro Leu Tyr
65                  70                  75                  80

Gly Asn Glu Gly Cys Gly Trp Ala Gly Trp Leu Leu Ser Pro
                85                  90

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
acccagacgc ggaccacgac gcggcagaac gtaaacacca ccaac         45

<210> SEQ ID NO 14
<211> LENGTH: 45
<212> TYPE: DNA
<213> ORGANISM: Artificial Sequence
<220> FEATURE:
<223> OTHER INFORMATION: Primer

<400> SEQUENCE: 14
ccgcgtcgtg gtccgcgtct gggtgttctg gctacgcgta aaacc         45

<210> SEQ ID NO 15
<211> LENGTH: 300
<212> TYPE: DNA
<213> ORGANISM: Artificial Sequence
<220> FEATURE:
<223> OTHER INFORMATION: Variant - HCV-Core Recombinant
<220> FEATURE:
<221> NAME/KEY: misc_feature
<222> LOCATION: (100)...(100)
<223> OTHER INFORMATION: n = a or g or c or t/u, unknown, or other at
      position 100

<400> SEQUENCE: 15
gaattccatg cagaaaaaaa acaaacgtaa caccaaccgt cgtccgcagg acgttaaatt     60
cccgggtggt ggtcagatcg ttggtggtgt ttacctgctn ccgcgtcgtg gtccgcgtct    120
gggtgttcgt gctacgcgta aaacctctga acgttctcag ccgcgtgggc gtcgtcagcc    180
gatccgaaag ctcgtcgtcc ggaaggtcgt acctgggctc agccgggtta cccgtggccg    240
ctgtacggta acgaaggttg cggttgggct ggttggctgc tgtctccgta ataaggatcc    300

<210> SEQ ID NO 16
<211> LENGTH: 94
<212> TYPE: PRT
<213> ORGANISM: Artificial Sequence
<220> FEATURE:
<223> OTHER INFORMATION: Variant - HCV-Core Recombinant

<400> SEQUENCE: 16

Met Gln Lys Lys Asn Lys Arg Asn Thr Asn Arg Arg Pro Gln Asp Val
1               5                   10                  15

Lys Phe Pro Gly Gly Gly Gln Ile Val Gly Gly Val Tyr Leu Leu Pro
            20                  25                  30

Arg Arg Gly Pro Arg Leu Gly Val Arg Ala Thr Arg Lys Thr Ser Glu

```
                35                  40                  45
Arg Ser Gln Pro Arg Gly Arg Gln Pro Ile Pro Lys Ala Arg Arg
    50                  55                  60

Pro Glu Gly Arg Thr Trp Ala Gln Pro Gly Tyr Pro Trp Pro Leu Tyr
65                  70                  75                  80

Gly Asn Glu Gly Cys Gly Trp Ala Gly Trp Leu Leu Ser Pro
                85                  90

<210> SEQ ID NO 17
<211> LENGTH: 1069
<212> TYPE: DNA
<213> ORGANISM: Hepatitis C Virus
<220> FEATURE:
<223> OTHER INFORMATION: p9MB-18

<400> SEQUENCE: 17
gaattccatg gctgttgact ttatcccggt tgaaaatctc gagactacta tgcgttctcc      60
ggttttcact gacaactctt ctccgccggt tgttccgcag tctttccagg ttgctcacct     120
gcatgctccg actggttctg gtaaatctac taaagttcca gctgcttacg ctgctcaggg     180
ttacaaagtt ctggttctga acccgtctgt tgctgctact ctgggtttcg cgcctacat      240
gtctaaagct cacggtatcg acccgaacat tcgtactggt gtacgtacta tcactactgg     300
ttctccgatc acttactcta cttacggtaa attcctggct gacgtggttt gctctggtgg     360
tgcttacgat atcatcatct gcgacgaatg ccactctact gacgctactt ctatcctggg     420
tatcggtacc gttctggacc aggctgaaac tgcaggtgct cgtctggttg ttctggctac     480
tgctactccg ccgggttctg ttactgttcc gcacccgaac atcgaagaag ttgctctgtc     540
gactactggt gaaatcccgt tctacggtaa agctatcccg ctcgaggtta tcaaaggtgg     600
tcgtcacctg attttctgcc actctaaaaa aaaatgcgac gaactggctg ctaagcttgt     660
tgctctgggt atcaacgctg ttgcttacta ccgtggtctg gacgtttctg ttatcccgac     720
ttctggtgac gttgttgttg tggccactga cgctctgatg actggttaca ctggtgactt     780
cgactctgtt atcgattgca acacttgcaa ttccatgtct accaacccga accgcagaa      840
aaaaaacaaa cgtaacacca accgtcgtcc gcaggacgtt aaattcccgg tggtggtca      900
gatcgttaaa acctctgaac gttctcagcc gcgtgggcgt cgtcagccga tcccgaaagc     960
tcgtcgtccg gaaggtcgta cctgggctca gccgggttac ccgtggccgc tgtacggtaa    1020
cgaaggttgc ggttgggctg gttggctgct gtctccgtaa taaggatcc                1069

<210> SEQ ID NO 18
<211> LENGTH: 350
<212> TYPE: PRT
<213> ORGANISM: Hepatitis C Virus
<220> FEATURE:
<223> OTHER INFORMATION: p9MB-18

<400> SEQUENCE: 18

Met Ala Val Asp Phe Ile Pro Val Glu Asn Leu Glu Thr Thr Met Arg
1               5                   10                  15

Ser Pro Val Phe Thr Asp Asn Ser Ser Pro Pro Val Val Pro Gln Ser
                20                  25                  30

Phe Gln Val Ala His Leu His Ala Pro Thr Gly Ser Gly Lys Ser Thr
            35                  40                  45

Lys Val Pro Ala Ala Tyr Ala Ala Gln Gly Tyr Lys Val Leu Val Leu
        50                  55                  60
```

-continued

| | | | | | | | | | | | | | | | |
|---|---|---|---|---|---|---|---|---|---|---|---|---|---|---|---|
|Asn|Pro|Ser|Val|Ala|Ala|Thr|Leu|Gly|Phe|Gly|Ala|Tyr|Met|Ser|Lys|
|65| | | | |70| | | | |75| | | | |80|

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
                100                 105                 110

Gly Gly Cys Ser Gly Gly Ala Tyr Asp Ile Ile Ile Cys Asp Glu Cys
                115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
                180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly Asp
                245                 250                 255

Asp Phe Asp Ser Val Ile Asp Cys Asn Thr Cys Asn Ser Met Ser Thr
                260                 265                 270

Asn Pro Lys Pro Gln Lys Lys Asn Lys Arg Asn Thr Asn Arg Arg Pro
        275                 280                 285

Gln Asp Val Lys Phe Pro Gly Gly Gln Ile Val Lys Thr Ser Glu
290                 295                 300

Arg Ser Gln Pro Arg Gly Arg Arg Gln Pro Ile Pro Lys Ala Arg Arg
305                 310                 315                 320

Pro Glu Gly Arg Thr Trp Ala Gln Pro Gly Tyr Pro Trp Pro Leu Tyr
                325                 330                 335

Gly Asn Glu Gly Cys Gly Trp Ala Gly Trp Leu Leu Ser Pro
            340                 345                 350

<210> SEQ ID NO 19
<211> LENGTH: 1051
<212> TYPE: DNA
<213> ORGANISM: Hepatitis C Virus
<220> FEATURE:
<223> OTHER INFORMATION: p9MB-19

<400> SEQUENCE: 19

| | | | | | |
|---|---|---|---|---|---|
|gaattccatg|gctgttgact|ttatcccggt|tgaaaatctc|gagactacta|tgcgttctcc|60|
|ggttttcact|gacaactctt|ctccgccggt|tgttccgcag|tctttccagg|ttgctcacct|120|
|gcatgctccg|actggttctg|gtaaatctac|taaagttcca|gctgcttacg|ctgctcaggg|180|
|ttacaaagtt|ctggttctga|acccgtctgt|tgctgctact|ctgggtttcg|gcgcctacat|240|
|gtctaaagct|cacggtatcg|acccgaacat|tcgtactggt|gtacgtacta|tcactactgg|300|
|ttctccgatc|acttactcta|cttacggtaa|attcctggct|gacggtggtt|gctctggtgg|360|
|tgcttacgat|atcatcatct|gcgacgaatg|ccactctact|gacgctactt|ctatcctggg|420|
|tatcggtacc|gttctggacc|aggctgaaac|tgcaggtgct|cgtctggttg|ttctggctac|480|

```
tgctactccg ccgggttctg ttactgttcc gcacccgaac atcgaagaag ttgctctgtc      540
gactactggt gaaatcccgt tctacggtaa agctatcccg ctcgaggtta tcaaaggtgg      600
tcgtcacctg attttctgcc actctaaaaa aaaatgcgac gaactggctg ctaagcttgt      660
tgctctgggt atcaacgctg ttgcttacta ccgtggtctg gacgtttctg ttatcccgac      720
ttctggtgac gttgttgttg tggccactga cgctctgatg actggttaca ctggtgactt      780
cgactctgtt atcgattgca cacttgcaa ttccatgcag aaaaaaaaca aacgtaacac       840
caaccgtcgt ccgcaggacg ttaaattccc gggtggtggt cagatcgtta aaacctctga      900
acgttctcag ccgcgtgggc gtcgtcagcc gatcccgaaa gctcgtcgtc cggaaggtcg      960
tacctgggct cagccgggtt acccgtggcc gctgtacggt aacgaaggtt gcggttgggc     1020
tggttggctg ctgtctccgt aataaggatc c                                    1051
```

<210> SEQ ID NO 20
<211> LENGTH: 344
<212> TYPE: PRT
<213> ORGANISM: Hepatitis C Virus
<220> FEATURE:
<223> OTHER INFORMATION: p9MB-19

<400> SEQUENCE: 20

```
Met Ala Val Asp Phe Ile Pro Val Glu Asn Leu Glu Thr Thr Met Arg
  1               5                  10                  15

Ser Pro Val Phe Thr Asp Asn Ser Ser Pro Val Val Pro Gln Ser
             20                  25                  30

Phe Gln Val Ala His Leu His Ala Pro Thr Gly Ser Gly Lys Ser Thr
         35                  40                  45

Lys Val Pro Ala Ala Tyr Ala Ala Gln Gly Tyr Lys Val Leu Val Leu
     50                  55                  60

Asn Pro Ser Val Ala Ala Thr Leu Gly Phe Gly Ala Tyr Met Ser Lys
 65                  70                  75                  80

Ala His Gly Ile Asp Pro Asn Ile Arg Thr Gly Val Arg Thr Ile Thr
                 85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255
```

```
Asp Phe Asp Ser Val Ile Asp Cys Asn Thr Cys Asn Ser Met Gln Lys
                260                 265                 270
Lys Asn Lys Arg Asn Thr Asn Arg Arg Pro Gln Asp Val Lys Phe Pro
            275                 280                 285
Gly Gly Gly Gln Ile Val Lys Thr Ser Glu Arg Ser Gln Pro Arg Gly
        290                 295                 300
Arg Arg Gln Pro Ile Pro Lys Ala Arg Arg Pro Glu Gly Arg Thr Trp
305                 310                 315                 320
Ala Gln Pro Gly Tyr Pro Trp Pro Leu Tyr Gly Asn Glu Gly Cys Gly
                325                 330                 335
Trp Ala Gly Trp Leu Leu Ser Pro
            340

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
tatagaattc catggctgtt gactttatcc                                    30

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
ggaattgcaa gtgttgcaat cgataac                                       27

<210> SEQ ID NO 23
<211> LENGTH: 51
<212> TYPE: DNA
<213> ORGANISM: Artificial Sequence
<220> FEATURE:
<223> OTHER INFORMATION: Primer

<400> SEQUENCE: 23
gttatcgatt gcaacacttg caattccatg cagaaaaaaa acaaacgtaa c             51

<210> SEQ ID NO 24
<211> LENGTH: 1066
<212> TYPE: DNA
<213> ORGANISM: Hepatitis C Virus
<220> FEATURE:
<223> OTHER INFORMATION: p9MB-20

<400> SEQUENCE: 24
gaattccatg gctgttgact ttatcccggt tgaaatctc gagactacta tgcgttctcc    60
ggttttcact gacaactctt ctccgccggt tgttccgcag tctttccagg ttgctcacct  120
gcatgctccg actggttctg gtaaatctac taaagttcca gctgcttacg ctgctcaggg  180
ttacaaagtt ctggttctga cccgtctgt tgctgctact ctgggtttcg cgcctacat   240
gtctaaagct cacggtatcg acccgaacat tcgtactggt gtacgtacta tcactactgg  300
ttctccgatc acttactcta cttacggtaa attcctggct gacggtggtt gctctggtgg  360
tgcttacgat atcatcatct gcgacgaatg ccactctact gacgctactt ctatcctggg  420
tatcggtacc gttctggacc aggctgaaac tgcaggtgct cgtctggttg ttctggctac  480
```

-continued

```
tgctactccg ccgggttctg ttactgttcc gcacccgaac atcgaagaag ttgctctgtc    540
gactactggt gaaatcccgt tctacggtaa agctatcccg ctcgaggtta tcaaaggtgg    600
tcgtcacctg attttctgcc actctaaaaa aaaatgcgac gaactggctg ctaagcttgt    660
tgctctgggt atcaacgctg ttgcttacta ccgtggtctg gacgtttctg ttatcccgac    720
ttctggtgac gttgttgttg tggccactga cgctctgatg actggttaca ctggtgactt    780
cgactctgtt atcgattgca acacttgcaa ttccggtggt ggtggttcta tgcagaaaaa    840
aaacaaacgt aacaccaacc gtcgtccgca ggacgttaaa ttcccgggtg gtggtcagat    900
cgttaaaacc tctgaacgtt ctcagccgcg tgggcgtcgt cagccgatcc cgaaagctcg    960
tcgtccggaa ggtcgtacct gggctcagcc gggttacccg tggccgctgt acggtaacga   1020
aggttgcggt tgggctggtt ggctgctgtc tccgtaataa ggatcc                   1066
```

<210> SEQ ID NO 25
<211> LENGTH: 349
<212> TYPE: PRT
<213> ORGANISM: Hepatitis C Virus
<220> FEATURE:
<223> OTHER INFORMATION: p9MB-20

<400> SEQUENCE: 25

```
Met Ala Val Asp Phe Ile Pro Val Glu Asn Leu Glu Thr Thr Met Arg
 1               5                  10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255
```

```
Asp Phe Asp Ser Val Ile Asp Cys Asn Thr Cys Asn Ser Gly Gly Gly
            260                 265                 270

Gly Ser Met Gln Lys Lys Asn Lys Arg Asn Thr Asn Arg Arg Pro Gln
        275                 280                 285

Asp Val Lys Phe Pro Gly Gly Gly Gln Ile Val Lys Thr Ser Glu Arg
    290                 295                 300

Ser Gln Pro Arg Gly Arg Arg Gln Pro Ile Pro Lys Ala Arg Arg Pro
305                 310                 315                 320

Glu Gly Arg Thr Trp Ala Gln Pro Gly Tyr Pro Trp Pro Leu Tyr Gly
                325                 330                 335

Asn Glu Gly Cys Gly Trp Ala Gly Trp Leu Leu Ser Pro
                340                 345

<210> SEQ ID NO 26
<211> LENGTH: 66
<212> TYPE: DNA
<213> ORGANISM: Artificial Sequence
<220> FEATURE:
<223> OTHER INFORMATION: Primer

<400> SEQUENCE: 26
gttatcgatt gcaacacttg caattccggt ggtggtggtt ctatgcagaa aaaaaacaaa      60
cgtaac                                                                 66

<210> SEQ ID NO 27
<211> LENGTH: 1293
<212> TYPE: DNA
<213> ORGANISM: Hepatitis C Virus
<220> FEATURE:
<223> OTHER INFORMATION: p9MB-22

<400> SEQUENCE: 27
gaattccatg gctgttgact ttatcccggt tgaaatctc gagactacta tgcgttctcc       60
ggttttcact gacaactctt ctccgccggt tgttccgcag tctttccagg ttgctcacct     120
gcatgctccg actggttctg gtaaatctac taaagttcca gctgcttacg ctgctcaggg    180
ttacaaagtt ctggttctga cccgtctgt tgctgctact ctgggtttcg gcgcctacat     240
gtctaaagct cacggtatcg acccgaacat tcgtactggt gtacgtacta tcactactgg    300
ttctccgatc acttactcta cttacggtaa attcctggct gacggtggtt gctctggtgg    360
tgcttacgat atcatcatct gcgacgaatg ccactctact gacgctactt ctatcctggg    420
tatcggtacc gttctggacc aggctgaaac tgcaggtgct cgtctggttg ttctggctac    480
tgctactccg ccgggttctg ttactgttcc gcacccgaac atcgaagaag ttgctctgtc    540
gactactggt gaaatcccgt tctacggtaa agctatcccg ctcgaggtta tcaaaggtgg    600
tcgtcacctg attttctgcc actctaaaaa aaaatgcgac gaactggctg ctaagcttgt    660
tgctctgggt atcaacgctg ttgcttacta ccgtggtctg gacgtttctg ttatcccgac    720
ttctggtgac gttgttgttg tggccactga cgctctgatg actggttaca ctggtgactt    780
cgactctgtt atcgattgca acacttgcaa ttccggtggt ggtggttcta tgtctaccaa    840
cccgaaaccg cagaaaaaaa acaaacgtaa caccaaccgt cgtccgcagg acgttaaatt    900
cccgggtggt ggtcagatcg ttggtggtgt ttacctgctg ccgcgtcgtg gtccgcgtct    960
gggtgttcgt gctacgcgta aaacctctga acgttctcag ccgcgtgggc gtcgtcagcc   1020
gatcccgaaa gctcgtcgtc cggaaggtcg tacctgggct cagccgggtt acccgtggcc   1080
gctgtacggt aacgaaggtt gcggttgggc tggttggctg ctgtctccgc gtggatctcg   1140
```

-continued

```
tccgtcttgg ggtccgaccg acccgcgtcg tcgttctcgt aaccttggta aagttatcga    1200
taccctgacc tgcggtttcg ctgacctgat gggttacata ccgctggttg gagctccgct    1260
gggtggtgct gctcgtgctt aacccatgga tcc                                 1293
```

<210> SEQ ID NO 28
<211> LENGTH: 424
<212> TYPE: PRT
<213> ORGANISM: Hepatitis C Virus
<220> FEATURE:
<223> OTHER INFORMATION: p9MB-22

<400> SEQUENCE: 28

| | | | | | | | | | | | | | | |
|---|---|---|---|---|---|---|---|---|---|---|---|---|---|---|
| Met | Ala | Val | Asp | Phe | Ile | Pro | Val | Glu | Asn | Leu | Glu | Thr | Thr | Met | Arg |
| 1 | | | | 5 | | | | | 10 | | | | | 15 | |
| Ser | Pro | Val | Phe | Thr | Asp | Asn | Ser | Ser | Pro | Val | Val | Pro | Gln | Ser | |
| | | | 20 | | | | | 25 | | | | | 30 | | |
| Phe | Gln | Val | Ala | His | Leu | His | Ala | Pro | Thr | Gly | Ser | Gly | Lys | Ser | Thr |
| | | | 35 | | | | | 40 | | | | | 45 | | |
| Lys | Val | Pro | Ala | Ala | Tyr | Ala | Ala | Gln | Gly | Tyr | Lys | Val | Leu | Val | Leu |
| 50 | | | | | 55 | | | | | 60 | | | | | |
| Asn | Pro | Ser | Val | Ala | Ala | Thr | Leu | Gly | Phe | Gly | Ala | Tyr | Met | Ser | Lys |
| 65 | | | | | 70 | | | | | 75 | | | | | 80 |
| Ala | His | Gly | Ile | Asp | Pro | Asn | Ile | Arg | Thr | Gly | Val | Arg | Thr | Ile | Thr |
| | | | | 85 | | | | | 90 | | | | | 95 | |
| Thr | Gly | Ser | Pro | Ile | Thr | Tyr | Ser | Thr | Tyr | Gly | Lys | Phe | Leu | Ala | Asp |
| | | | | 100 | | | | | 105 | | | | | 110 | |
| Gly | Gly | Cys | Ser | Gly | Gly | Ala | Tyr | Asp | Ile | Ile | Ile | Cys | Asp | Glu | Cys |
| | | | | 115 | | | | | 120 | | | | | 125 | |
| His | Ser | Thr | Asp | Ala | Thr | Ser | Ile | Leu | Gly | Ile | Gly | Thr | Val | Leu | Asp |
| 130 | | | | | 135 | | | | | 140 | | | | | |
| Gln | Ala | Glu | Thr | Ala | Gly | Ala | Arg | Leu | Val | Val | Leu | Ala | Thr | Ala | Thr |
| 145 | | | | | 150 | | | | | 155 | | | | | 160 |
| Pro | Pro | Gly | Ser | Val | Thr | Val | Pro | His | Pro | Asn | Ile | Glu | Glu | Val | Ala |
| | | | | 165 | | | | | 170 | | | | | 175 | |
| Leu | Ser | Thr | Thr | Gly | Glu | Ile | Pro | Phe | Tyr | Gly | Lys | Ala | Ile | Pro | Leu |
| | | | | 180 | | | | | 185 | | | | | 190 | |
| Glu | Val | Ile | Lys | Gly | Gly | Arg | His | Leu | Ile | Phe | Cys | His | Ser | Lys | Lys |
| | | | | 195 | | | | | 200 | | | | | 205 | |
| Lys | Cys | Asp | Glu | Leu | Ala | Ala | Lys | Leu | Val | Ala | Leu | Gly | Ile | Asn | Ala |
| | | | | 210 | | | | | 215 | | | | | 220 | |
| Val | Ala | Tyr | Tyr | Arg | Gly | Leu | Asp | Val | Ser | Val | Ile | Pro | Thr | Ser | Gly |
| 225 | | | | | 230 | | | | | 235 | | | | | 240 |
| Asp | Val | Val | Val | Ala | Thr | Asp | Ala | Leu | Met | Thr | Gly | Tyr | Thr | Gly |
| | | | | 245 | | | | | 250 | | | | | 255 | |
| Asp | Phe | Asp | Ser | Val | Ile | Asp | Cys | Asn | Thr | Cys | Asn | Ser | Gly | Gly | Gly |
| | | | | 260 | | | | | 265 | | | | | 270 | |
| Gly | Ser | Met | Ser | Thr | Asn | Pro | Lys | Pro | Gln | Lys | Lys | Asn | Lys | Arg | Asn |
| | | | | 275 | | | | | 280 | | | | | 285 | |
| Thr | Asn | Arg | Arg | Pro | Gln | Asp | Val | Lys | Phe | Pro | Gly | Gly | Gly | Gln | Ile |
| | | | | 290 | | | | | 295 | | | | | 300 | |
| Val | Gly | Gly | Val | Tyr | Leu | Leu | Pro | Arg | Arg | Gly | Pro | Arg | Leu | Gly | Val |
| 305 | | | | | 310 | | | | | 315 | | | | | 320 |
| Arg | Ala | Thr | Arg | Lys | Thr | Ser | Glu | Arg | Ser | Gln | Pro | Arg | Gly | Arg | Arg |
| | | | | 325 | | | | | 330 | | | | | 335 | |

Gln Pro Ile Pro Lys Ala Arg Arg Pro Glu Gly Arg Thr Trp Ala Gln
            340                 345                 350

Pro Gly Tyr Pro Trp Pro Leu Tyr Gly Asn Glu Gly Cys Gly Trp Ala
            355                 360                 365

Gly Trp Leu Leu Ser Pro Arg Gly Ser Arg Pro Ser Trp Gly Pro Thr
370                 375                 380

Asp Pro Arg Arg Ser Arg Asn Leu Gly Lys Val Ile Asp Thr Leu
385                 390                 395                 400

Thr Cys Gly Phe Ala Asp Leu Met Gly Tyr Ile Pro Leu Val Gly Ala
                405                 410                 415

Pro Leu Gly Gly Ala Ala Arg Ala
            420

<210> SEQ ID NO 29
<211> LENGTH: 66
<212> TYPE: DNA
<213> ORGANISM: Artificial Sequence
<220> FEATURE:
<223> OTHER INFORMATION: Primer

<400> SEQUENCE: 29
gttatcgatt gcaacacttg caattccggt ggtggtggtt ctatgtctac caacccgaaa      60
ccgcag                                                                 66

<210> SEQ ID NO 30
<211> LENGTH: 27
<212> TYPE: DNA
<213> ORGANISM: Artificial Sequence
<220> FEATURE:
<223> OTHER INFORMATION: Primer

<400> SEQUENCE: 30
tataggatcc atgggttaag cacgagc                                          27

<210> SEQ ID NO 31
<211> LENGTH: 1111
<212> TYPE: DNA
<213> ORGANISM: Hepatitis C Virus
<220> FEATURE:
<223> OTHER INFORMATION: p9MB-31

<400> SEQUENCE: 31
gaattccatg gctgttgact ttatcccggt tgaaatctct gagactacta tgcgttctcc      60
ggttttcact gacaactctt ctccgccggt tgttccgcag tctttccagg ttgctcacct     120
gcatgctccg actggttctg gtaaatctac taaagttcca gctgcttacg ctgctcaggg     180
ttacaaagtt ctggttctga cccgtctgt tgctgctact ctgggtttcg cgcctacat      240 gtctaaagct cacggtatcg acccgaacat tcgtactggt gtacgtacta tcactactgg     300
ttctccgatc acttactcta cttacggtaa attcctggct gacggtggtt gctctggtgg     360
tgcttacgat atcatcatct gcgacgaatg ccactctact gacgctactt ctatcctggg     420
tatcggtacc gttctggacc aggctgaaac tgcaggtgct cgtctggttg ttctggctac     480
tgctactccg ccgggttctg ttactgttcc gcacccgaac atcgaagaag ttgctctgtc     540
gactactggt gaaatcccgt tctacggtaa agctatcccg ctcgaggtta tcaaggtgg      600 tcgtcacctg attttctgcc actctaaaaa aaaatgcgac gaactggctg ctaagcttgt     660
tgctctgggt atcaacgctg ttgcttacta ccgtggtctg gacgtttctg ttatcccgac     720

```
ttctggtgac gttgttgttg tggccactga cgctctgatg actggttaca ctggtgactt      780
cgactctgtt atcgattgca acacttgcaa ttccatgtct accaacccga accgcagaa      840 aaaaaacaaa cgtaacacca accgtcgtcc gcaggacgtt aaattcccgg gtggtggtca      900
gatcgtttac ctgctgccgc gtcgtggtcc gcgtctgggt gttacgcgta aaacctctga      960
acgttctcag ccgcgtgggc gtcgtcagcc gatcccgaaa gctcgtcgtc cggaaggtcg     1020
tacctgggct cagccgggtt acccgtgccg ctgtacggt  aacgaaggtt gcggttgggc     1080
tggttggcta ctgtctccgt aataaggatc c                                    1111
```

<210> SEQ ID NO 32
<211> LENGTH: 364
<212> TYPE: PRT
<213> ORGANISM: Hepatitis C Virus
<220> FEATURE:
<223> OTHER INFORMATION: p9MB-31

<400> SEQUENCE: 32

```
Met Ala Val Asp Phe Ile Pro Val Glu Asn Leu Glu Thr Thr Met Arg
  1               5                  10                  15

Ser Pro Val Phe Thr Asp Asn Ser Ser Pro Val Val Pro Gln Ser
             20                  25                  30

Phe Gln Val Ala His Leu His Ala Pro Thr Gly Ser Gly Lys Ser Thr
         35                  40                  45

Lys Val Pro Ala Ala Tyr Ala Ala Gln Gly Tyr Lys Val Leu Val Leu
     50                  55                  60

Asn Pro Ser Val Ala Ala Thr Leu Gly Phe Gly Ala Tyr Met Ser Lys
 65                  70                  75                  80

Ala His Gly Ile Asp Pro Asn Ile Arg Thr Gly Val Arg Thr Ile Thr
                 85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255

Asp Phe Asp Ser Val Ile Asp Cys Asn Thr Cys Asn Ser Met Ser Thr
            260                 265                 270

Asn Pro Lys Pro Gln Lys Lys Asn Lys Arg Asn Thr Asn Arg Arg Pro
        275                 280                 285

Gln Asp Val Lys Phe Pro Gly Gly Gly Gln Ile Val Tyr Leu Leu Pro
```

```
             290                 295                 300
Arg Arg Gly Pro Arg Leu Gly Val Thr Arg Lys Thr Ser Glu Arg Ser
305                 310                 315                 320

Gln Pro Arg Gly Arg Arg Gln Pro Ile Pro Lys Ala Arg Arg Pro Glu
                325                 330                 335

Gly Arg Thr Trp Ala Gln Pro Gly Tyr Pro Trp Pro Leu Tyr Gly Asn
            340                 345                 350

Glu Gly Cys Gly Trp Ala Gly Trp Leu Leu Ser Pro
            355                 360
```

<210> SEQ ID NO 33
<211> LENGTH: 52
<212> TYPE: DNA
<213> ORGANISM: Artificial Sequence
<220> FEATURE:
<223> OTHER INFORMATION: Primer

<400> SEQUENCE: 33

```
acccagacgc ggaccacgac gcggcagcag gtaaacgatc tgaccaccac cc          52
```

<210> SEQ ID NO 34
<211> LENGTH: 54
<212> TYPE: DNA
<213> ORGANISM: Artificial Sequence
<220> FEATURE:
<223> OTHER INFORMATION: Primer

<400> SEQUENCE: 34

```
ccgcgtcgtg gtccgcgtct gggtgttacg cgtaaaacct ctgaacgttc tcag        54
```

<210> SEQ ID NO 35
<211> LENGTH: 1105
<212> TYPE: DNA
<213> ORGANISM: Hepatitis A Virus
<220> FEATURE:
<223> OTHER INFORMATION: p9MB-24

<400> SEQUENCE: 35

```
gaattccatg gctgttgact ttatcccggt tgaaaatctc gagactacta tgcgttctcc     60
ggttttcact gacaactctt ctccgccggt tgttccgcag tctttccagg ttgctcacct    120
gcatgctccg actggttctg gtaaatctac taaagttcca gctgcttacg ctgctcaggg    180
ttacaaagtt ctggttctga acccgtctgt tgctgctact ctgggtttcg gcgcctacat    240
gtctaaagct cacggtatcg acccgaacat tcgtactggt gtacgtacta tcactactgg    300
ttctccgatc acttactcta cttacggtaa attcctggct gacggtggtt gctctggtgg    360
tgcttacgat atcatcatct gcgacgaatg ccactctact gacgctactt ctatcctggg    420
tatcggtacc gttctggacc aggctgaaac tgcaggtgct cgtctggttg ttctggctac    480
tgctactccg ccgggttctg ttactgttcc gcacccgaac atcgaagaag ttgctctgtc    540
gactactggt gaaatcccgt tctacggtaa agctatcccg ctcgaggtta tcaaaggtgg    600
tcgtcacctg attttctgcc actctaaaaa aaaatgcgac gaactggctg ctaagcttgt    660
tgctctgggt atcaacgctg ttgcttacta ccgtggtctg gacgtttctg ttatcccgac    720
ttctggtgac gttgttgttg tggccactga cgctctgatg actggttaca ctggtgactt    780
cgactctgtt atcgattgca acacttgcaa ttccatgtct accaacccga aaccgcagaa    840
aaaaaacaaa cgtaacacca accgtcgtcc gcaggacgtt aaattcccgg gtggtggtca    900
gatcgttggt ctgctgccgc gtcgtggtcc gcgtctgggt cgtaaaacct ctgaacgttc    960
```

-continued

```
tcagccgcgt gggcgtcgtc agccgatccc gaaagctcgt cgtccggaag gtcgtacctg    1020
ggctcagccg ggttacccgt ggccgctgta cggtaacgaa ggttgcggtt gggctggttg    1080
gctgctgtct ccgtaataag gatcc                                          1105
```

<210> SEQ ID NO 36
<211> LENGTH: 358
<212> TYPE: PRT
<213> ORGANISM: Hepatitis C Virus
<220> FEATURE:
<223> OTHER INFORMATION: p9MB-24

```
Trp Ala Gln Pro Gly Tyr Pro Trp Pro Leu Tyr Gly Asn Gly Trp Ala
            340                 345                 350

Gly Trp Leu Leu Ser Pro
        355
```

<210> SEQ ID NO 37
<211> LENGTH: 1120
<212> TYPE: DNA
<213> ORGANISM: Hepatitis C Virus
<220> FEATURE:
<223> OTHER INFORMATION: p9MB-25

<400> SEQUENCE: 37

```
gaattccatg gctgttgact ttatcccggt tgaaaatctc gagactacta tgcgttctcc      60
ggttttcact gacaactctt ctccgccggt tgttccgcag tctttccagg ttgctcacct     120
gcatgctccg actggttctg gtaaatctac taaagttcca gctgcttacg ctgctcaggg     180
ttacaaagtt ctggttctga acccgtctgt tgctgctact ctgggtttcg gcgcctacat     240
gtctaaagct cacggtatcg acccgaacat tcgtactggt gtacgtacta tcactactgg     300
ttctccgatc acttactcta cttacggtaa attcctggct gacggtggtt gctctggtgg     360
tgcttacgat atcatcatct gcgacgaatg ccactctact gacgctactt ctatcctggg     420
tatcggtacc gttctggacc aggctgaaac tgcaggtgct cgtctggttg ttctggctac     480
tgctactccg ccgggttctg ttactgttcc gcacccgaac atcgaagaag ttgctctgtc     540
gactactggt gaaatcccgt tctacggtaa agctatcccg ctcgaggtta tcaaaggtgg     600
tcgtcacctg attttctgcc actctaaaaa aaaatgcgac gaactggctg ctaagcttgt     660
tgctctgggt atcaacgctg ttgcttacta ccgtggtctg gacgtttctg ttatcccgac     720
ttctggtgac gttgttgttg tggccactga cgctctgatg actggttaca ctggtgactt     780
cgactctgtt atcgattgca acacttgcaa ttccggtggt ggtggttcta tgtctaccaa     840
cccgaaaccg cagaaaaaaa acaaacgtaa caccaaccgt cgtccgcagg acgttaaatt     900
cccgggtggt ggtcagatcg ttggtctgct gccgcgtcgt ggtccgcgtc tgggtcgtaa     960
aacctctgaa cgttctcagc cgcgtgggcg tcgtcagccg atcccgaaag ctcgtcgtcc    1020
ggaaggtcgt acctgggctc agccgggtta cccgtggccg ctgtacggta acgaaggttg    1080
cggttgggct ggttggctgc tgtctccgta ataaggatcc                          1120
```

<210> SEQ ID NO 38
<211> LENGTH: 367
<212> TYPE: PRT
<213> ORGANISM: Hepatitis C Virus
<220> FEATURE:
<223> OTHER INFORMATION: p9MB-25

<400> SEQUENCE: 38

```
Met Ala Val Asp Phe Ile Pro Val Glu Asn Leu Glu Thr Thr Met Arg
 1               5                  10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80
```

Ala His Gly Ile Asp Pro Asn Ile Arg Thr Gly Val Arg Thr Ile Thr
            85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Cys Asp Glu Cys
            115                 120             125

His Ser Thr Asp Ala Thr Ser Ile Leu Gly Ile Gly Thr Val Leu Asp
            130                 135             140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
            165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
            195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Val Ala Thr Asp Ala Leu Met Thr Gly Tyr Thr Gly
                245                 250                 255

Asp Phe Asp Ser Val Ile Asp Cys Asn Thr Cys Asn Ser Gly Gly Gly
            260                 265                 270

Gly Ser Met Ser Thr Asn Pro Lys Pro Gln Lys Lys Asn Lys Arg Asn
            275                 280                 285

Thr Asn Arg Arg Pro Gln Asp Val Lys Phe Pro Gly Gly Gly Gln Ile
    290                 295                 300

Val Gly Leu Leu Pro Arg Arg Gly Pro Arg Leu Gly Arg Lys Thr Ser
305                 310                 315                 320

Glu Arg Ser Gln Pro Arg Gly Arg Arg Gln Pro Ile Pro Lys Ala Arg
            325                 330                 335

Arg Pro Glu Gly Arg Thr Trp Ala Gln Pro Gly Tyr Pro Trp Pro Leu
            340                 345                 350

Tyr Gly Asn Glu Gly Cys Gly Trp Ala Gly Trp Leu Leu Ser Pro
            355                 360                 365

<210> SEQ ID NO 39
<211> LENGTH: 1084
<212> TYPE: DNA
<213> ORGANISM: Hepatitis C Virus
<220> FEATURE:
<223> OTHER INFORMATION: p9MB-26

<400> SEQUENCE: 39
gaattccatg gctgttgact ttatcccggt tgaaaatctc gagactacta tgcgttctcc      60
ggttttcact gacaactctt ctccgccggt tgttccgcag tctttccagg ttgctcacct     120
gcatgctccg actggttctg gtaaatctac taaagttcca gctgcttacg ctgctcaggg     180
ttacaaagtt ctggttctga acccgtctgt tgctgctact ctgggtttcg gcgcctacat     240
gtctaaagct cacggtatcg acccgaacat tcgtactggt gtacgtacta tcactactgg     300
ttctccgatc acttactcta cttacggtaa attcctggct gacggtggtt gctctggtgg     360
tgcttacgat atcatcatct gcgacgaatg ccactctact gacgctactt ctatcctggg     420

-continued

```
tatcggtacc gttctggacc aggctgaaac tgcaggtgct cgtctggttg ttctggctac    480
tgctactccg ccgggttctg ttactgttcc gcacccgaac atcgaagaag ttgctctgtc    540
gactactggt gaaatcccgt tctacggtaa agctatcccg ctcgaggtta tcaaaggtgg    600
tcgtcacctg attttctgcc actctaaaaa aaaatgcgac gaactggctg ctaagcttgt    660
tgctctgggt atcaacgctg ttgcttacta ccgtggtctg gacgtttctg ttatcccgac    720
ttctggtgac gttgttgttg tggccactga cgctctgatg actggttaca ctggtgactt    780
cgactctgtt atcgattgca acacttgcaa ttccggtggt ggtggttcta tgtctaccaa    840
cccgaaaccg cagaaaaaaa acaaacgtaa caccaaccgt cgtccgcagg acgttaaatt    900
cccgggtggt ggtcagatcg ttaaaacctc tgaacgttct cagccgcgtg ggcgtcgtca    960
gccgatcccg aaagctcgtc gtccggaagg tcgtacctgg gctcagccgg ttacccgtg   1020 gccgctgtac ggtaacgaag ttgcggttg ggctggttgg ctgctgtctc cgtaataagg   1080
atcc                                                               1084
```

<210> SEQ ID NO 40
<211> LENGTH: 355
<212> TYPE: PRT
<213> ORGANISM: Hepatitis C Virus
<220> FEATURE:
<223> OTHER INFORMATION: p9MB-26

<400> SEQUENCE: 40

```
Met Ala Val Asp Phe Ile Pro Val Glu Asn Leu Glu Thr Thr Met Arg
 1               5                  10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240
```

-continued

```
Asp Val Val Val Ala Thr Asp Ala Leu Met Thr Gly Tyr Thr Gly
            245                 250                 255

Asp Phe Asp Ser Val Ile Asp Cys Asn Thr Cys Asn Ser Gly Gly
            260                 265                 270

Gly Ser Met Ser Thr Asn Pro Lys Pro Gln Lys Asn Lys Arg Asn
            275                 280                 285

Thr Asn Arg Arg Pro Gln Asp Val Lys Phe Pro Gly Gly Gln Ile
            290                 295                 300

Val Lys Thr Ser Glu Arg Ser Gln Pro Arg Gly Arg Arg Gln Pro Ile
305                 310                 315                 320

Pro Lys Ala Arg Arg Pro Glu Gly Arg Thr Trp Ala Gln Pro Gly Tyr
                325                 330                 335

Pro Trp Pro Leu Tyr Gly Asn Glu Gly Cys Gly Trp Ala Gly Trp Leu
                340                 345                 350

Leu Ser Pro
        355
```

<210> SEQ ID NO 41
<211> LENGTH: 39
<212> TYPE: PRT
<213> ORGANISM: Hepatitis C Virus
<220> FEATURE:
<223> OTHER INFORMATION: ALAM-16

<400> SEQUENCE: 41

```
Lys Thr Lys Arg Asn Thr Asn Arg Arg Pro Gln Asp Val Lys Phe Pro
1               5                   10                  15

Gly Gly Gly Gln Ile Val Tyr Leu Leu Pro Arg Arg Gly Pro Arg Leu
            20                  25                  30

Gly Val Thr Arg Lys Thr Ser
        35
```

<210> SEQ ID NO 42
<211> LENGTH: 44
<212> TYPE: PRT
<213> ORGANISM: Hepatitis C Virus
<220> FEATURE:
<223> OTHER INFORMATION: ALAM-17

<400> SEQUENCE: 42

```
Lys Thr Lys Arg Asn Thr Asn Arg Arg Pro Gln Asp Val Lys Phe Pro
1               5                   10                  15

Gly Gly Gly Gln Ile Val Gly Gly Val Tyr Leu Leu Pro Arg Arg Gly
            20                  25                  30

Pro Arg Leu Gly Val Arg Ala Thr Arg Lys Thr Ser
        35                  40
```

<210> SEQ ID NO 43
<211> LENGTH: 25
<212> TYPE: PRT
<213> ORGANISM: Hepatitis C Virus
<220> FEATURE:
<223> OTHER INFORMATION: ALAM-18

<400> SEQUENCE: 43

```
Lys Thr Lys Arg Asn Thr Asn Arg Arg Pro Gln Asp Val Lys Phe Pro
1               5                   10                  15

Gly Gly Gly Gln Ile Val Lys Thr Ser
            20                  25
```

```
<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
gatcgctcga attcctcg                                                 18

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cgaggaattc gagcgatctt                                               20

<210> SEQ ID NO 46
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 46

Met Ser Thr Asn Pro Lys Pro Gln Lys Asn Lys Arg Asn Thr Asn
 1               5                  10                  15

Arg Arg

<210> SEQ ID NO 47
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 47

Asn Lys Arg Asn Thr Asn Arg Arg Pro Gln Asp Val Lys Phe Pro Gly
 1               5                  10                  15

Gly Gly

<210> SEQ ID NO 48
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 48

Asp Val Lys Phe Pro Gly Gly Gly Gln Ile Val Gly Gly Val Tyr Leu
 1               5                  10                  15

Leu Pro

<210> SEQ ID NO 49
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 49

Val Gly Gly Val Tyr Leu Leu Pro Arg Arg Gly Pro Arg Leu Gly Val
```

```
                  1               5                  10                  15
Arg Ala

<210> SEQ ID NO 50
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 50

Gly Pro Arg Leu Gly Val Arg Ala Thr Arg Lys Thr Ser Glu Arg Ser
  1               5                  10                  15

Gln Pro

<210> SEQ ID NO 51
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 51

Lys Thr Ser Glu Arg Ser Gln Pro Arg Gly Arg Arg Gln Pro Ile Pro
  1               5                  10                  15

Lys Ala

<210> SEQ ID NO 52
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 52

Arg Arg Gln Pro Ile Pro Lys Ala Arg Arg Pro Glu Gly Arg Thr Trp
  1               5                  10                  15

Ala Gln

<210> SEQ ID NO 53
<211> LENGTH: 18
<212> TYPE: PRT
<213> ORGANISM: Artificial Sequence
<220> FEATURE:
<223> OTHER INFORMATION: HCV-Core derived peptides

<400> SEQUENCE: 53

Pro Glu Gly Arg Thr Trp Ala Gln Pro Gly Tyr Pro Trp Pro Leu Tyr
  1               5                  10                  15

Gly Asn

<210> SEQ ID NO 54
<211> LENGTH: 19
<212> TYPE: PRT
<213> ORGANISM: Artificial Sequence
<220> FEATURE:
<223> OTHER INFORMATION: HCV-Core derived peptides

<400> SEQUENCE: 54

Gln Tyr Pro Trp Pro Leu Tyr Gly Asn Glu Gly Cys Gly Trp Ala Gly
  1               5                  10                  15

Trp Leu Leu
```

```
<210> SEQ ID NO 55
<211> LENGTH: 17
<212> TYPE: PRT
<213> ORGANISM: Artificial Sequence
<220> FEATURE:
<223> OTHER INFORMATION: HCV-Core derived peptides

<400> SEQUENCE: 55

Cys Gly Trp Ala Gly Trp Leu Leu Ser Pro Arg Gly Ser Arg Pro Ser
 1               5                  10                  15

Trp

<210> SEQ ID NO 56
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 56

Trp Leu Leu Ser Pro Arg Gly Ser Arg Pro Ser Trp Gly Pro Thr Asp
 1               5                  10                  15

Pro Arg Arg Arg Ser Arg Asn Leu Gly
             20                  25

<210> SEQ ID NO 57
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 57

Ser Trp Gly Pro Thr Asp Pro Arg Arg Arg Ser Arg Asn Leu Gly Lys
 1               5                  10                  15

Val Ile Asp Thr Leu Thr Cys Gly Phe
             20                  25

<210> SEQ ID NO 58
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 58

Ser Arg Asn Leu Gly Lys Val Ile Asp Thr Leu Thr Cys Gly Phe Ala
 1               5                  10                  15

Asp Leu Met Gly Tyr Ile Pro Leu Val
             20                  25

<210> SEQ ID NO 59
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 59

Leu Thr Cys Gly Phe Ala Asp Leu Met Gly Tyr Ile Pro Leu Val Gly
 1               5                  10                  15

Ala Pro Leu Gly Gly Ala Ala Arg Ala
             20                  25
```

```
<210> SEQ ID NO 60
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 60

Tyr Ile Pro Leu Val Gly Ala Pro Leu Gly Gly Ala Ala Arg Ala Leu
 1               5                  10                  15

Ala His Gly Val Arg Val Leu Glu Asp
            20                  25

<210> SEQ ID NO 61
<211> LENGTH: 25
<212> TYPE: PRT
<213> ORGANISM: Artificial Sequence
<220> FEATURE:
<223> OTHER INFORMATION: HCV-Core derived peptides

<400> SEQUENCE: 61

Gly Ala Ala Arg Ala Leu Ala His Gly Val Arg Val Leu Glu Asp Gly
 1               5                  10                  15

Val Asn Tyr Ala Thr Gly Asn Leu Pro
            20                  25

<210> SEQ ID NO 62
<211> LENGTH: 23
<212> TYPE: PRT
<213> ORGANISM: Artificial Sequence
<220> FEATURE:
<223> OTHER INFORMATION: HCV-Core derived peptides

<400> SEQUENCE: 62

Leu Glu Asp Gly Val Asn Tyr Ala Thr Gly Asn Leu Pro Gly Cys Ser
 1               5                  10                  15

Phe Ser Ile Phe Leu Leu Ala
            20

<210> SEQ ID NO 63
<211> LENGTH: 23
<212> TYPE: PRT
<213> ORGANISM: Artificial Sequence
<220> FEATURE:
<223> OTHER INFORMATION: HCV-Core derived peptides

<400> SEQUENCE: 63

Leu Pro Gly Cys Ser Phe Ser Ile Phe Leu Leu Ala Leu Leu Ser Cys
 1               5                  10                  15

Leu Thr Val Pro Ala Ser Ala
            20
```

METHODS FOR THE SIMULTANEOUS DETECTION OF HCV ANTIGENS AND HCV ANTIBODIES

The subject application is a divisional of U.S. patent application Ser. No. 10/173,480, filed on Jun. 17, 2002, now U.S. Pat. No. 6,727,092, which is a Continuation-In-Part of U.S. patent application Ser. No. 09/891,983, filed on Jun. 26, 2001, both of which are hereby incorporated in their entirety by reference.

BACKGROUND OF THE INVENTION

1. Technical Field

The subject invention relates to methods for the simultaneous detection of Hepatitis C Virus (HCV) antigens as well as antibodies produced in response to HCV antigens. Furthermore, the subject invention allows one to detect antigens in the early, acute stage of infection, even prior to the development of antibodies, thereby allowing for early detection of infected blood and blood products, and thus improving the safety of the blood supply.

2. Background Information

Recent epidemiological studies indicate that HCV infects more than 170 million people worldwide and that, in more than 50% of the cases, the infection is chronic. In the United States, there are approximately 4 million people infected, and 30,000 new infections are estimated to occur annually (NIH Conference, *Hepatology Suppl* 1:2S (1997)). In addition, HCV is responsible for 8,000–10,000 deaths annually in the United States and is the leading indicator for liver transplantation.

The HCV genome is a single-stranded RNA molecule of positive polarity that is approximately 9400–9500 nucleotides in length. The organization of the coding regions resembles that of other flaviviruses [Major et al., *Hepatology* 25:1527 (1997)] as well as the more recently discovered GB viruses [Muerhoff A S, et al., *J Virol* 69:5621 (1995)]. The HCV genome possesses a large open reading frame (ORF) encoding a polyprotein precursor of 3010 to 3033 amino acids depending on the particular isolate [Choo et al., Proc Natl Acad Sci USA 88:2451 (1991); Grakoui et al., J Virol 67:1385 (1993)]. HCV structural genes (core and envelope) are encoded near the 5'-end of the genome, followed by the proteases and helicase, the helicase cofactor and the replicase. Noncoding regions (NCR), thought to be important in replication, are found at each end of the genome.

HCV infection occurs primarily through parenteral exposure, i.e., through shared needles, by tattooing, or through transfusion of contaminated blood or blood products. Following exposure, the virus enters a susceptible hepatocyte and viral replication occurs. There is an eclipse phase period of approximately 10 days during which time there is no evidence of viral presence (i.e., viral RNA cannot be detected), serum transaminase levels are within normal limits, and there is no evidence of an immune response to HCV [Busch et al., *Transfusion* 40:143 (2000)]. Typically, about 10 days following exposure, HCV RNA can be detected, often with viral loads between 100,000–120,000,000 HCV RNA copies per ml of serum. Several weeks later, there is typically an increase in ALT levels indicating inflammation of the liver; antibodies are detected an average of about 70 days after exposure.

One of the preventive measures employed to limit the spread of HCV infections is to screen blood for exposure to HCV, either by the detection of antibodies to HCV or by the detection of viral-specific molecules (e.g., HCV RNA or HCV core proteins) in serum/plasma. Blood or blood products derived from individuals identified as having been exposed to HCV, by these tests, are removed from the blood supply and are not utilized for distribution to recipients of blood products (see, e.g., U.S. Pat. No. 6,172,189). These tests may also be utilized in the clinical setting to diagnose liver disease attributable to HCV infection.

Due to the unavailability of native, intact HCV virions, serologic antibody tests have relied on recombinant antigens or synthetic peptides, representing selected fragments of the viral polyprotein. The first generation anti-HCV screening tests were based on detection of antibodies directed against a recombinant protein (HCV genotype 1a) originating from sequences located in the nonstructural NS-4 protein (C100-3) [Choo et al., *Science* 244:359 (1989); Kuo et al., *Science* 244:362 (1989)]. The first generation assays failed to detect antibodies in approximately 10% of individuals having chronic HCV infection and up to 10–30% of individuals presenting with acute HCV infection. The second generation anti-HCV assays have incorporated recombinant proteins from three different regions of the HCV genome (HCV genotype 1a), including amino acid sequences from the core, NS3, and NS4 protein [Mimms et al., *Lancet* 336:1590 (1990); Bresters et al., *Vox Sang* 62:213 (1992)], allowing a marked improvement over the first generation tests in identifying HCV infected blood donors [Aach et al., *N Engl J Med* 325:1325 (1991); Kleinman et al., *Transfusion* 32:805 (1992)]. The second generation assays detect antibodies in close to 100% of chronic HCV cases [Hino K., *Intervirology* 37:77 (1994)] and in nearly 100% of the acute cases by 12 weeks post infection [Alter et al., *N Engl J Med* 327:1899 (1992); Bresters et al., *Vox Sang* 62:213 (1992)]. The third generation test includes a recombinant protein expressing amino acid sequences from the NS5 region, as well as antigens from the core, NS3 and NS4. Some studies have indicated a slight improvement in sensitivity in comparing the third generation tests to second generation tests [Lee et al., *Transfusion* 35:845 (1995); Courouce et al. *Transfusion* 34:790–795 (1994)], but this improvement is largely attributed to changes in the NS3 protein rather than the inclusion of NS5 [Courouce et al., *Lancet* 343:853 (1994)].

In general, the second and third generation HCV antibody tests detect exposure to HCV about 70 days after exposure. Since HCV establishes persistent, and in many cases lifelong infection, the detection of antibodies to HCV represents a very efficient method for determining exposure to HCV. However, antibody testing alone will frequently fail to detect HCV infected individuals during the first 70 days after exposure.

The existing HCV antigen tests rely on detecting the presence of the HCV core antigen in serum or plasma. The core (or nucleocapsid) protein comprises the first 191 amino acids of the polyprotein. Two different types of serologic assays have been developed which permit detection of HCV core antigens in serum. One assay format detects HCV core antigens in subjects prior to seroconversion and is utilized in screening blood donors, while the other assay format detects core antigens only in hepatitis C patients, regardless of their HCV antibody status and is utilized in clinical laboratories to diagnose exposure to HCV or to monitor antiviral therapy.

Recent data on samples obtained during the pre-seroconversion period indicate that the HCV antigen test detects exposure to HCV significantly earlier than antibody testing [Aoyagi et al., *J Clin Microbiol* 37:1802 (1999); Peterson et al., *Vox Sang* 78:80(2000); Dawson et al., *Transfusion*, SD161, 40(2000); Muerhoff et al., 7th *International Meeting on Hepatitis C virus and related viruses*, Dec.

3–7, 2000], and represents an alternative to nucleic acid testing for detecting exposure to HCV during the pre-seroconversion period. The advantages of HCV antigen detection are that the test is rapid, simple, may-not require sample extraction or other pretreatment, and is not as prone to handling errors (e.g., contamination) as may occur in the HCV RNA tests.

In clinical laboratories, the HCV antigen test has comparable sensitivity to the HCV DNA tests in detecting exposure to HCV in patients infected with different HCV genotypes [Dickson et al., *Transplantation* 68:1512 (1999)] and in monitoring antiviral therapy [Tanaka et al., *Hepatology* 32:388 (2000); Tanaka et al., *J Hepatol* 23:742 (1995)]. Thus, HCV core antigen tests present a practical alternative to HCV RNA for screening blood donors or for monitoring antiviral therapy.

The uniqueness of the current invention lies in its ability to detect HCV antibodies and HCV antigens simultaneously (see also International Application No. PCT/JP99/04129). This combination test or "combo" assay utilizes antigen detection to identify exposure to HCV during the pre-seroconversion "window period" and antibody detection to identify exposure to HCV after seroconversion.

All U.S. patents and publications referred to herein are hereby incorporated in their entirety by reference.

SUMMARY OF THE INVENTION

The subject invention encompasses a method of simutaneously detecting at least one Hepatitis C Virus (HCV) antigen and at least one HCV antibody in a test sample comprising the steps of: a) contacting the test sample with: 1) at least one HCV viral antigen or portion thereof coated on a solid phase (e.g., a microparticle), for a time and under conditions sufficient for the formation of antibody/antigen complexes and 2) at least one antibody to HCV or portion thereof coated on the solid phase, for a time and under conditions sufficient for the formation of antigen/antibody complexes; b) detecting the antibody/antigen complexes, presence of the complexes indicating presence of at least one HCV antigen in the test sample; and c) detecting the antigen/antibody complexes, presence of the complexes indicating presence of at least one HCV antibody in the test sample. The at least one HCV antigen coated on the solid phase may be, for example, core antigen, NS3, NS4, NS5, and portions (or fragments) thereof. The at least one antibody coated on the solid phase may be, for example, a monoclonal antibody selected from the group consisting of 13-959-270, 14-1269-281, 14-1287-252, 14-153-234, 14-153-462, 14-1705-225, 14-1708-269, 14-1708-403, 14-178-125, 14-188-104, 14-283-112, 14-635-225, 14-726-217, 14-886-216, 14-947-104, 14-945-218, 107-35-54, 110-81-17, 13-975-157, 14-1350-210, C11-3, C11-7, C11-10, C11-14 and C11-15. Further, the at least one monoclonal antibody coated on the solid phase preferably is not reactive with the at least one antigen coated on the solid phase. In particular, the at least one monoclonal antibody may be a HCV anti-core monoclonal antibody and the at least one antigen may be a recombinant HCV core protein. The recombinant core protein does not contain epitopes to which the anti-core monoclonal antibody binds.

Additionally, the present invention includes a method for simultaneously detecting the presence of at least one HCV antigen and at least one HCV antibody in a test sample comprising the steps of: a) contacting the test sample with: 1) at least one HCV viral antigen or portion thereof coated on a solid phase, wherein the solid phase is, for example, a microparticle, for a time and under conditions sufficient for the formation of antibody/antigen complexes and 2) at least one HCV antibody or portion thereof coated on the solid phase, for a time and under conditions sufficient for the formation of antigen/antibody complexes; b) adding a first conjugate to the resulting antibody/antigen complexes for a time and under conditions sufficient to allow the conjugate to bind to the bound antibody in (a) (1), wherein the conjugate comprises a second antibody (e.g., mouse anti-human IgG) attached to a label (for example, a chemiluminescent compound) capable of generating a detectable signal and simultaneously adding a second conjugate to the resulting antigen/antibody complexes for a time and under conditions sufficient to allow said second conjugate to bind to the bound antigen in (a) (2), wherein said second conjugate comprises a third antibody (e.g., a monoclonal antibody to anti-HCV core antigen such as C11-10) attached to the label, for example, chemiluminescent compound, capable of generating a detectable signal; and b) detecting the presence of the generated signal, presence of the signal indicating the presence of at least one HCV antigen or at least one HCV antigen in the test sample. Again, the at least one HCV antigen coated on the solid phase may be selected from the group consisting of core antigen, NS3, NS4, NS5, and portions thereof. Further, the at least one antibody coated on the solid phase may be a monoclonal antibody selected from the group consisting of, for example, 13-959-270, 14-1269-281, 14-1287-252, 14-153-234, 14-153-462, 14-1705-225, 14-1708-269, 14-1708-403, 14-178-125, 14-188-104, 14-283-112, 14-635-225, 14-726-217, 14-886-216, 14-947-104, 14-945-218, 13-975-157, 14-1350-210, 107-35-54, 110-81-17, C11-3, C11-7, C11-10, C11-14 and C11-15.

The at least one monoclonal antibody coated on the solid phase is preferably not reactive with the at least one antigen coated on the solid phase.

Also, the present invention encompasses a kit comprising: a) a container containing at least one HCV antigen coated on a solid phase, wherein the solid phase is, for example, a microparticle; and b) a container containing at least one HCV antibody coated on a solid phase, wherein the solid phase is preferably a microparticle.

The present invention also includes a kit comprising: a container containing: 1) at least one HCV antigen coated on a solid phase, wherein the solid phase is preferably a microparticle, and 2) at least one HCV antibody, coated on the solid phase. The kit may further comprise at least one conjugate comprising a signal-generating compound attached to a HCV antigen or HCV antibody. The signal-generating compound may be, for example, acridinium or an acridinium-containing compound.

Additionally, the present invention includes a method of detecting HCV antigen in a test sample comprising the steps of: a) contacting the test sample with at least one HCV antibody (e.g., monoclonal) coated on a solid phase, wherein the solid phase is a microparticle, for a time and under conditions sufficient for the formation of antibody/antigen complexes; and b) detecting the presence of antibody/antigen complexes, presence of the complexes indicating presence of antigen in the test sample.

The invention also encompasses a method of detecting HCV antigen in a test sample comprising the steps of: a) contacting the test sample with at least one HCV antibody (e.g., monoclonal) coated on a solid phase, wherein the solid phase is, preferably, a microparticle, for a time and under conditions sufficient for the formation of antibody/antigen complexes; b) adding a conjugate to the resulting antibody/antigen complexes for a time and under conditions sufficient to allow the conjugate to bind to the bound at least one antibody, wherein the conjugate comprises a second antibody attached to a label, for example, a chemiluminescent compound capable of generating a detectable signal; and c) detecting the signal generated by the label, for example, chemiluminescent compound, a signal generated by the label indicating the presence of antigen in the test sample.

Also, the present invention includes a recombinant protein comprising an amino acid sequence selected from the group consisting of, for example, SEQ ID NO:6, SEQ ID NO:8, SEQ ID NO:12 and SEQ ID NO:16 as well as an amino acid sequence comprising conservative amino acid substitutions of these sequences. (A conservative substitution is defined as one or more amino acid substitutions in a sequence which do not change the function of the sequence.) The present invention also includes a recombinant protein comprising an amino acid sequence encoded by a nucleotide sequence selected from the group consisting of, for example, SEQ ID NO:5, SEQ ID NO:7, SEQ ID NO:11 and SEQ ID NO:15.

(Substitutions, deletions and additions within the sequences which do not affect functionally affect the protein encoded by the sequence are also considered to be within the scope of the present invention.)

Additionally, the present invention includes a vector or construct comprising a nucleotide sequence selected from the group consisting of, for example, SEQ ID NO:5, SEQ ID NO:7, SEQ ID NO:11 and SEQ ID NO:15. The invention also includes a host cell comprising the vector or construct.

Furthermore, the present invention includes an immunoassay which may simultaneously detect at least one HCV antigen or at least one HCV antibody in a test sample.

BRIEF DESCRIPTION OF THE DRAWINGS

FIG. 4 lists all of the nucleotide and amino acid sequences referred to herein as well as the corresponding sequence identifier numbers.

DETAILED DESCRIPTION OF THE INVENTION

Figure 1:
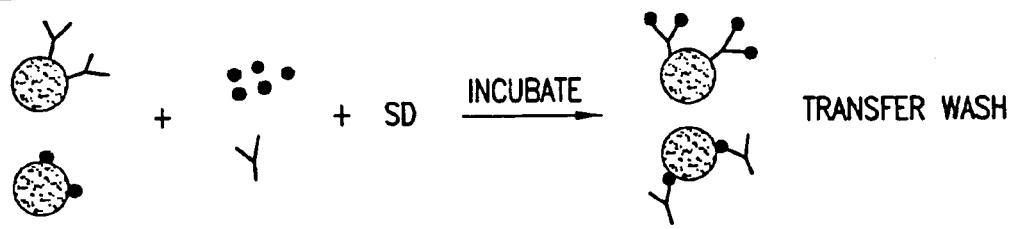
FIG. 1 illustrates the Abbott PRISM® HCV Ab assay format. The assay uses a 2-step format that consists of microparticles coated with recombinant HCV antigens from the core, NS3, NS4 and NS5 regions of the HCV genome. These microparticles, when combined with the donor specimen, a diluent, and a complex of goat polyclonal anti-human F(ab')$_2$ fragment/murine monoclonal anti-biotin:Acridinium conjugate yield an amount of photons representing a qualitative measurement of anti-HCV antibodies in the specimen when triggered with the PRISM® Activator solution.
Figure 1:
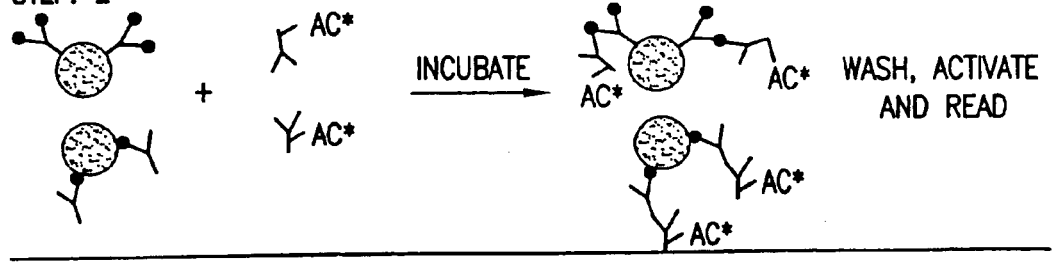

The subject invention relates to various methods which may be utilized in order to simultaneously detect antigens of HCV and antibodies to HCV in a biological sample. Thus, if an individual has either developed specific antibodies to HCV and/or has HCV specific antigens in the biological sample tested, the methods of the present invention will yield a positive result. Such results may be used, for example, to diagnose the patient in terms of presence and status of infection (i.e., acute or chronic) as well as to determine the suitability of a donor blood or blood product sample for transfusion.

Also, the present invention overcomes the problems associated with the "window period" (i.e., 50–60 days post infection) wherein an individual may be infected with HCV but may not have developed antibodies yet. Such individuals may transmit HCV to others during this period. Thus, by detecting HCV during this "window period", the present invention allows for a quick diagnosis of HCV, as opposed to waiting for the development of antibodies, and prevents contamination of the blood supply.

In one embodiment of the present invention, HCV viral antigens (e.g., core, N3, N4 and N5), or portions thereof, are coated on a solid phase (or are in a liquid phase). The test or biological sample (e.g., serum, plasma, urine, etc.) is then contacted with the solid phase. If antibodies are present in the sample, such antibodies bind to the antigens on the solid phase and are then detected by either a direct or indirect method. The direct method comprises simply detecting presence of the complex itself and thus presence of the antibodies. In the indirect method, a conjugate is added to the bound antibody. The conjugate comprises a second antibody, which binds to the first bound antibody, attached to a signal-generating compound or label. Should the second antibody bind to a bound first antibody, the signal-generating compound generates a measurable signal. Such signal then indicates presence of the first antibody in the test sample.

Examples of solid phases used in diagnostic immunoassays are porous and non-porous materials, latex particles, magnetic particles, microparticles (see U.S. Pat. No. 5,705,330), beads, membranes, microtiter wells and plastic tubes. The choice of solid phase material and method of labeling the antigen or antibody present in the conjugate, if desired, are determined based upon desired assay format performance characteristics.

As noted above, the conjugate (or indicator reagent) will comprise an antibody (or perhaps anti-antibody, depending upon the assay), attached to a signal-generating compound or label. This signal-generating compound or "label" is itself detectable or may be reacted with one or more additional compounds to generate a detectable product. Examples of signal-generating compounds include chromogens, radioisotopes (e.g., 125I, 131I, 32P, 3H, 35S and 14C), chemiluminescent compounds (e.g., acridinium), particles (visible or fluorescent), nucleic acids, complexing agents, or catalysts such as enzymes (e.g., alkaline phosphatase, acid phosphatase, horseradish peroxidase, beta-galactosidase and ribonuclease). In the case of enzyme use (e.g., alkaline phosphatase or horseradish peroxidase), addition of a chromo-, fluro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

Examples of biological fluids which may be tested by the above immunoassays include plasma, urine, whole blood, dried whole blood, serum, cerebrospinal fluid, saliva, tears, nasal washes or aqueous extracts of tissues and cells.

At the same time as the antibodies are being detected, HCV antigens are also being detected; thus, the present invention obviates the need for the running of two different tests. This is accomplished by exposing the test sample to a solid phase (or liquid phase) coated with specific antibodies to HCV (e.g., human or animal monoclonal antibodies to core, polyclonal antibodies, chimeric antibodies, etc.). Antigens, if present in the sample, bind to the solid phase and may then be detected by a direct or indirect method as described above. More specifically, the indirect method involves the addition of a conjugate comprising a second antibody (which binds to the bound antigen) attached to a label or signal-generating compound. When the second antibody binds to the bound antigen, a detectable signal is then generated indicating presence of HCV antigen in the test sample.

The antibodies which are coated on the solid phase as well as the "second antibody" may be, as noted above, monoclonal antibodies or polyclonal antibodies. For example, if one chooses to utilize monoclonal antibodies, they may be selected from Abbott monoclonal antibodies 13-959-270, 14-1269-281, 14-1287-252, 14-153-234, 14-153-462, 14-1705-225, 14-1708-269, 14-1708-403, 14-178-125, 14-188-104, 14-283-112, 14-635-225, 14-726-217, 14-886-216, 14-947-104 and 14-945-218. The following anti-core monoclonal antibodies may also be utilized for purposes of the present invention: 107-35-54, 110-81-17, 13-975-157, 14-1350-210 (see U.S. Pat. No. 5,753,430) and Tonen HCV core monoclonals C11-3, 7, 10, 14 and 15 (see PCT Application WO 099/06836), all of which are available from the American Type Culture Collection, 10801 University Boulevard, Manassas, Va. 20110-2209. (For a discussion of the manner in which monoclonal antibodies may be created, see Kohler and Milstein, Nature (1975) 256:494, and reviewed in Monoclonal Hybridoma Antibodies: Techniques and Applications, ed. Hurrell (CRC Press, Inc., 1982); see also J. W. Goding in *Monoclonal Antibodies: Principles and Practice* (Academic Press, N.Y., 1983; see also U.S. Pat. No. 5,753,430).

It should be noted that HCV core protein may be one possible target of the HCV antigen portion of the assay. More specifically, the detection of the core protein is accomplished by using monoclonal antibodies directed towards epitopes within the core protein. These anti-core monoclonals are placed on the solid phase and facilitate the capture of core antigen proteins from the test sample. For detection of HCV antibodies in the test sample, recombinant HCV core protein is also placed on the solid phase. It should be noted however that there are significant problems associated with the use of a single protein as the target for an antigen test and as the capture reagent for antibody detection, namely there is significant "cross-reactivity" between the core antigen and the anti-core monoclonal antibodies coated onto the solid phase(s). This results in a false positive signal, even in the absence of the test sample, since the monoclonal antibodies will bind to epitopes present on the recombinant protein.

In order to avoid such cross-reactivity, the core protein used in the antibody detection portion of the assay may be modified such that the ability of the anti-core monoclonals to bind HCV core is eliminated. Such modification may be achieved by use of recombinant DNA technology in which the epitope region (i.e., the short sequence of amino acids needed for monoclonal antibody binding) is eliminated or modified. Thus, use of the modified recombinant core protein would consequently maintain several human epitopes to which antibodies present in the serum of infected individuals would bind; however, the anti-core monoclonal antibodies used for antigen capture would not bind the modified protein. Alternatively, one could replace the HCV core recombinant protein with polypeptides that include sequences known to bind to antibodies present in the serum of most infected individuals, but do not include sequences containing the epitopes recognized by the anti-core monoclonals used to detect HCV core antigens.

More specifically, as noted above, in order to avoid cross-reactivity, one may use core antigens for antibody detection in the assay. In particular, in the present invention, the solid phase may be coated with nonstructural proteins (NS) 3, 4 and/or 5 (i.e., NS3, NS4 and/or NS5) and/or the core protein. Alternatively, in the present invention, the solid phase may be coated with any of the above-mentioned HCV proteins, or segments or portions thereof, either individually or in combination (for antibody detection). The antigens used for coating the solid phase may be generated as a contiguous recombinant protein, expressed as recombinant proteins, either as a single entity or as discrete entities, or as synthetic peptides designed either as a single entity or discrete entities.

It should also be noted that one may also detect antibodies to HCV E2 in the combo assay. Thus, using the present assay described herein, one may replace an assay which detects anti-core antibody. Alternatively, one may supplement such an anti-core antibody assay with the antigen assay portion of the combo assay described herein. (See, e.g., U.S. Pat. No. 6,156,495 relating to detection of HGBV E2 antibody or antigen.)

With respect to detection of antigens in the present invention, as noted above, the monoclonal or polyclonal antibodies coated on the solid phase must not recognize the core antigens used on the solid phase (for antibody detection). Thus, for example, in the present invention, one may use the full antibody or a fragment thereof. (For purposes of the present invention, a "fragment" or "portion" of an antibody is defined as a subunit of the antibody which reacts in the same manner, functionally, as the full antibody with respect to binding properties.)

Additionally, it should also be noted that the initial capture antibody (for detecting HCV antigens) used in the immunoassay may be covalently or non-covalently (e.g., ionic, hydrophobic, etc.) attached to the solid phase. Linking agents for covalent attachment are known in the art and may be part of the solid phase or derivatized to it prior to coating.

The second manner in which to use the solid phase for detecting HCV antibodies involves elimination of the core antigens entirely. For example, the solid phase is coated with NS3, NS4 and/or NS5 and a substitute for the core protein or regions thereof (e.g., E2). In contrast, the antibodies coated on the solid phase for detection of antigen are directed against the core protein of HCV.

Other assay formats which may be used for purposes of the present invention, in order to simultaneously detect antigens and antibodies include, for example, Dual assay strip blots, a rapid test, a Western blot, as well as the use of paramagnetic particles in, for example, an Architect® assay (Frank Quinn, The Immunoassay Handbook, Second edition, edited by David Wild, pages 363–367, 2001). Such formats are known to those of ordinary skill in the art.

It should also be noted that the assays of the present invention may also be used to solely detect HCV antigens or HCV antibodies, rather than both, if desired. Certainly, if one desires to establish that an infection initially exists, one may simply want to determine the presence of antigen in a test sample such as during the "window period". On the other hand, if one wants to establish the stage of infection (e.g., acute versus chronic), one may wish to look for the presence of antibodies and titer thereof.

It should also be noted that the elements of the assay described above are particularly suitable for use in the form of a kit. The kit may also comprise one container such as vial, bottles or strip, with each container with a pre-set solid phase, and other containers containing the respective conjugates. These kits may also contain vials or containers of other reagents needed for performing the assay, such as washing, processing and indicator reagents.

The present invention may be illustrated by the use of the following non-limiting examples:

EXAMPLE I

Mapping of HCV Core Epitopes Recognized by Monoclonal Antibodies

To determine the region within the HCV core protein to which each of the monoclonal antibodies binds, a series of overlapping, biotinylated peptides were synthesized (Table I). These peptides were used to develop EIAs, as described below. It should be noted that all monoclonals were able to detect a recombinant HCV core fusion protein using EIA methodologies similar to that described below (data not shown).

TABLE I

HCV-Core Derived Peptides

| Peptide | Sequence | Core Region Represented |
|---|---|---|
| A | MSTNPKPQKKNKRNTNRR | 1–18 |
| B | NKRNTNRRPQDVKFPGGG | 11–28 |
| C | DVKFPGGGQIVGGVYLLP | 21–38 |
| D | VGGVYLLPRRGPRLGVRA | 31–48 |
| E | GPRLGVRATRKTSERSQP | 41–58 |
| F | KTSERSQPRGRRQPIPKA | 51–68 |
| G | RRQPIPKARRPEGRTWAQ | 61–78 |
| H | PEGRTWAQPGYPWPLYGN | 71–88 |
| I | QYPWPLYGNEGCGWAGWLL | 81–98 |
| J | CGWAGWLLSPRGSRPSW | 91–107 |
| 1 | WLLSPRGSRPSWGPTDPRRRSRNLG | 96–120 |
| 2 | SWGPTDPRRRSRNLGKVIDTLTCGF | 106–130 |
| 3 | SRNLGKVIDTLTCGFADLMGYIPLV | 116–140 |
| 4 | LTCGFADLMGYIPLVGAPLGGAARA | 126–150 |

TABLE I-continued

HCV-Core Derived Peptides

| Peptide | Sequence | Core Region Represented |
|---|---|---|
| 5 | YIPLVGAPLGGAARALAH GVRVLED | 136–160 |
| 6 | GAARALAHGVRVLEDGVNYATGNLP | 146–170 |
| 7 | LEDGVNYATGNLPGCSFSIFLLA | 158–180 |
| 8 | LPGCSFSIFLLALLSCLTVPASA | 169–191 |

Coating of polystyrene beads: One quarter-inch polystyrene beads were used as the solid phase for the peptide EIAs. Prior to coating, beads were washed with 15% isopropanol (in water) at room temperature for 30 minutes without agitation. Isopropanol was removed and the beads were rinsed once with deionized water. The washed beads were then added to a vial containing the peptide diluted to 5 µg/ml in 0.1 M sodium phosphate, pH 7.5 buffer (0.233 ml per bead). Beads were incubated at 56° C. for 2 hours with end-over-end mixing. Beads were then washed three times with PBS and then incubated in PBS containing 0.1% Triton X-100 at 40° C. for 1 hour with end-over-end mixing. They were again washed three times in PBS and then incubated at 40° C. in 5% BSA/PBS for 1 hour end-over-end mixing. Beads were washed four times with PBS and then incubated at room temperature in PBS containing 5% sucrose without mixing for 20 minutes. Sucrose buffer was removed and beads air-dried. Coated beads were stored desiccated at 4° C.

Bead coating validation: To determine whether the biotinylated peptides were actually coated onto the beads, an assay was performed in which beads were incubated in buffer containing horseradish peroxidase-labeled streptavidin (200–400 ng/ml). The beads were then washed with deionized water and substrate added. Product was detected by absorbance at 492 nm. All peptides in Table I were shown to be coated onto the polystyrene beads by this assay (data not shown).

HCV peptide EIAs: Monoclonal antibodies generated against a recombinant HCV core protein (see Example I) were tested for their ability to bind to each of peptide-coated beads as follows: monoclonals antibodies were diluted to 50 ng/ml in sample diluent buffer (Tris buffer containing 20% goat serum, 10% calf serum, 0.2% Triton X-100 and sodium azide) of which 0.2 ml was added into a reaction well containing the peptide-coated bead and incubated at room temperature for 2 hours with mixing. Beads were then washed with deionized water followed by the addition of 0.2 ml of peroxidase-labeled goat anti-mouse IgG (0.3 µg/ml). Beads were incubated at room temperature for 60 minutes with mixing. Beads were washed with deionized water, transferred into plastic tubes to which 0.3 ml of OPD (0.3% O-phenylenediamine-2-HCl in citrate buffer containing 0.02% $H_2O_2$) substrate was added, and incubated in the dark at room temperature for 30 min without mixing. Reaction was quenched by the addition of 1 ml of 1N H2SO4 and the OD at 492 nm determined. The absorbance is directly proportional to the amount of antibody bound to the bead.

Peptide mapping of monoclonals: Using the assay as described above, each of the monoclonals were assayed for their ability to bind each of the HCV-core-derived peptide coated beads. When a monoclonal antibody was found to bind to a specific peptide-coated bead, 10-fold serial dilutions of the monoclonal antibody were made which were then assayed for binding to the same peptide. This allowed the determination of binding specificity for each monoclonal antibody. Results shown in Table II indicate the lowest dilution of monoclonal antibody that exhibited binding (absorbance at least 3-times background).

TABLE II

Anti-core monoclonal peptide mapping

| Monoclonal | | A<br>aa1-18 | B<br>aa11-28 | C<br>aa21-37 | D<br>aa31-48 | E<br>aa41-57 | F<br>aa51-68 | G<br>aa61-78 | H<br>aa71-88 | I<br>aa81-98 |
|---|---|---|---|---|---|---|---|---|---|---|
| 14-1350-210 | A07 | — | — | — | — | — | — | — | — | — |
| 13-975-157 | A08 | — | — | — | — | — | — | — | — | — |
| 13-959-270 | A09 | — | — | — | — | — | — | — | — | — |
| 110-81-17 | A15 | — | — | — | — | — | — | — | — | — |
| 107-35-54 | A04 | — | — | — | — | — | — | — | — | — |
| 14-1708-269 | A269 | — | — | — | — | — | 5 ng/ml | — | — | — |
| 14-1705-255 | A10 | — | — | — | — | — | 500 pq/ml | — | — | — |
| 14-1287-252 | A12 | — | — | — | — | — | 5 ng/ml | — | — | — |
| 14-1269-281 | A03 | — | — | — | — | — | 50 ng/ml | — | — | — |
| 14-947-104 | A16 | — | — | — | — | — | 500 pq/ml | — | — | — |
| 14-945-218 | A218 | — | — | — | — | — | — | — | — | — |
| 14-886-216 | A14 | — | — | — | — | — | — | — | — | — |
| 14-726-217 | A06 | — | — | — | — | — | 50 ng/ml | — | — | — |
| 14-635-225 | A05 | — | — | — | — | — | — | — | — | — |
| 14-283-112 | A112 | — | — | — | — | — | 5 ng/ml | — | — | — |
| 14-188-104 | A11 | — | — | — | — | — | 5 ng/ml | — | — | — |
| 14-178-125 | A13 | — | — | — | — | — | 500 pg/ml | — | — | — |
| 14-153-234 | A234 | — | — | — | — | — | 500 pg/ml | — | — | — |
| C11-3 | C11-3 | — | — | — | — | — | — | — | — | — |
| C11-7 | C11-7 | — | — | — | — | — | — | — | — | — |
| C11-10 | C11-10 | — | — | — | — | — | — | — | — | — |
| C11-14 | C11-14 | — | — | — | — | — | — | — | — | — |
| C11-15 | C11-15 | — | 50 ng/ml | — | — | — | — | — | — | — |

| Monoclonal | | 1<br>aa96-120 | 2<br>aa106-130 | 3<br>aa116-140 | 4<br>aa126-150 | 5<br>aa136-160 | 6<br>aa146-170 | 7<br>aa158-180 | 8<br>aa169-191 |
|---|---|---|---|---|---|---|---|---|---|
| 14-1350-210 | A07 | — | — | — | — | — | — | — | — |
| 13-975-157 | A08 | — | 50 ng/ml | — | — | — | — | — | — |
| 13-959-270 | A09 | — | — | — | — | — | — | — | — |
| 110-81-17 | A15 | 50 ng/ml | 5 ng/ml | — | — | — | — | — | — |
| 107-35-54 | A04 | 50 ng/ml | — | — | — | — | — | — | — |
| 14-1708-269 | A269 | — | — | — | — | — | — | — | — |
| 14-1705-255 | A10 | — | — | — | — | — | — | — | — |
| 14-1287-252 | A12 | — | — | — | — | — | — | — | — |
| 14-1269-281 | A03 | — | — | — | — | — | — | — | — |
| 14-947-104 | A16 | — | — | — | — | — | — | — | — |
| 14-945-218 | A218 | — | — | — | — | — | — | — | — |
| 14-886-216 | A14 | — | — | — | — | — | — | — | — |
| 14-726-217 | A06 | — | — | — | — | — | — | — | — |
| 14-635-225 | A05 | — | — | — | — | — | — | — | — |
| 14-283-112 | A112 | — | — | — | — | — | — | — | — |
| 14-188-104 | A11 | — | — | — | — | — | — | — | — |
| 14-178-125 | A13 | — | — | — | — | — | — | — | — |
| 14-153-234 | A234 | — | — | — | — | — | — | — | — |
| C11-3 | C11-3 | 5 ng/ml | — | — | — | — | — | — | — |
| C11-7 | C11-7 | — | 50 pg/ml | 5 ng/ml | — | — | — | — | — |
| C11-10 | C11-10 | — | — | — | — | — | — | — | — |
| C11-14 | C11-14 | — | — | — | — | — | — | — | — |
| C11-15 | C11-15 | — | — | — | — | — | — | — | — |

EXAMPLE II

Epitope Mapping of Monoclonal Antibodies
A. Preparation of HCV Gene Fragment Library.

A plasmid containing nucleotides 14–5294 of the H strain of HCV (Ogata et al., *Proc. Natl. Acad. Sci. USA* 88:3392–3396 (1991)) in pGEM-9Zf(−) (Promega Corp., Madison, Wis.) was partially digested using DNase I by the following method in order to obtain random epitope-encoding fragments:

Five μg aliquots of plasmid DNA were incubated at 15° C. for 10 minutes in 0.5 M Tris-HCl, pH 7.6, and 10 mM MnCl$_2$ in the presence of anywhere from 0.1 to 0.7 units of DNase I. Aliquots from each digestion were analyzed by agarose gel electrophoresis. The two digestion mixtures containing 0.6 and 0.7 units of DNase I were found to give the largest amount of fragments in the 50–200 bp range. These two mixtures were pooled and extracted one time with an equal volume of phenol-chloroform (1:1, v/v) then precipitated by the addition of one tenth volume 3 M sodium acetate and 2.5 volumes 100% ethanol followed by centrifugation at 14,000×g for 10 minutes. The ends of the DNA molecules were then made blunt using the PCR Polishing kit (Stratagene, Inc., La Jolla, Calif.) as per manufacturer's directions. The DNA was again extracted and precipitated as described above, followed by ligation to a double-stranded adaptor in a 10 μl reaction volume using a T4 DNA ligase kit (Stratagene, Inc., La Jolla, Calif.) as directed by the manufacturer. The sequence of this double stranded adaptor was:

```
5'-GATCGCTCGAATTCCTCG-3'    (SEQUENCE ID NO:1)

3'-TTCTAGCGAGCTTAAGGAGC-5'  (SEQUENCE ID NO:2)
```

The sense-strand oligonucleotide of the adaptor (SEQ ID NO:1) was then used as a primer in a PCR reaction such that all DNAs were amplified independent of their sequence. This method is a modification of that described by Akowitz et al., *Gene* 81:295–306 (1989) and Reyes et al., *Mol. Cell. Probes* 5:473–481 (1991). PCR was performed in the presence of the sense-strand oligonucleotide primer at a final concentration of 1 μM in a reaction volume of 100 μl using the GeneAmp Gold PCR kit (PE Applied Biosystems, Foster City, Calif.) as directed by the manufacturer in a PE-9600 thermocycler. A pre-incubation at 94° C. for 8 min was followed by twenty-five cycles of PCR as follows: denaturation at 94° C. for 20 seconds, annealing at 55° C. for 30 seconds, and extension at 72° C. for 1.0 min. This was followed by a final extension step at 72° C. for 10 min. The PCR product was extracted and precipitated as described above. The entire PCR was run on a 1.2% agarose gel and a gel slice containing DNA fragments between approximately 70 and 250 bp was removed. The DNA was extracted from the gel slice using the QIAEX II kit (QIAGEN, Inc., Valencia, Calif.) as per manufacturer's directions. The DNA was digested with the restriction enzyme EcoRI (New England Biolabs, Beverly, Mass.) as directed by the manufacturer. The digested DNA was then extracted and precipitated as described above.

T7Select10-3b (Novagen, Inc., Madison, Wis.) was digested with EcoRI and dephosphorylated with calf intestinal alkaline phosphatase (New England Biolabs, Beverly, Mass.) as directed by the manufacturer. Size-selected digested DNA fragments (30 ng) (supra) were ligated with 0.5 μg digested T7Select10-3b in a 5 μl reaction volume at 16° C. overnight. The entire ligate was packaged into phage heads using T7Select packaging extract (Novagen, Inc., Madison, Wis.) and titered as directed by the manufacturer. The resulting unamplified library contained a total of 3.9× $10^6$ members (PFU). The packaged phage were amplified by liquid lysate amplification in *E. coli* BLT5403 (20 ml culture) as directed by the *T7 Select System Manual* (Novagen, Inc., Madison, Wis.). The amplified library had a titer of 1.3×$10^{11}$ PFU per ml.

B. Biopanning of HCV Gene Fragment Library.

Each monoclonal antibody (20 μg) that was to be used for biopanning was incubated at 4° C. for 4 hours on an end-over-end rocker in 300 μl blocking buffer (2% BSA, 3% nonfat dry milk, 0.2% Tween 20, 0.02% sodium azide in phosphate-buffered saline). During the incubation of the monoclonal antibody, an aliquot of the amplified HCV gene fragment library (supra) containing approximately $10^{11}$ phage was precipitated as follows: 1/10 volume of 5 M NaCl was added to the phage, mixed thoroughly, followed by addition of 1/6 volume polyethylene glycol (MW 8000), mixed thoroughly again, and incubated on ice for 1–2 hours. The phage were centrifuged at 6000×g for 10 min at room temp, all supernatant was removed and the phage pellet was vigorously resuspended in 120 μl buffer containing 1 M NaCl, 10 mM Tris-HCl pH 8.0, 1 mM EDTA. The phage were added to the pre-incubated monoclonal antibody and incubated at 4° C. overnight on an end-over-end rocker.

The next morning, the antibody-phage complexes were captured on paramagnetic particles coupled to goat anti-mouse IgG (Fc specific) as follows. A 0.2 ml aliquot of Goat Anti-Mouse IgG Fc BioMag particles (Polysciences, Inc., Warrington, Pa.) was washed three times with 0.4 ml 0.1% Tween 20, 0.1% BSA, 0.02% sodium azide in phosphate-buffered saline (PBS) by gentle vortexing followed by capture on a magnetic stand for 0.5–1 minute. The supernatant was removed carefully without disturbing the particles. Particles were then resuspended in the IgG-phage from overnight incubation above and incubated at room temperature on an end-over-end rocker for 3 hours. Particles were washed six times as above using 6.0 ml 0.5% Tween 20, 0.1% BSA in PBS per wash. Bound phage were eluted using 0.2 ml 0.1% Tween 20, 0.1% BSA, 1.0% SDS in PBS at room temperature on an end-over-end rocker for 90 minutes. The tube was placed on a magnetic stand for 1–2 minutes, after which the supernatant containing the eluted phage was removed to a clean tube. The sample containing eluted phage was titered as directed in the *T7 Select System Manual*.

The eluted phage was amplified as follows. Ten ml LB Broth (Gibco BRL, Gaithersburg, Md.) plus 100 μg/ml ampicillin was inoculated with *E. coli* BLT5403 and incubated at 37° C. overnight with shaking. The following morning, 35 ml LB Broth plus 100 μg/ml ampicillin, 1× M9 salts, 0.4% glucose, 1 mM $MgSO_4$ was inoculated with 0.2 ml of the overnight culture and incubated at 37° C. with shaking until the A600 absorbance was 0.5–0.6. Eluted phage (185 μl) from first round biopanning (supra) was added and incubation at 37° C. was continued for 1.5–2 hours, until the A600 absorbance of the culture had dropped to approximately 0.5, indicating lysis. The culture was centrifuged at 8000×g for 10 minutes and the supernatant was removed to a clean tube and stored at 4° C. The culture supernatant was titered as directed in the *T7 Select System Manual*.

One to two subsequent rounds of biopanning and amplification were performed as above with the following modifications. After pre-blocking the monoclonal antibody for 4 hours at 4° C., 150 μl amplified phage from the previous round of biopanning was added instead of $10^{11}$ PEG-precipitated phage from the starting library. In addition, after biopanning, a 20 ml culture rather than a 35 ml culture was used to amplify the eluted phage, and 100 μl rather than 185 μl of eluted phage was added to the culture.

C. Selection and Sequencing of HCV Core-Containing Clones.

A DNA fragment containing a region of the HCV genome that encodes amino acids 1–173 of the HCV nucleocapsid protein was utilized as a hybridization probe. This region was chosen because all of the monoclonal antibodies analyzed in the biopanning experiments recognize epitopes in the HCV core protein. Phage resulting from 2–3 rounds of biopanning and amplification were plated on *E. coli* BLT5403 and incubated at 37° C. until plaques formed. DNA was transferred onto Hybond-N+ membranes (Amersham Life Sciences, Inc., Arlington Heights, Ill.), denatured, neutralized, and UV cross-linked, as described by the manufacturer. The membranes were pre-hybridized, hybridized with the HCV nucleocapsid gene $^{32}$P-labeled probe, washed and exposed as described and known in the art. Individual hybridizing plaques were isolated and the inserts were amplified by PCR using T7SelectUP and T7SelectDOWN primers (Novagen, Inc., Madison, Wis.) as directed in the *T7Select System Manual*. For each monoclonal antibody, 30–50 independent hybridizing plaques were amplified and then purified using the QIAquick PCR purification kit (Qiagen, Inc., Chatsworth, Calif.). Purified PCR products were sequenced directly on an ABI Model 377 DNA Sequencer using the ABI Big Dye Terminator Cycle Sequencing Ready Reaction kit (Perkin-Elmer) and the T7SelectUP primer. All of the sequences resulting from biopanning with a particular monoclonal antibody were aligned with the HCV nucleocapsid gene sequence and the minimum region of overlap among all clones was identified. This overlap region defined the epitope recognized by the monoclonal antibody. The epitopes recognized by several monoclonal antibodies that were identified using this method are shown in TABLE III.

TABLE III

| Monoclonal Antibody | Region of HCV Core Recognized |
| --- | --- |
| C11-15 | Amino acids 19–27 |
| C11-10 | Amino acids 32–36 |
| C11-14 | Amino acids 45–50 |
| C11-3 | Amino acids 104–110 |
| C11-7 | Amino acids 112–124 |
| 14-635-225 | Amino acids 49–53 |
| 14-153-462 | Amino acids 50–63 |
| 14-726-217 | Amino acids 57–63 |
| 14-178-125 | Amino acids 59–64 |
| 14-1269-281 | Amino acids 59–64 |
| 14-947-104 | Amino acids 59–64 |
| 14-188-104 | Amino acids 59–64 |
| 14-1708-269 | Amino acids 59–64 |
| 107-35-54 | Amino acids 102–109 |

EXAMPLE III

Construction of Recombinant Antigens for Use in an HCV Core Antibody/Antigen Combination Assay A. Background.

The human immune response to Hepatitis C Virus (HCV) core is, for the most part, exclusive to the N-terminal half of the native protein. Multiple epitopes (regions comprising a defined number of amino acids, usually <10) have been identified within the first 115 amino acids of the native protein (Sallberg et al). Therefore, recombinant antigens utilized in assays for the detection of human anti-core antibodies present in the serum of infected individuals need only contain this portion of the native protein. Conversely, in vitro assays for the detection of HCV core protein utilize murine monoclonal antibodies to capture and detect native core protein also present in the serum of infected individuals. Combination assays for the simultaneous detection of both core antigen and human anti-core antibody in a single assay combine the two assay formats. In this case, a recombinant core antigen is necessary that will be recognized by human anti-core antibodies present in the serum, while escaping recognition by the murine monoclonal antibodies used to capture and detect native core antigen also present in serum. Such recombinants can be constructed by eliminating small regions (1–30 or more amino acids) within the core antigen, thus disrupting or eliminating the epitope(s) recognized by the murine monoclonal antibodies while at the same time leaving undisturbed numerous other epitopes that will allow human anti-core antibody detection.

B. Antigen Construction.

The first of these antigens constructed contained HCV amino acids 8–100 in which amino acids 32–50 were deleted from the recombinant. In this manner, antibodies C11-10 and C11-14, which bind to epitopes at amino acids 32–36 and 45–50, respectively (Example II), will not bind to the resulting recombinant antigen. A plasmid containing a bacterial codon-optimized version of nucleotides 342–791 from the H strain of HCV (Ogata, supra (1991)) was used as template for the PCR. oligonucleotide primers designed to this sequence were utilized to amplify two distinct fragments (1=SEQ ID NO:1 and SEQ ID NO:2; 2=SEQ ID NO:3 and SEQ ID NO:4) of the HCV core antigen, one upstream of the deletion and the other downstream of the deletion. Additionally, the oligonucleotide primers flanking the deletion on each fragment (SEQ ID NO:2 and SEQ ID NO:3) contained regions of overlap with one another. PCR was performed in a PE-9600 thermocycler in the presence of 0.5 $\mu$M of each oligonucleotide primer and 3–5 pg of plasmid template using the TaKaRa LA Taq PCR Kit (Pan Vera, Corp., Madison, Wis.) as per manufacturer's instructions (50 $\mu$l volume). A pre-incubation at 94° C. for 1 minute was followed by 35 cycles of PCR (denaturation at 94° C. for 20 seconds; annealing at 50° C. for 30 seconds; extension at 72° C. for 30 seconds), which was then followed by a final extension at 72° C. for 10 minutes. Following the independent amplification of the two fragments, each was purified using the QIAquick PCR Purification Kit (QIAGEN, Inc., Valencia, Calif.) and eluted into 25 $\mu$l of water. A second round of PCR was then performed as supra for 10 cycles to tether the two purified fragments (1 $\mu$l each in a 20 $\mu$l volume reaction) to one another at the regions of overlap within the oligonucleotide primers (SEQ ID NO:2 and SEQ ID NO:3). Finally, the product of the second PCR was amplified in a third PCR for 35 cycles utilizing 0.5 $\mu$M of the flanking oligonucleotide primers (SEQ ID NO:1 and SEQ ID NO:4) and the conditions described supra (100 $\mu$l volume).

C. Recombinant Expression.

The product of the third PCR was purified using the QIAquick PCR Purification Kit, then digested with the restriction enzymes EcoRI and BamHI, digestion sites that were incorporated into the flanking oligonucleotide primers (SEQ ID NO:1 and SEQ ID NO:4). The fragment encoding the recombinant was ligated into the bacterial expression vector pJO200 that had been similarly digested with EcoRI and BamHI using the pGEM-T Easy Ligation Kit (Promega, Madison, Wis.), then transformed into XL1-Blue competent cells (Stratagene, La Jolla, Calif.). After selection of clones containing the appropriately sized inserts, the nucleotide sequence of the recombinant was confirmed (SEQ ID NO:5), exhibiting the deduced amino acid sequence (SEQ ID NO:6). (See U.S. Pat. Nos. 5,322,769 and 6,172,189 for a description of the expression of recombinant proteins.)

D. Other Recombinants.

Several other HCV core recombinants have been constructed, cloned and expressed in a manner identical to that described supra. The first of these (see nucleotide sequence SEQ ID NO:7 and corresponding amino acid sequence SEQ ID NO:8) contains HCV amino acids 8–100 in which amino acids 33–35 and 46–49 have been deleted. The oligonucleotide primers utilized to amplify the two fragments in the first PCR were SEQ ID NO:1 and SEQ ID NO:9, and SEQ ID NO:10 and SEQ ID NO:4, respectively, followed by final amplification in the third PCR with SEQ ID NO:1 and SEQ ID NO:4. The second of these recombinants (see nucleotide sequence SEQ ID NO:11 and corresponding amino acid sequence SEQ ID NO:12) encodes HCV amino acids 8–100 in which the leucine residue at amino acid 36 has been substituted with valine, and the arginine residue at amino acid 47 has been substituted with leucine. The oligonucleotide primers utilized to amplify the two fragments in the first PCR were SEQ ID NO:1 and SEQ ID NO:13, and SEQ ID NO:14 and SEQ ID NO:4, respectively, followed by final amplification in the third PCR with SEQ ID NO:1 and SEQ ID NO:4. Finally, a recombinant (see nucleotide sequence SEQ ID NO:15 and corresponding amino acid SEQ ID NO:16) encoding HCV amino acids 8–100 was constructed using oligonucleotide primers SEQ ID NO:1 and SEQ ID NO:4 in a single PCR reaction.

EXAMPLE IV

Construction of Additional Recombinant Antigens for Use in an HCV Core Antibody/Antigen Combination Assay A. Background.

Additional recombinant antigens constructed for use in an HCV antigen/antibody combination assay included antigens that contained the 33c region of HCV (amino acids 1192–1457) tethered to a core region of the virus. The template used for such constructions was a plasmid containing a bacterial codon-optimized sequence of amino acids 1192–1457, followed by amino acids 1–150 from the H strain of HCV (Ogata, 1991), with two non-HCV coding amino acids separating the two sequences. This recombinant (HC-43) is routinely used in multiple commercial assays for the detection of HCV. The HC43 recombinant is expressed as a non-fusion protein from the pL promoter of bacterial phage lambda. (See U.S. Pat. Nos. 5,705,330, 5,616,460 and 5,773,212 for a discussion of HC43 and U.S. Pat. Nos. 6,153,377 and 5,859,193 for a discussion of the lambda pL vector system.) The additional recombinants were constructed by one of two methods. First, existing clones encoding distinct, related recombinants were joined by DNA ligation to form a third unique recombinant, or, new unique clones were constructed by tethering PCR described in Example III, Part B.

B. Initial Antigen Construction.

The first of the newer antigens constructed (p9MB-18) contained HCV amino acids 1192–1457 (representing a segment of NS3) tethered to amino acids 1–100 (representing a segment of core protein) in which amino acids 32–50 had been deleted. This recombinant was constructed by restricting plasmid pHC43 with the endonucleases, Xma I and Bam HI. Xma I cuts pHC43 near amino acid 24 of the core-encoding region while Bam HI cuts downstream of the translation termination codon. This region of pHC43 was replaced by DNA ligation using the pGEM-T Easy Ligation Kit (Promega Corp., Madison, Wis.), with the Xma I-Bam HI fragment obtained from the pJO200 vector encoding HCV core amino acids 8–100 with 32–50 deleted described in Example III (SEQ ID NO:5 and SEQ ID NO:6). The new plasmid was then used to transform XL1-Blue competent cells (Stratagene, La Jolla, Calif.). After selection of clones containing the appropriately sized insert, the nucleotide sequence of the recombinant was confirmed (SEQ ID NO:17), exhibiting the deduced amino acid sequence in SEQ ID NO:18.

C. Other Recombinants Constructed by Tethering PCR.

Recombinant antigens made by tethering PCR were constructed as detailed in Example III, Part B. The first of these recombinants, p9MB-19 (SEQ ID NO:19 (nucleotide sequence) and SEQ ID NO:20 (amino acid sequence)), contains HCV amino acids 1192–1457 followed by amino acids 8–100 in which amino acids 32–50 had been deleted. The oligonucleotide primers used to amplify the initial two fragments in the first PCR were SEQ ID NO:21 and SEQ ID NO:22, and SEQ ID NO:23 and SEQ ID NO:4, respectively.

Final amplification in the third PCR utilized oligonucleotide primers SEQ ID NO:21 and SEQ ID NO:4.

Recombinant p9MB-20 (SEQ ID NO:24 and SEQ ID NO:25) contains HCV amino acids 1192–1457, four glycine residues and a serine residue, followed by HCV amino acids 8–100 in which amino acids 32–50 had been deleted. The oligonucleotides primers used to amplify the initial two fragments in the first PCR were SEQ ID NO:21 and SEQ ID NO:22, and SEQ ID NO:26 and SEQ ID NO:4, respectively. Final amplification in the third PCR utilized oligonucleotides primers SEQ ID NO:21 and SEQ ID NO:4.

Recombinant p9MB-22 (SEQ ID NO:27 and SEQ ID NO:28) contains HCV amino acids 1192–1457, four glycine residues and a serine residue, followed by HCV amino acids 1–150. The oligonucleotides primers used to amplify the initial two fragments in the first PCR were SEQ ID NO:21 and SEQ ID NO:22, and SEQ ID NO:29 and SEQ ID NO:30, respectively. Final amplification in the third PCR utilized oligonucleotides primers SEQ ID NO:21 and SEQ ID NO:30.

Recombinant p9MB-31 (SEQ ID NO:31 and SEQ ID NO:32) contains HCV amino acids 1192–1457 followed by amino acids 1–100 in which amino acids 31, 32, 33, 47 and 48 had been deleted. The oligonucleotides primers used to amplify the initial two fragments in the first PCR were SEQ ID NO:21 and SEQ ID NO:33, and SEQ ID NO:34 and SEQ ID NO:4, respectively. Final amplification in the third PCR utilized oligonucleotides primers SEQ ID NO:21 and SEQ ID NO:4.

D. Other Recombinants Constructed by DNA Ligation.

Recombinant 9MB-24 (SEQ ID NO:35 and SEQ ID NO:36) contains HCV amino acids 1192–1457 followed by amino acids 1–100 in which amino acids 33–35 and 46–49 were deleted from the recombinant. This recombinant was constructed by restricting plasmid pHC43 with the endonucleases, Xma I and Bam HI, and replacing the fragment by DNA ligation, with the Xma I-Bam HI fragment obtained from SEQ ID NO:7.

Recombinant 9MB-25 (SEQ ID NO:37 and SEQ ID NO:38) contains HCV amino acids 1192–1457, four glycine residues and a serine residue, followed by HCV amino acids 1–100 in which amino acids 33–35 and 46–49 were deleted from the recombinant. This recombinant was constructed by restricting plasmid p9MB-22 with the endonucleases, Xma I and Bam HI, and replacing the fragment by DNA ligation, with the Xma I-Bam HI fragment obtained from SEQ ID NO: 7.

Recombinant 9MB-25 (SEQ ID NO:39 and SEQ ID NO:40) contains HCV amino acids 1192–1457, four glycine residues and a serine residue, followed by HCV amino acids 1–100 in which amino acids 32–50 were deleted from the recombinant. This recombinant was constructed by restricting plasmid p9MB-22 with the endonucleases, Xma I and Bam HI, and replacing the fragment by DNA ligation, with the Xma I-Bam HI fragment obtained from p9MB-18 (SEQ ID NO:27).

EXAMPLE V

Preparation of Microparticles

Microparticles, coated with several monoclonal antibodies, were prepared by coating several separate populations of microparticles with HCV monoclonal antibodies which recognize different regions within the HCV core protein. Similarly, microparticles were coated with recombinant antigens cloned from the NS3 and NS4 regions of HCV. The peptide used for microparticle coating was from the core region of HCV.

Microparticles for Antibody Assay:

The following recombinant proteins and peptides were used to coat the microparticles for antibody assays.

A. Preparation of Recombinant Proteins:

i. HCV HC43 antigen HCV. HC43 recombinant antigen was obtained from Chiron Corporation, Emeryville, Calif. It contained amino acid sequence 1–150 (corresponding to the core protein) and 1192–1457 (corresponding to amino acid residues within NS3) of HCV-1 (amino acid sequence available from GenBank®, as described hereinabove)

ii. HCV C-100 antigen. HCV C-100 recombinant antigen was obtained from Chiron Corporation, Emeryville, Calif. It contained amino acid sequence 1569–1961 (corresponding to amino acid residues within NS4) of HCV-1 (available from GenBank®, as described hereinabove).

iii. HCV NS5 antigen. HCV NS5 recombinant antigen was obtained from Chiron Corporation, Emeryville, Calif. It contained amino acid sequence 2054–2995 of HCV (available from GenBank®, described hereinabove).

iv. HCV NS3 NS4 $E.$ $Coli$ construct CKS-33c-BCD antigen. HCV HC31 recombinant antigen was obtained from Chiron corporation, Emerville, Calif. It contained amino acid Sequence 1192–1457 of HCV, and amino acid sequence 1676–1931 of the NS4 region. In addition, it consists of 239 amino acids of CKS (available from GenBank®, described hereinabove).

A1. Preparation of R-Antigen Coated Microparticles.

i. Preparation of HCV HC43/C100 Microparticles. Microparticles coated with both HC43 and c-100 were prepared in the following manner. Briefly, a 500 µl aliquot of microparticles (10% weight/volume, 0.7–0.9 micron, available from Seradyn, Indianapolis, Ind.) was mixed with 962 µl of a coating buffer (Phosphate buffer, pH 5.0 with Tween-20) for approximately 1 minute at room temperature. Then, 154 µl of an HCV C100-3 antigen solution (0.65 mg/ml) and 308 ul of an HC43 antigen solution (650 µg/ml) were added to the microparticle solution, mixed and tumbled for 16 hours at room temperature. The microparticles were pelleted at 12,000×g for 10 minutes in an Eppendorf microfuge. The suspension was removed, and the microparticles were washed with wash buffer (Phosphate, NaCl, dithiothreitol-DTT, EDTA, sodium dodecyl sulfate-SDS, pH 6.5) and heat stressed at 56° C. for 20 hours. The microparticles were then resuspended in 2.5 ml of microparticle diluent (Phosphate Buffer, pH 6.5, EDTA, DTT, NaCl and SDS, Sucrose, azide) at a final concentration of 2.0%.

ii. Preparation of HCV NS5 Microparticles. Five hundred and thirty microliters of an HCV NS5 coating buffer (Carbonate, pH 10, SDS) and 200 µl of a 10% weight/volume 0.7–0.9 micron microparticles (available from Seradyn, Indianapolis, Ind.) were added to 270 µl of the HCV NS5 antigen solution (concentration of 650 µg/ml). The microparticles were mixed and tumbled for 16 hours at room temperature. The microparticles were pelleted at 12,000×g for 10 minutes in an Eppendorf microfuge. The suspension was removed and the microparticles were washed with wash buffer (Phosphate, NaCl, DTT, EDTA, SDS, pH 6.5) and heat stressed at 56° C. for 20 hours. The washed microparticles were then resuspended in 2.5 ml of microparticle diluent (Phosphate Buffer, pH 6.5, EDTA, DTT, NaCl and SDS, Sucrose, azide) at a final concentration of 0.4%.

iii. Preparation of HCV NS3 NS4 $E.$ $Coli$ Construct CKS-33c-BCD Microparticles. A 100 µl aliquot of microparticles (10% weight/volume, 0.7–0.9 micron, available from Seradyn, Indianapolis, Ind.) was mixed with 452 µl of coating buffer (Phosphate buffer, pH 5.0 with Tween-20) for approximately 10 minutes at room temperature. Then, 200 µg of CKS-33C-BCD Ag was added and mixed for 16 hours at room temperature.

The microparticles were pelleted at 12,000×g for 10 minutes in an Eppendorf microfuge. The prepared microparticles were washed with wash buffer (DTT, EDTA, SDS in PBS, pH 6.5). The supernatant was removed, and the microparticles were resuspended in 1 ml of microparticle diluent (Phosphate Buffer, pH 6.5, EDTA, DTT, NaCl, Sucrose and SDS, Sucrose).

iv. Blending of HCV HC43/C100 and HCV NS5 Microparticles. Two hundred twenty microliters of HCV HC43/C100 microparticles prepared as described in Example (IV) (A1) (i) and 330 µl of HCV NS5 microparticles prepared as described in Example (IV) (A1) (ii) were mixed together. This mixture was incubated at room temperature for 15 minutes and diluted to 50 ml in microparticle diluent. (Phosphate Buffer, pH 6.5, EDTA, DTT, NaCl, Sucrose and SDS, Sucrose).

v. Preparation of Biotinylated Core Peptide. HCV core peptide aa 11-28 was biotinylated at N-terminus during synthesis using an automated peptide synthesizer with ≧90% purity.

vi. Preparation of Streptavidin-Coated Microparticles. A four ml aliquot of carboxylated microparticles (10% weight/volume, 0.227 micron, Seradyn, Indianapolis, Ind.) was mixed with 2486 ul of coupling buffer (MES (2-(N-morpholino) ethanesulfonic acid) pH 6.7) for 10 minutes at room temperature. Then, 114.4 µl of EDAC solution (10 mg/ml in coupling buffer) was added to the microparticle solution and mixed for 15 minutes at room temperature. Subsequently, 1 ml of Streptavidin solution (1 mg/ml in PBS) was added to the activated microparticles and tumbled for 16 hours at room temperature. The prepared microparticles were then pelleted at 12,000×g for 3 minutes in an Eppendorf microfuge. The supernatant was removed, and the microparticles were resuspended in 4 ml of PBS. The centrifugation process was repeated one more time, and microparticles were stored in 4 ml of PBS to yield a final concentration of approximately 1%.

vii. Preparation of Core Peptide Coated Microparticles.

To 1 ml of coated microparticles from Example (IV) (A1) (vi) was added 375 µl of HCV Core peptide from Example (V) (A1) (v) and 11-28 aa at 1 mg/ml in PBS buffer. The mixture was then incubated for 2 hours at room temperature. The prepared microparticles were washed with wash buffer (DTT, EDTA, SDS in PBS, pH 6.5), and the microparticles were resuspended in 1 ml of microparticle diluent (Calf Bovine Serum, Horse IgG, TWEEN 20, BSA, Casein, EDTA, Sucrose and Proclin, pH 6.5) yielding 1% solids final concentration.

Microparticles for the Antigen Assay:

B. Preparation of Monoclonal Antibodies:

The methods for generating monoclonal antibodies are presented in U.S. Pat. No. 5,753,430. Briefly, $E.$ $coli$ derived recombinant antigens encoded by HCV sequences, designated as pHCV34 (HCV-core, a.a. 1-150), were employed as immunogens for antibodies to core. Detailed information on the cloning of pHCV34 is disclosed in U.S. patent application Ser. No. 07/572,822, incorporated herein by reference). The protein was prepared for immunization with appropriate adjuvants after purification, as would be performed by those skilled in the art.

BALB/c mice were injected intraperitoneally with 15 µg of purified pHCV34 with 15 µg each of Trehalose dimycolate (TDM) and $M.$ $phlei$ in a buffer emulsion prepared according to the manufacturer's instructions. Subsequent immunizations were performed on day 14, 28 and 42. Mice were bled on days 21 and 49, and the immune response was studied by enzyme-linked immunosorbent assay utilizing pHCV34 coated on polystyrene beads, as detailed in U.S. Pat. No. 5,753,430.

Upon demonstration of specific anti-HCV antibody present at reasonable titers in the sera of immunized mice, mice were boosted with 40 μg of pHCV34 antigen. The mice were sacrificed and their spleens were removed; the white cells were mixed and fused with SP2/0 cells. The cell mixture was cultured in Biscoe's Modified Dubach's Medium (IMDM) supplemented with 20% fetal calf serum, and the hybridized cells were selected by using a hypoxanthine and thymidine medium. Hybridoma cell lines were established, and all monoclonal antibodies specific for antibodies to core were prepared from ascite fluids of the mice and were purified by chromatography on a protein-A column (Pharmacia, Uppsala, Sweden). The epitopes of the monoclonal antibodies were analyzed by an ELISA test described in Example I.

B1. Preparation of Monoclonal Antibody-Coated Microparticles for Antigen Assay.

i. Preparation of HCV C11-14 Microparticles. Briefly, a 1 ml aliquot of carboxylated microparticles (10% weight/volume, 0.227 micron, available from Seradyn, Indianapolis, Ind.) was mixed with 9 ml of coupling buffer (MES (2-(N-morpholino) ethanesulfonic acid), pH 6.7) for approximately 10 minutes at room temperature. Then, 150 μl of 1-ethyl-3-(3-dimethylaminopropyl) carbodiimide (EDAC, 10 mg/ml in coupling buffer, Sigma Chemical Company) was added to the microparticle solution and mixed for 15 minutes at room temperature. Eighteen hundred and twenty-two microliters of C11-14 monoclonal antibody solution (2.13 mg/ml) was added to the activated microparticles, mixed and tumbled for 16 hours at room temperature. The microparticles were then pelleted at 12,000×g for 3 minutes in an Eppendorf microfuge. The supernatant was removed, and the microparticles were washed with microparticle wash buffer (Phosphate Buffer Saline-PBS, Tween 20, pH 7.2), followed by washing with microparticle coating buffer (Tris Buffer Saline-TBS, Bovine Serum Albumin-BSA, pH 7.2) and final washing with microparticle final exchange buffer (PBS, Tween 20, pH 7.2). The microparticles were resuspended in 5 ml of final exchange buffer and heat stressed at 45° C. for 72 hours. After heat stress, 5 ml of microparticle diluent (Calf Bovine Serum, Horse IgG, Tween 20, BSA, Casein, Ethylene diamine tetraacetic acid (EDTA), Sucrose and Proclin, pH 6.5) was added to give a final concentration of approximately 1.0%.

ii. Preparation of HCV A5 (14-635-225) Mab Microparticles. A similar procedure as mentioned in Example (V) (B1) (i) was used, except that instead of C11-14 Mab, A5 14-635-225) Mab was used for coating on microparticles.

iii. Preparation of HCV C11-3 Microparticles. Six point six microliters of 1 N HCl was added to 300 μl (1.45 mg/ml) of C11-3 monoclonal antibody to bring the pH to 2.5. The monoclonal was then incubated at this pH for 5 minutes. The pH was then brought to 6.5 by adding 50 mM MES buffer. A 100 μl aliquot of carboxylated microparticles (10% weight/volume, 0.227 micron, Seradyn, Indianapolis, Ind.) was then mixed with 333 μl of coupling buffer (MES, pH 6.7) for 10 minutes at room temperature. Then, 15 μl of EDAC solution (10 mg/ml in coupling buffer) was added to the microparticle solution and mixed for 5 minutes at room temperature. Five hundred and fifty-two microliters of pH shocked C11-3 monoclonal antibody solution (0.725 mg/ml) were added to the activated microparticles, mixed and tumbled for 16 hours at room temperature. The microparticles were then pelleted at 12,000×g for 3 minutes in an Eppendorf microfuge. The supernatant was removed, and the microparticles were washed with microparticle wash buffer (Phosphated Buffered Saline (PBS), Tween 20, pH 7.2), followed by a wash with microparticle coating buffer (Tris Buffered Saline (TBS), Bovine Serum Albumin (BSA), pH 7.2) and a final wash with microparticle final exchange buffer (PBS, Tween 20, pH 7.2). The microparticles were resuspended in 0.5 ml of final exchange buffer and heat stressed at 45° C. for 72 hours. After heat stress, 0.5 ml of microparticle diluent (Calf Bovine Serum, Horse IgG, Tween 20, BSA, Casein, ethylene diamine tetraacetic acid (EDTA), Sucrose, and ProClin, pH 6.5) was added to give a final concentration of approximately 1.0%.

iv. Blending of HCV C11-14 and C11-3 Microparticles.

Thirty-six microliters of HCV C11-3 microparticles (1% solid) prepared as described in Example (V) (B1) (iii) and 84 μl HCV C11-14 microparticles (1% solids) prepared as described in Example (V) (B1) (i) were mixed with 880 μl microparticle diluent (Calf Bovine Serum Horse IgG, Tween 20, BSA, Casein, EDTA, Sucrose, and Proclin, pH 6.5).

C. Preparation of Microparticles for Combo Assay:

For the dual assay, two separate PRISM® channels were used, one for the HCV antibody assay and one for the HCV antigen assay. For the combo assay, both the antibody and antigen assays were performed on a single channel where the reagents for both antigen and antibody assay were combined in one kit.

i. Blending of C11-14 mAb Coated Microparticles with Core Antigen (Peptide)-Coated Microparticles and HCV HC33 Antigen Coated Microparticles. Three hundred and fifty microliters of core peptide coated microparticles (1% solids stock) prepared as in Example (V) (A1) (vii) and 700 μl of HCV NS3 NS4 E. coli Construct CKS-33C-BCD Ag coated microparticles (1% solids stock) prepared as described in Example (V) (A1) (iii) and 319 μl HCV C11-14 microparticles (1.0099% solids stock) prepared as described in Example (V) (B1) (i) were mixed with 5631 μl microparticle diluent (calf Bovine Serum, Horse IgG, Tween 20, BSA, Casein, EDTA, Sucrose and Proclin, pH 6.5).

D. Preparation of Microparticles for Combo Assay Using p9MB18-Coated Microparticles, c200-Coated Microparticles, and C11-14-Coated Microparticles:

i. HCV C-200 antigen. HCV C-200 recombinant antigen was obtained from Chiron Corporation, Emeryville, Calif. In particular, the antigen comprises amino acid sequence 1192–1932 of HCV (available from GenBank, as described hereinabove) and is from the NS3 and NS4 regions. The c200 antigen is a chimeric fusion protein, with 154 amino acids of human superoxide dismutase (hSOD).

ii. Preparation of c200 Microparticles. A 100 μl aliquot of microparticles (10% % weight/volume, 0.7–0.9 micron, available from Seradyn, Indianapolis, Ind.) was mixed with 830.6 μl of coating buffer (MES buffer, pH 6.5 with SDS) for approximately 10 minutes at room temperature. Then, 69.4 μl of c200 antigen solution (0.72 mg/ml) was added to the microparticle solution, mixed and tumbled for 16 hours at room temperature. The microparticles were pelleted at 12,000×g for 10 minutes in an Eppendorf microfuge. The suspension was removed, and the microparticles were washed with wash buffer (Phosphate, NaCl, EDTA, SDS, pH 6.5) and heat stressed at 56° C. for 16–20 hours. The microparticles were then resuspended in 500 μl of microparticle diluent (Phosphate Buffer, pH 6.5, EDTA, NaCl, Sucrose, SDS, azide) at a final concentration of 2.0%.

iii. Preparation of p9MB-18 Microparticles. A 100 μl aliquot of microparticles (10% weight/volume, 0.7–0.9 micron (available from Seradyn, Indianapolis, Ind.)) was mixed with 788 μl of coating buffer (MES buffer, pH 6.5 with SDS) for approximately 10 minutes at room temperature. Then, 112 μl of an HCV p9MB-18 antigen solution (0.89 mg/ml) was added to the microparticle solution, mixed and tumbled for 16 hours at room temperature. The microparticles were pelleted at 12,000×g for 10 minutes in an Eppendorf microfuge. The suspension was removed, and the microparticles were washed with wash buffer (phosphate, NaCl, EDTA, SDS, pH 6.5) and heat stressed at 56° C. for 16–20 hours. The microparticles were then resuspended in 500 ul of microparticle diluent (Phosphate Buffer, pH 6.5, EDTA, NaCl, Sucrose, SDS, azide) at a final concentration of 2.0%.

iv. Blending of C11-14 mAb Coated Microparticles with HCV p9MB-18-Coated Microparticles and HCV c200 Antigen-Coated Microparticles. Fifty microliters of p9MB-18 coated microparticles (2% solids stock) prepared as in Example (V) (D) (iii), 62.5 μl of HCV c200 Ag coated microparticles (2% solids stock) prepared as described in Example (V) (D) (ii) and 125 μl HCV C11-14 microparticles (2% solids stock) prepared as described in Example (V) (B1) (i) were mixed with 4762.5 μl microparticle diluent (EDTA, SDS, Sucrose and Proclin, PBS pH 6.5).

Sensitivity: The seroconversion sensitivity was 95.8% as compared to nucleic acid testing data. The PRISM® HCV Ag/Ab Real Combo assay detected 23/24 positive bleeds as reactive. Data is summarized in Table V, below. Overall sensitivity for the seroconversion panels shown in Table IV are comparable between the blended microparticles prepared as described in Example (V) (C) (i) and microparticles prepared as described in Example (V) (C) (iv) using assay format provided in FIG. 3. However, for anti-HCV Core, specific sample P9MB18-coated microparticles showed significant improvement over core specific peptide (11-28 aa, refer to Table VI), when used in combination in combo assay format (Table VI).

D. Preparation of p9MB31 Coated Microparticles:

i. A 100 μl aliquot of microparticles (10% weight/volume, 0.7–0.9 micron, available from Seradyn, Indianapolis, Ind.) was mixed with 788 μl of coating buffer (MES buffer, pH 6.5 with SDS) for approximately 10 minutes at room temperature. Then, 112 μl of an HCV p9MB-31 antigen solution (0.89 mg/ml) was added to the microparticle solution, mixed, and tumbled for 16 hours at room temperature. The microparticles were pelleted at 12,000×g for 10 minutes in an Eppendorf microfuge. The suspension was removed, and the microparticles were washed with wash buffer (Phosphate, NaCl, EDTA, SDS, pH 6.5) and heat stressed at 56° C. for 16–20 hours. The microparticles were then resuspended in 500 μl of microparticle diluent (Phosphate Buffer, pH 6.5, EDTA, NaCl, Sucrose, SDS, azide) at a final concentration of 2.0%.

Sensitivity: The sensitivity of the HCV panels was compared between microparticles coated with p9MB-18 and p9MB-31 r-antigen using the assay format provided in FIG. 1. Overall, sensitivity for both of these r-antigens is comparable as shown in Table IV.

TABLE IV

| Panel or Sample | p9MB18 coated uPS (V) (D) (iv) S/CO | p9MB31 coated uP (V) (E) (i) S/CO |
|---|---|---|
| Panel A | 13.03 | 9.43 |
| NABI #2 | 21.9 | 27.76 |
| NABI #15 | 28.21 | 33.04 |

Panel A is mainly anti-Core panel
NABI #2 is anti-NS3 sample.
NABI #15 is an anti-Core and anti-NS3 sample.

TABLE V

| Geno-type | Ag earlier than Ab by | Day Number | HCV RNA Test Results | HCV Ab S/CO | HCV Ag S/CO | HCV Ab/Ag Real Combo S/CO |
|---|---|---|---|---|---|---|
| 1a | 38 Days | 0 | − | 0.09 | 0.49 | 0.39 |
|  |  | 24 | + | 0.11 | 10.63 | 2.47 |
|  |  | 27 | + | 0.10 | 43.77 | 4.66 |
|  |  | 31 | + | 0.11 | 72.92 | 8.09 |
|  |  | 62 | + | 5.19 | 44.41 | 5.61 |
|  |  | 64 | + | 5.22 | 69.55 | 5.86 |
|  |  | 69 | + | 5.91 | 12.92 | 4.22 |
|  |  | 71 | + | 6.29 | 7.09 | 3.77 |
| 1b | 18 Days | 0 | + | 0.09 | 76.61 | 6.21 |
|  |  | 4 | + | 0.09 | 56.09 | 4.29 |
|  |  | 7 | + | 0.08 | 39.63 | 2.97 |
|  |  | 13 | + | 0.34 | 32.14 | 2.44 |
|  |  | 18 | + | 1.53 | 14.93 | 1.68 |
|  |  | 21 | + | 3.20 | 19.97 | 2.64 |
|  |  | 164 | Not Tested | 5.86 | 0.61 | 3.61 |
| 1a | 23 Days | 0 | − | 0.09 | 0.45 | 0.39 |
|  |  | 2 | − | 0.08 | 0.45 | 0.42 |
|  |  | 17 | + | 0.07 | 20.06 | 1.58 |
|  |  | 19 | + | 0.09 | 45.84 | 4.11 |
|  |  | 24 | + | 0.09 | 81.03 | 6.26 |
|  |  | 26 | + | 0.07 | 63.30 | 5.95 |
|  |  | 36 | + | 0.31 | 74.78 | 8.44 |
|  |  | 40 | + | 4.03 | 49.53 | 5.74 |
| 1a | 32 Days | 0 | − | 0.46 | 0.54 | 0.29 |
|  |  | 22 | − | 0.42 | 0.53 | 0.43 |

TABLE V-continued

| Geno-type | Ag earlier than Ab by | Day Number | HCV RNA Test Results | HCV Ab S/CO | HCV Ag S/CO | HCV Ab/Ag Real Combo S/CO |
|---|---|---|---|---|---|---|
| | | 24 | – | 0.43 | 0.47 | 0.40 |
| | | 42 | + | 0.46 | 8.79 | 0.99 |
| | | 46 | + | 0.44 | 22.26 | 2.02 |
| | | 74 | + | 4.22 | 19.82 | 2.40 |
| | | 76 | + | 4.50 | 23.78 | 2.99 |

TABLE VI

| Panel or sample | Peptide blended Combo ups (V) (C) (i) S/CO | P9MB-18 blended Combo ups (V) (D) (iv) S/CO |
|---|---|---|
| Panel A | 0.95 | 1.25 |
| NABI #7 | 0.44 | 2.27 |
| NABI 0141044662 | 1.15 | 2.04 |

*S/CO values ≧ 1.00 are considered reactive
NABI #7 and NABI 0141044662 are anti-HCV Core samples from NABI.
Panel A is mainly anti-Core panel.

EXAMPLE VI

Preparation of Acridinium-Labeled Conjugates

A. Conjugate for Antibody Assay:

For the antibody assay, either mouse anti-human IgG directly labeled with acridinium or a pre-complex of biotinylated anti-human F (ab')2 and acridinium anti biotin conjugate was used.

i. Pre-complex of biotinylated anti-human F(ab')2 and acridinium anti-biotin conjugate. The labeled anti-biotin antibody was prepared as disclosed in U.S. Pat. No. 5,705,330. The pre-complex of biotinylated Anti-human F(ab')2 and acridinium anti-biotin conjugate were also prepared as disclosed in U.S. Pat. No. 5,705,330.

ii. Acridinium labeled Mouse anti-Human IgG. Fifty-three point six microliters of conjugation buffer (CB) containing sodium phosphate, NaCl, 3-(3-chlolamidopropyl)-dimethylammonio-1-propane-sulfonate (CHAPS, Sigma Chemical Company, Saint Louis, Mo.), pH 8.0 and 7.2 µl of N-hydroxysuccinimide ester of 10-(3-sulfopropyl)-N-tosyl-N-(2-carboxyethyl)-9-acridinium carboxamide (4 mg/ml in dimethyl formamide) was added to 131 µl of Mouse anti-Human IgG (4.59 mg/ml) and 601 µl of PBS at room temperature. The reaction mixture was mixed with a rotator for 20 minutes at room temperature. The reaction was quenched by loading the reaction mixture onto the HPLC. This was applied to a 300×7.8 mm Bio-Sil SEC-250 gel filtration column (Bio-Rad, Richmond, Calif.) which had been equilibrated with buffer containing CHAPS, NaCl and sodium phosphate, pH 6.3. The column was eluted at 1.0 ml/min with the same buffer using a Beckman 421A controller equipped with a model 114M pump. Fractions of 1 ml were collected, and the absorbance determined at 280 nm and 370 nm with a Beckman DU-7 spectrophotometer. The extent of acridinium incorporation was calculated as described in U.S. Pat. No. 5,705,330. The acridinium to IgG ratio (mole/mole) obtained was approximately 2.5. The conjugate was stored at 4° C.

B. Conjugate for Antigen Assay:

i. Acridinylation of c11-10 conjugate. A similar procedure as mentioned in Example (V) (A) (ii) was used except for the following changes. Seven hundred microliters of conjugate buffer, 300 ul (1 mg/ml) of C11-10 Mab and 2.9 ul (4 mg/ml) of acridinium derivative were mixed for 10 minutes at room temperature. The acridinium to IgG ratio (mole/mole) obtained was approximately 2.0. The conjugate was stored at 4° C.

C. Conjugate for Combo Assay:

Blending of Acridinylated Mouse anti-Human IgG and Acridinylated C11-10 Mab Conjugate:

Fourteen microliters of Acridinylated Mouse Anti-Human IgG (1 ug/ml) was mixed with 390 µl of Acridinylated C11-10 Mab (1.79 µg/ml) conjugate yielding 2 ng/ml Mouse anti-Human IgG with 100 ng/ml C11-10, incubated for 2 hours and filtered before use.

Preparation of Mouse anti-Human IgG and Acridinylated C11-10 Mab conjugate are described in Example (V) (A) (ii) and (VI) (B), respectively.

EXAMPLE VII

Detection of HCV Core Protein by Monoclonal Antibodies

Since a large number of anti-HCV core monoclonal antibodies were available for use in developing an antigen detection assay, it was necessary to determine which combination of monoclonal antibodies would provide the greatest sensitivity. Because the number of combinations possible when using more than one monoclonal on the solid phase (i.e. for capture) and in the liquid phase (i.e. detection) is extremely large, a simplified "screening" method was used to identify the best performing pair of monoclonals. It was assumed that once the most sensitive pair was identified, other monoclonals could be added to improve assay sensitivity, if necessary.

In order to identify the best pairs, therefore, monoclonal antibodies were coated onto microparticles or conjugated with acridinium as described in Example IV and V. Screening assays used monoclonal antibody-coated microparticles (0.40 µm diameter) at a working concentration of 0.09–0.15% solids and conjugated monoclonals at a working concentration of 100–125 ng/ml. For all experiments, the same positive and negative control plasma were used (0.1 ml for each assay). The positive control serum was from an HCV-infected individual who tested negative for HCV antibodies but whose plasma had an HCV RNA titer of 19,000,000 copies per ml. The negative control plasma was from a normal blood donor who was negative for HCV antibodies and RNA. Assays were performed using the instrumentation and operation methods as described in Example IX.

Table VII shows the mean signal-to-negative (S/N) values obtained upon testing the various pairs of monoclonal antibodies for their ability to detect HCV core antigen in the positive control human plasma (nd: not determined). From this data, it is apparent that some pairs of monoclonal antibodies exhibit greater sensitivity than others and that the sensitivity was dependent upon the proper configuration of the assay. For example, when monoclonal antibody A05 was used as the capture reagent and C11-10 was used as the detection reagent, the resulting S/N value was 150.0; however, when the opposite configuration was used, the resulting S/N value was only 6.8 signal-to-negative (S/N) ratio obtained upon testing of a positive control human plasma from an individual who tested negative for HCV antibodies but whose plasma had an HCV RNA titer of 19,000,000 copies per ml. The negative control plasma was from a normal blood donor who was negative for HCV antibodies and RNA. Screening assays used coated microparticles at a working concentration of

TABLE VII

Detection of HCV Core Antigen in Human Plasma by Various Pairs of Anti-core Monoclonal Antibodies

| | | | | | | | CONJUGATE | | | | | | | | |
|---|---|---|---|---|---|---|---|---|---|---|---|---|---|---|---|
| | Mab | 107-35-54 | 14-635-225 | 14-726-217 | 13-975-157 | 13-959-270 | 14-178-125 | 14-886-216 | 110-81-17 | 14-945-218 | C11-3 | C11-7 | C11-10 | C11-14 | C11-15 |
| | | | | | | | Mab | | | | | | | | |
| MICRO-PARTICLE | | A04 | A05 | A06 | A08 | A09 | A13 | A14 | A15 | A218 | C11-3 | C11-7 | C11-10 | C11-14 | C11-15 |
| 14-1708-403 | A01 | 0.6 | nd | 1.3 | 2.5 | 1.0 | 1.3 | 5.2 | 1.0 | 1.4 | 2.4 | 0.9 | 53.0 | 1.9 | 3.5 |
| 14-153-462 | A02 | nd | nd | 1.4 | nd | 0.9 | 1.5 | 1.5 | nd | 2.4 | 0.6 | 1.0 | 22.0 | 1.8 | 0.2 |
| 14-1269-281 | A03 | 0.8 | nd | 1.3 | 2.4 | 1.1 | 1.3 | 7.4 | 0.9 | 1.4 | 2.2 | 2.9 | 101.6 | 3.0 | 6.0 |
| 107-35-54 | A04 | nd | nd | 0.9 | nd | nd | nd | nd | nd | nd | 1.7 | 1.2 | 7.6 | 12.9 | 1.3 |
| 14-635-225 | A05 | 1.2 | nd | 1.5 | 2.9 | 0.9 | 1.0 | 8.4 | 1.0 | 1.5 | 4.2 | 2.1 | 150.0 | 1.9 | 4.0 |
| 14-726-217 | A06 | nd | nd | 0.6 | nd | 1.6 | 1.8 | 2.5 | nd | 2.7 | 1.7 | 2.4 | 9.5 | 3.8 | 0.7 |
| 13-975-157 | A08 | nd | nd | 0.7 | nd | nd | nd | nd | nd | nd | 1.4 | 0.8 | 4.6 | 1.6 | 3.2 |
| 13-959-270 | A09 | nd | nd | 1.6 | nd | nd | nd | nd | nd | nd | 1.5 | 1.2 | 2.4 | 1.5 | 1.0 |
| 14-1705-255 | A10 | nd | nd | 0.7 | nd | 1.3 | 1.7 | 1.2 | nd | 2.5 | 1.6 | 1.3 | 13.6 | 4.5 | 1.2 |
| 14-188-104 | A11 | nd | nd | 0.8 | nd | 1.0 | 1.2 | 2.8 | nd | 1.2 | 2.8 | 0.7 | 16.5 | 1.8 | 2.4 |
| 14-1287-252 | A12 | nd | nd | 0.9 | nd | nd | nd | nd | nd | nd | 2.8 | 1.9 | 6.3 | 2.4 | 6.1 |
| 14-886-216 | A14 | nd | nd | 0.9 | nd | nd | nd | nd | nd | nd | 3.2 | 3.1 | 3.0 | 4.2 | 2.1 |
| 110-81-17 | A15 | nd | nd | 1.5 | nd | nd | nd | nd | nd | nd | 1.0 | 1.9 | 6.3 | 2.4 | 2.3 |
| 14-947-104 | A16 | 0.5 | nd | 1.1 | 6.1 | 1.5 | 1.3 | 6.1 | 1.1 | 1.1 | 1.6 | 1.4 | 69.0 | 4.7 | 1.2 |
| C11-3 | C11-3 | 0.6 | 4.7 | nd | nd | 1.1 | 2.1 | 1.0 | nd | 0.9 | 2.0 | 1.1 | 11.1 | 4.6 | 3.6 |
| C11-7 | C11-7 | 1.2 | 3.9 | nd | nd | 1.1 | 0.8 | 3.6 | nd | 1.3 | 2.5 | 1.8 | 6.2 | 3.4 | 2.0 |
| C11-10 | C11-10 | 0.6 | 6.8 | nd | nd | 0.9 | 1.4 | 1.1 | nd | 1.0 | 8.2 | 1.9 | 4.3 | 4.6 | 2.8 |
| C11-14 | C11-14 | 0.8 | 2.0 | 1.5 | nd | 0.8 | 1.1 | 13.4 | nd | 1.7 | 7.9 | 0.9 | 208.0 | 2.2 | 14.4 |
| C11-15 | C11-15 | 1.6 | 4.6 | nd | nd | 1.2 | 1.4 | 1.3 | nd | 1.5 | 5.1 | 1.5 | 4.9 | 3.8 | 5.7 |

EXAMPLE VIII

HCV Core Antigen Assay Sample Diluent Buffer

The HCV core antigen assay for PRISM®, as described in Example XI, utilizes a sample diluent buffer (SDB) for dilution of the human serum or plasma sample to be tested. The monoclonal antibody-coated microparticles are then added to form a reaction mixture. It is possible that the sensitivity and specificity of the antigen detection assay is affected by the composition of the SDB, in terms of the ingredients and their concentration.

It was hypothesized that, since HCV is believed to be an enveloped virus, it would be necessary to include detergent (surfactant) in the SDB to remove the lipid envelope, thereby exposing the core protein to solution. In addition, it was surmised that addition of chaotropic salts to the SDB might aid in dissolution of the nucleocapsid complex which could enhance detectability of core antigen.

To investigate the possible effects of SDB composition on the HCV core antigen assay sensitivity, a series of buffers was prepared and tested in an HCV core antigen assay comprised of monoclonal antibody C11-7 or C11-14 coated microparticles (as stated in the table legends) and acridinium labeled monoclonal antibody C11-10 conjugate. The simplest SDB used (also referred to as basal buffer), in terms of number of components, consisted of 0.1 M potassium phosphate, pH 7.2, 10 mM EDTA. This is the buffer to which detergents and salts were added. The performance of the SDBs was determined by examining their effect on the 0.09–0.15% solids and C11-10 conjugate at a working concentration of 100–125 ng/ml. For all experiments, the same positive and negative control plasma was used (0.1 ml for each assay). Assays were performed using the instrumentation and operation methods as described in Example VIII.

As shown in Table VIII, the S/N value obtained varies greatly depending upon the detergent added to the sample diluent buffer and its concentration. Addition of the zwitterionic surfactant SB-12 (lauryl sulfobetaine) gave the highest S/N values. In addition, as shown in Table IX, the highest S/N values were again seen with SB-12 when compared to other zwitterionic detergents of the same class but with different alkyl chain lengths. Titration of the amount of SB-12 added to the basal buffer in the presence of 0.5% or 2% Triton X-100 is shown in Table X. Increasing the SB-12 concentration over 6% diminished S/N values obtained in the core antigen assay significantly.

Further experiments examined the effect of the addition of salts or different combinations of zwitterionic or nonionic detergents to the sensitivity of the core antigen assay. Results presented in Tables XI and XII suggest a marginal effect on S/N is observed when KCl is substituted for NaCl, the same is true for the addition of urea. The sample diluent buffers containing SB-16 (palmityl sulfobetaine) appear to exhibit enhanced S/N values. The effect of urea was examined by including increasing concentrations in one of the SDBs that gave reasonably high S/N values compared to the others in a previous experiment (Table XIII). In this particular buffer, addition of urea to a final concentration of 2.0–2.5 M appears to have increased S/N values most significantly.

The effect on S/N values by the addition of various proteins or serum from nonhuman sources to a sample diluent buffer was also examined (Table XIV). The inclusion of bovine serum albumin, with or without other proteinacious components, only marginally increased the S/N values obtained upon testing of the HCV positive control serum. In contrast, some combinations of protein or sera actually decreased the S/N value relative to that observed for the protein-free buffer.

TABLE VIII

Effect of Detergent on HCV Core Antigen Detection

| Detergent/Additive (in basal buffer) | Acronym | S/N @ 0.5% | S/N @ 2% |
|---|---|---|---|
| Dodecyldimethyl-3-amonio-propane sulfonate | SB-12 | 2.4 | 7.9 |
| 1-dodecylpyridinium chloride | DPC | 0.1 | 6.9 |
| Sodium dodecylsulfate | SDS | 2.7 | 5.0 |
| Cholamidopropyldimethylamonio propanesulfonate | CHAPS | 1.0 | 4.7 |
| 3a, 7a, 12a-Trihydroxy-5b-cholanic acid | Cholate | 1.2 | 2.2 |
| t-Octylphenoxypolyethoxyethanol | Triton X-100 | 2.0 | 1.8 |
| Carboxymethyltrimethylammonium | Betaine | 1.9 | 1.5 |
| Taurocholic acid | TCA | 1.1 | 1.3 |
| Dodecyltrimethylammonium bromide | DTAB | 0.2 | 1.1 |
| Mixture of steroids, polysacc., detergents | Saponin | 3.1 | 0.9 |
| N-Dodecanoyl-N-methylglycine (N-lauroyl sarcosine) | NLS | 1.6 | 0.2 |
| Cetyltrimethylammonium bromide | CTAB | 1.6 | nd |
| Tetradecyltrimethylammonium bromide | TDTAB | 1.6 | nd |

Assay format: Anti-HCV core monoclonal C11-7 coated microparticles (0.40 um) and C11-10 conjugate.
nd: not determined.

TABLE IX

| Detergent/Additive (in basal buffer) | Acronym | S/N @ 0.5% | S/N @ 2% |
|---|---|---|---|
| (3-[(3-cholamidopropyl)dimethylammonio]-2-hydroxy-1-propanesulfonate | CHAPSO | 2.9 | 11.5 |
| N-dodecyl-N,N-(dimethylammonio)butyrate | DDMAB | 1.9 | nd |
| N-dodecyl-N,N-(dimethylammonio)undecanoate | DDMAU | 4.1 | 9.4 |
| N,N-dimethyldodecylamine-N-oxide | LDAO | 3.8 | 1.8 |
| N-octyl-N,N-dimethyl-3-ammonio-1-propanesulfonate | SB-8 | 2.5 | 3.8 |
| N-decyl-N,N-dimethyl-3-ammonio-1-propanesulfonate | SB-10 | 3.0 | 5.2 |
| N-dodecyl-N,N-dimethyl-3-ammonio-1-propanesulfonate | SB-12 | 16.0 | 38.3 |
| N-tetradecyl-N,N-dimethyl-3-ammonio-1-propanesulfonate | SB-14 | 4.5 | 0.8 |
| N-hexadecyl-N,N-dimethyl-3-ammonio-1-propanesulfonate | SB-16, 0.125% | 5.0 | nd |

Assay format: Anti-HCV core monoclonal C11-14 coated microparticles (0.40 um) and C11-10 conjugate.
nd: not determined.

TABLE X

| Detergent/Additive (in basal buffer) | S/N with 0.5% Triton X100 | S/N with 2% Triton X100 |
|---|---|---|
| 2% SB-12 | 13.3 | 14.8 |
| 4% SB-12 | 14.3 | 16.6 |
| 6% SB-12 | 10.7 | 15.3 |
| 8% SB-12 | 0.8 | 0.91 |

Assay format: Anti-HCV core monoclonal C11-14 coated microparticles (0.40 um) and C11-10 conjugate.

TABLE XI

SDB Components and Final Concentration

| NaCl | SB-12 | SB-16 | CTAB | Triton X-100 | Urea | Exp 1 S/N | Exp 2 S/N |
|---|---|---|---|---|---|---|---|
| (no buffer added) | | | | | | 3.85 | nd |
| Water | | | | | | 3.41 | 4.7 |
| 0.5 M | | | | | | 2.84 | 6.7 |
| 0.5 M | | | | 1.80% | | 32.17 | 34.2 |
| 0.5 M | 2% | | | | | 93.4 | 78.2 |

TABLE XI-continued

SDB Components and Final Concentration

| NaCl | SB-12 | SB-16 | CTAB | Triton X-100 | Urea | Exp 1 S/N | Exp 2 S/N |
|---|---|---|---|---|---|---|---|
| 0.5 M | 2% | | | | 2.5 M | 106.3 | 82.9 |
| 0.5 M | 2% | | 0.10% | | | 97.1 | 67.4 |
| 0.5 M | 2% | | 0.10% | | 2.5 M | 93.9 | 86.3 |
| 0.5 M | 2% | | 0.10% | 1.80% | | 98.8 | 79.1 |
| 0.5 M | 2% | | 0.10% | 1.80% | 2.5 M | 84.8 | 90.5 |
| 0.5 M | | 2% | | | 2.5 M | 105.2 | 92.9 |
| 0.5 M | | 2% | 0.10% | | | 106.8 | 108.1 |
| 0.5 M | | 2% | 0.10% | | 2.5 M | 142.2 | 102.3 |
| 0.5 M | | 2% | 0.10% | 1.80% | | 115.1 | 101.6 |
| 0.5 M | | 2% | 0.10% | 1.80% | 2.5 M | nd | 103.0 |

All SDBs were prepared in basal buffer containing 0.1 M potassium phosphate, pH 7.2, 10 mM EDTA. Assay format: Anti-HCV core monoclonal C11-14 coated microparticles (0.227 um) and C11-10 conjugate.

TABLE XII

SDB Components and Final Concentration

| KCl | SB-12 | SB-16 | CTAB | Triton X-100 | Urea | S/N |
|---|---|---|---|---|---|---|
| 0.5 M | 2% | | | | | 48.6 |
| 0.5 M | 2% | | | | 2.5 M | 86.8 |
| 0.5 M | 2% | | 0.10% | | | 52.8 |
| 0.5 M | 2% | | 0.10% | | 2.5 M | 77.6 |
| 0.5 M | 2% | | 0.10% | 1.80% | | 83.6 |
| 0.5 M | 2% | | 0.10% | 1.80% | 2.5 M | 106.8 |
| 0.5 M | | 2% | | | 2.5 M | 122.6 |
| 0.5 M | | 2% | 0.10% | | 2.5 M | 136 |
| 0.5 M | | 2% | 0.10% | 1.80% | | 127.9 |
| 0.5 M | | 2% | 0.10% | 1.80% | 2.5 M | 113.7 |

All SDBs were prepared in basal buffer containing 0.1 M potassium phosphate, pH 7.2, 10 mM EDTA. Assay format: Anti-HCV core monoclonal C11-14 coated microparticles (0.227 um) and C11-10 conjugate.

TABLE XIII

Effect of Urea on Antigen Assay Sensitivity

| HCV positive | S/N values at various urea concentrations | | | | | | | |
|---|---|---|---|---|---|---|---|---|
| control plasma dilution factor | 0.0 M | 0.5 M | 1.0 M | 1.5 M | 2.0 M | 2.5 M | 3.0 M | 5.0 M |
| 1:2 | 35.2 | 31.3 | 32.9 | 33.4 | 43.0 | 34.6 | 33.2 | 1.1 |
| 1:4 | 19.9 | 15.7 | 17.7 | 13.6 | 21.5 | 18.9 | 15.6 | 1.1 |
| 1:8 | 9.1 | 8.2 | 9.3 | 6.1 | 10.5 | 8.1 | 8.0 | 0.9 |
| 1:16 | 5.9 | 4.3 | 5.7 | 5.3 | 6.6 | 5.6 | 5.5 | 1.0 |
| 1:32 | 3.8 | 3.2 | 3.6 | 3.3 | 3.6 | 3.5 | 3.0 | 1.0 |

Urea was added to increasing final concentrations in the following buffer: 0.1 M potassium phosphate, pH 7.2, 10 mM EDTA, 0.5 M Nacl, 2.0% SB-16, 0.10 CTAB, 1.8% Triton X-100. HCV positive control plasma was diluted in negtive control plasma. Assay format: Anti-HCV core monoclonal C11-14 coated microparticles (0.227 um) and C11-10 conjugate.

TABLE XIV

Effect of Protein or Serum on Antigen Assay Sensitivity

| Component(s) Added (final conc., w/v)y | S/N PC 1:2 | S/N PC 1:16 |
|---|---|---|
| No additions | 69.3 | 9.6 |
| 1% BSA, 2% mouse serum | 73.7 | 10.3 |
| 1% BSA, 0.1% casein | 70.5 | 10.7 |
| 1% BSA | 70.2 | 10.3 |
| 3% horse serum | 68.2 | 9.6 |
| 2% mouse serum | 65.6 | 10.9 |
| 0.1% casein | 51.7 | 8.1 |
| 2% mouse serum, 0.1% casein | 50.9 | 7.9 |
| 1% BSA, 3% horse serum | 50.6 | 8.8 |
| 0.1% casein, 3% horse serum | 40.7 | 6.9 |
| 2% mouse serum, 3% horse serum | 34.3 | 4.9 |

Protein or sera were added to buffer containing 100 mM potassium phosphate, pH 7.2, 10 mM EDTA, 0.5 M NaCl, 2% SB16, 1.10% CTAB, 1.8% Triton X-100, 2.5 M urea. Positive control plasma (PC) was diluted 1:2 or 1:16 in negative control plasma.

EXAMPLE IX

PRISM® HCV Ab, PRISM® HCV Ag, and PRISM® HCV Ab/Ag Combo Assays

The PRISM® antibody assay is described in U.S. Pat. No. 5,705,330, incorporated herein by reference and the PRISM® antigen and antibody assays are described in Shah and Stewart, *The Immunoassay Handbook*, second edition, edited by David Wild, p 297–303 (2001), also incorporated herein by reference.

With respect to the present invention, the following procedures were utilized:

HCV Ab Assay:

Assay format is provided in FIG. 1.

Generally, at station 1, 50 μl of control or sample, 50 μl of specimen diluent buffer (SDB, Phosphate buffer, pH 7.0 containing Tween 20, newborn calf serum, NaCl, superoxide dismutase (SOD), *E. coli* lysate and azide), and 50 μl of HCV antigen coated microparticles (prepared as described in Example (V) (A1) (iv) above) were dispensed into each incubation well and assay timing was started. These were mixed by mutual diffusion of each into the other without external agitation or shaking to form a reaction mixture. At station 4, the reaction mixture was transferred to a detection well which contained a fibrous matrix and washed twice with 300 μl of transfer wash (TW, containing borate buffer, pH 7.0, with NaCl, Tween-20, Glycerol and Proclin 300). After 18 minutes of incubation at room temperature, 50 μl of a pre-complexed biotinylated F(ab')$_2$/acridinium labeled anti-biotin, (biotinylated F(ab')$_2$ fragment of goat anti-human IgG and acridinium labeled anti-biotin antibody), was dispensed into the matrix of the detection well at station 5. The well was incubated for 23 minutes at 37° C., and the fibrous matrix containing the reaction mixture was washed three times with 100 μl of FW, containing MES (2-[N-morpholino] ethanesulfonic acid), pH 5.7, with NaCl and Proclin 300 at station 8. At station 9, as in all of the assays described below, a chemiluminescence (CL) signal was generated by addition of an alkaline hydrogen peroxide solution, and the photons were measured by a photo multiplier tube. The amount of light emitted is proportional to the amount of antibody in the sample. The presence or absence of antibody in the sample is determined by comparing the number of photons collected from the sample to a cutoff (S/CO) value determined from a calibration performed in the batch. The results are expressed as S/CO (signal to cutoff) in Table XV below. The cutoff value is calculated by the sum of product of the average chemiluminescence counts of the positive control (n=4) times 0.55 plus the average chemiluminescence counts of the negative control (n=4).

Sensitivity: The seroconversion sensitivity was 100% as compared to the HCV RNA data provided in vendor certificate of analysis data for the selected seroconversion panels tested. Data is summarized in Table XV.

Specificity: Based on repeat reactive rates, the specificity of the HCV Ab assay was >99% with the population tested (Table XVII).

Figure 2:
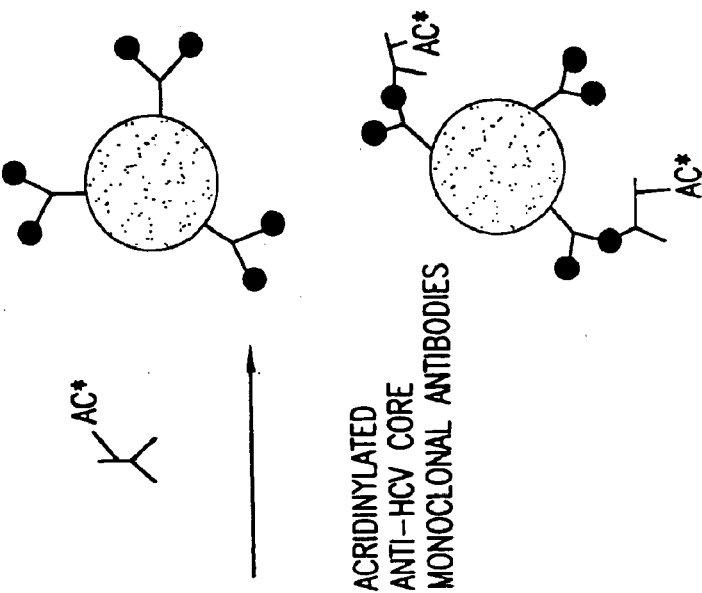
FIG. 2 illustrates the HCV Ag assay format. This assay also uses a 2-step format. When microparticles coated with HCV Mab (e.g., c11-14) are combined with the donor specimen, a diluent and acridinium-labeled Mab (e.g., acridinium labeled c11-10), an amount of photons representing a qualitative measurement of anti-HCV antigens in the specimen will result. The measured amount of photons indicates the amount of HCV antigens in the specimen when triggered with the PRISM® Activator solution.
Figure 2:
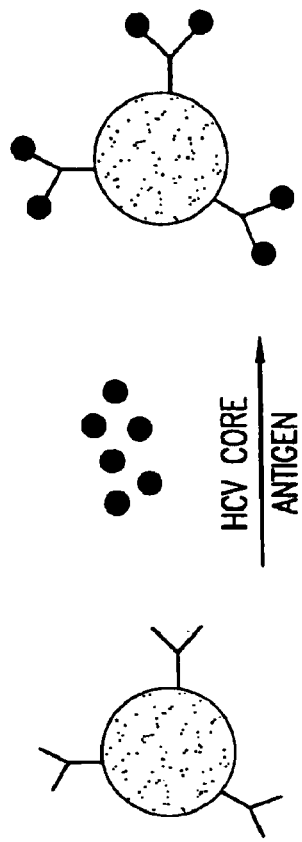
Figure 2:
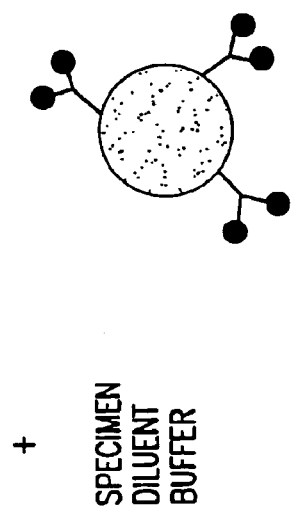

HCV Ag Assay:

Assay format is provided in FIG. 2.

Mab C11-14/Mab C11-10 Pair:

Generally, at station 1, 100 µl of control or sample, 50 µl of specimen diluent buffer (SDB, Sodium phosphate, EDTA, Triton X-100, Urea and sodium azide), and 50 µl of HCV Mab coated microparticles (prepared as described in Example (V) (B1) (i)) were dispensed into each incubation well and the assay timing was started. These were mixed by mutual diffusion of each into the other without external agitation or shaking to form a reaction mixture. At station 4, the reaction mixture was transferred to a detection well which contained a fibrous matrix and washed twice with 300 µl of transfer wash (TW) (MES, NaCl, Triton X-100, PEG, Antifoam, Proclin 300, pH 5.6) after 18 minutes of incubation at room temperature. At station 5, 50 µl of acridinylated C11-10 Mab conjugate (as mentioned in Example (VI) (B)) was dispensed into the matrix of the detection well. The contents of the well were incubated for 23 minutes, and the fibrous matrix containing the reaction mixture was washed one time with 200 µl of final wash (FW) (Tris buffer with LiCl and LDS) followed by three times with 100 ul of FW. The CL signal was triggered and measured at station 9. The results are expressed as S/CO (signal to cutoff) in Table XV. The cutoff value is 2.2 times the average chemiluminescence count of the negative control (n=5).

Sensitivity: Two groups of commercially available seroconversion panels containing serially collected samples from individuals who developed antibodies to HCV were tested in the prototype PRISM® HCV antigen test and in the PRISM® HCV antibody test. For the first group of seroconversion samples, the first available bleed date was negative for HCV RNA. In subsequent bleed dates, HCV RNA was detected for one or more bleed dates, followed in all cases by detection of antibodies to HCV. For the second group of seroconversion panels, the first bleed date was already positive for HCV RNA; antibodies to HCV were detected in subsequent bleed dates. For the two groups seroconversion sensitivity was 98.5% as compared to data obtained by HCV RNA testing. The PRISM® HCV Ag detected 67/68 HCV RNA positive bleeds as reactive. Data is summarized in Table XVI. These data indicate that HCV Ag testing detects HCV infection in individuals who have not yet mounted an antibody response.

Specificity: Based on repeat reactive rates, the specificity of the HCV Ag assay was >99% with the population tested (Table XVIII).

HCV Ag Assay: Mab A5 (14-635-225)/Mab C11-10 Pair:

An assay procedure, similar to that mentioned for C11-14/C11-10, was used. The only difference was that the test used Abbott A5 (14-635-225) Mab coated microparticles instead of Mab C11-14 coated microparticles.

Sensitivity: A total of 4 seroconversion panels were evaluated and sensitivity was compared with the data generated using C11-14/C11-10 pair. Both these pairs detected the same number of positive bleeds. Sensitivity data for A5 (14-635-225)/C11-10 pair is summarized in Table XVI.

Specificity: Based on repeat reactive rates, the specificity of the HCV Ag assay was 100% with the mini population (n=100) tested (Table XIX).

HCV Ag Assay: Mab C11-14 and C11-3/Mab C11-10 Pair:

An assay procedure, similar to that mentioned for C11-14/C11-10, was used. The only difference was the use of C11-14 and C11-3 blended microparticles (Example (IV) (B1) (iv)) instead of Mab C11-14 coated microparticles.

Sensitivity: The performance of this pair was assessed by comparing the S/N ratio against panels consisting of recalcified human plasma positive for HCV Core antigen (termed "PC") and a human plasma negative for HCV antigens and antibodies (termed "NC") (Table XX). The S/N was determined by the formula:

$S/N$=Average of $PC$/Average of $NC$

The average chemiluminescence counts of four specimens were used to determine each average.

PRISM® HCV Ag/Ab Combo Assay:

Two different formats (i.e., Dual Combo assay and Real combo assay) were evaluated on the PRISM® HCV Ag/Ab Assay as follows:

Dual Combo Assay: The HCV Ag/Ab dual combo assay is run simultaneously on PRISM® using two different channels. A total of six channels in PRISM® are used simultaneously to run several assays (HIV, HBcore, HBsAg, HTLV, and HCVAb) five of which are currently in use, while one channel remains open for new markers (e.g. HCV Ag assay) or can be reserved in case one of the channels become problematic. Thus, by using one channel for an HCV Ag assay and five other channels for five other assays, a reserve channel is not available for use.

The PRISM® HCV Ab and PRISM® HCV Ag assays were performed individually. The results from both assays were combined to produce a single, final report.

Real Combo Assay: The PRISM® HCV Ag and HCV Ab assays were combined and performed as a single assay in one of the PRISM® channels.

PRISM® HCV Ag/Ab Dual Combo Assay:

Sensitivity: The seroconversion sensitivity of the HCV Ab/Ag Dual Combo assay was 98.5%. Data is summarized in Table XV.

Specificity: Based on repeat reactive rates, the specificity of the HCV Ab/Ag Dual Combo assay was >99% with the population tested (Table XXI).

Figure 3:
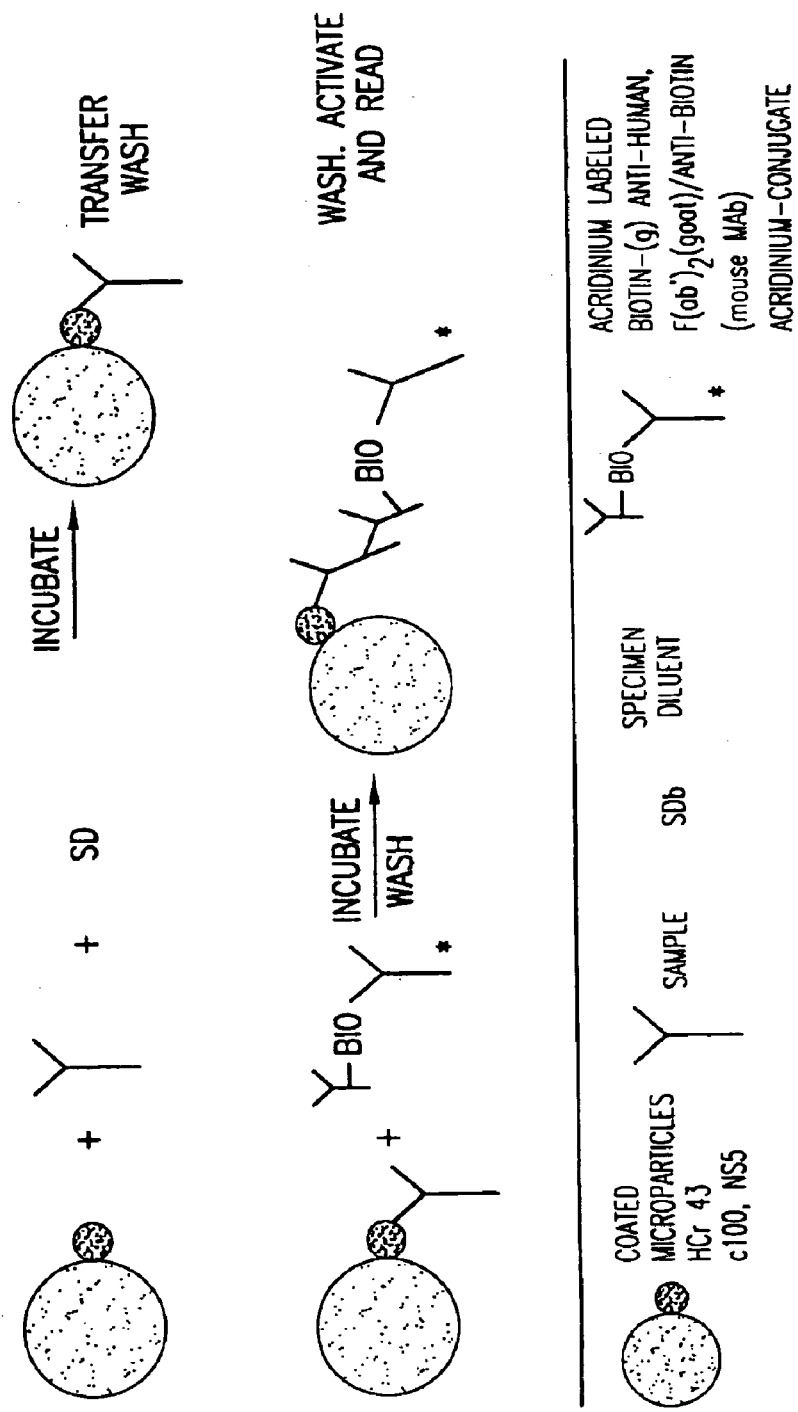
FIG. 3 illustrates the HCV Ag/Ab combo assay format. The assay uses a 2-step format. When HCV recombinant antigen and monoclonal antibody blended microparticles (e.g., HCV peptide from the core, and recombinant antigens from the NS3, NS4 and NS5 regions of the HCV genome blended with microparticles coated with c11-14) are combined with the donor specimen, a diluent and blended Acridinium-labeled Mabs (e.g., acridinium labeled c11-10 and acridinylated mouse-anti-human IgG), an amount of photons representing a qualitative measurement of anti-HCV antigens or anti-HCV antibodies or both in the specimen will result when triggered with PRISM® Activator solution.

PRISM® HCV Ag/Ab Real Combo Assay:

Assay format is provided in FIG. 3. The 2 step PRISM® HCV Combo assay was performed as mentioned above for the HCV Ab or Ag assay with the following changes: At station 1, 100 µl of control or sample, 50 µl of specimen diluent buffer (Phosphate buffer, pH 7.0 containing Tween 20, newborn calf serum, NaCl, Tween-20, superoxide dismutase (SOD), E. coli lysate and azide), and 50 µl of HCV antigen and Mab blended microparticles (prepared as described in Example (V) (C) (i) above) were dispensed into each incubation well and the assay timing was started. At station 4, the reaction mixture was transferred to a detection well which contained a fibrous matrix and washed twice with 300 ul of transfer wash (MES, NaCl, Triton X-100, PEG, Antifoam, Proclin 300, pH 5.6). After 18 minutes of incubation at 37 degree C., 50 ul of blended conjugate acridinylated C11-10 and Acridinylated Mouse anti-Human IgG (prepared as described in Example (VI) (C)) was dispensed into the matrix of the detection well at station # 5. The well was incubated for 23 minutes, and the fibrous matrix containing the reaction mixture was washed three times with 100 µl of final wash (Tris buffer with LiCl and LDS). The CL signal was triggered and measured at station 9. The results are expressed as S/CO (signal to cutoff) in Table XV below. The cutoff value is 2.2 times the average chemiluminescence count of the negative control (n=3).

Sensitivity: The seroconversion sensitivity was 95.8% as compared to PCR data. The PRISM® HCV Ag/Ab Real Combo assay detected 23/24 positive bleeds as reactive. Data is summarized in Table XVI.
Specificity: Based on repeat reactive rates the specificity of HCV Ag/Ab Real Combo assay was 100% with the population tested (Table XX):

TABLE XV

| Genotype | Ag earlier than Ab by | Day Number | HCV RNA Test Results | HCV Ab S/CO | HCV Ag S/CO | HCV Ab/Ag Dual Combo S/CO |
|---|---|---|---|---|---|---|
| 1a | 38 Days | 0 | − | 0.09 | 0.49 | NEG |
| | | 24 | + | 0.11 | 10.63 | POS |
| | | 27 | + | 0.10 | 43.77 | POS |
| | | 31 | + | 0.11 | 72.92 | POS |
| | | 62 | + | 5.19 | 44.41 | POS |
| | | 64 | + | 5.22 | 69.55 | POS |
| | | 69 | + | 5.91 | 12.92 | POS |
| | | 71 | + | 6.29 | 7.09 | POS |
| 1a | 20 Days | 0 | + | 0.10 | 107.78 | POS |
| | | 3 | + | 0.11 | 97.81 | POS |
| | | 10 | + | 0.15 | 63.52 | POS |
| | | 20 | + | 1.57 | Not Tested | POS |
| 1b | 18 Days | 0 | + | 0.09 | 76.61 | POS |
| | | 4 | + | 0.09 | 56.09 | POS |
| | | 7 | + | 0.08 | 39.63 | POS |
| | | 13 | + | 0.34 | 32.14 | POS |
| | | 18 | + | 1.53 | 14.93 | POS |
| | | 21 | + | 3.20 | 19.97 | POS |
| | | 164 | Not Tested | 5.86 | 0.61 | POS |
| 2b | 14 Days | 0 | + | 0.10 | 8.41 | POS |
| | | 2 | + | 0.40 | 23.62 | POS |
| | | 7 | + | 2.62 | 14.09 | POS |
| | | 9 | + | 3.09 | 16.67 | POS |
| | | 14 | + | 3.99 | 4.74 | POS |
| 1a | 42 Days | 0 | − | 0.09 | 0.76 | NEG |
| | | 2 | − | 0.08 | 0.47 | NEG |
| | | 7 | − | 0.09 | 0.41 | NEG |
| | | 9 | − | 0.09 | 0.40 | NEG |
| | | 15 | − | 0.08 | 0.42 | NEG |
| | | 17 | − | 0.08 | 0.49 | NEG |
| | | 22 | − | 0.07 | 0.49 | NEG |
| | | 24 | − | 0.08 | 0.45 | NEG |
| | | 29 | − | 0.09 | 0.52 | NEG |
| | | 31 | − | 0.08 | 0.51 | NEG |
| | | 36 | − | 0.08 | 0.57 | NEG |
| | | 38 | − | 0.09 | 0.51 | NEG |
| | | 43 | − | 0.08 | 0.52 | NEG |
| | | 45 | − | 0.09 | 0.43 | NEG |
| | | 50 | − | 0.09 | 0.69 | NEG |
| | | 52 | − | 0.08 | 0.52 | NEG |
| | | 57 | − | 0.09 | 0.49 | NEG |
| | | 64 | − | 0.09 | 0.90 | NEG |
| | | 67 | − | 0.08 | 0.52 | NEG |
| | | 74 | − | 0.09 | 0.51 | NEG |
| | | 79 | − | 0.08 | 0.52 | NEG |
| | | 84 | − | 0.09 | 0.40 | NEG |
| | | 105 | − | 0.09 | 0.45 | NEG |
| | | 108 | − | 0.08 | 0.66 | NEG |
| | | 112 | − | 0.09 | 0.57 | NEG |
| | | 119 | − | 0.09 | 0.45 | NEG |
| | | 121 | − | 0.09 | 0.42 | NEG |
| | | 140 | + | 0.12 | 10.65 | POS |
| | | 143 | + | 0.09 | 3.81 | POS |
| | | 147 | + | 0.10 | 9.30 | POS |
| | | 150 | + | 0.09 | 34.08 | POS |
| | | 154 | + | 0.09 | 58.01 | POS |
| | | 157 | + | 0.09 | 80.90 | POS |
| | | 161 | + | 0.08 | 107.11 | POS |
| | | 164 | + | 0.09 | 114.41 | POS |
| | | 168 | + | 0.09 | 93.29 | POS |
| | | 171 | + | 0.10 | 89.06 | POS |
| | | 182 | + | 1.83 | 63.62 | POS |
| | | 186 | + | 4.39 | 68.72 | POS |
| | | 189 | + | 5.20 | 119.62 | POS |
| 1a | 21 Days | 0 | + | 0.08 | 63.86 | POS |
| | | 4 | + | 0.07 | 50.76 | POS |
| | | 17 | + | 0.09 | 73.66 | POS |

TABLE XV-continued

| | | | | | |
|---|---|---|---|---|---|
| | | 21 | + | 1.02 | 45.58 | POS |
| | | 25 | + | 4.03 | 60.94 | POS |
| | | 29 | + | 5.08 | 47.38 | POS |
| 1a | 37 Days | 0 | + | 0.08 | 33.66 | POS |
| | | 2 | + | 0.06 | 30.83 | POS |
| | | 7 | + | 0.08 | 30.10 | POS |
| | | 9 | + | 0.07 | 39.66 | POS |
| | | 26 | + | 0.07 | 25.51 | POS |
| | | 32 | + | 0.12 | 15.29 | POS |
| | | 37 | + | 2.43 | 15.51 | POS |
| | | 41 | + | 3.36 | 3.10 | POS |
| 1a | 28 Days | 0 | + | 0.09 | 67.75 | POS |
| | | 2 | + | 0.09 | 87.93 | POS |
| | | 10 | + | 0.10 | 36.53 | POS |
| | | 12 | + | 0.10 | 60.67 | POS |
| | | 19 | + | 0.10 | 39.62 | POS |
| | | 21 | + | 0.11 | 26.25 | POS |
| | | 28 | + | 2.78 | 9.94 | POS |
| | | 30 | + | 4.00 | 17.02 | POS |
| | | 35 | + | 4.71 | 15.26 | POS |
| | | 37 | Not tested | 4.84 | 13.02 | POS |
| 1a | 25 Days | 0 | + | 0.15 | 4.73 | POS |
| | | 2 | + | 0.40 | 6.63 | POS |
| | | 8 | + | 0.16 | 7.48 | POS |
| | | 10 | + | 0.11 | 5.20 | POS |
| | | 16 | + | 0.17 | 7.60 | POS |
| | | 18 | + | 0.11 | 7.58 | POS |
| | | 23 | + | 0.64 | 8.66 | POS |
| | | 25 | + | 2.11 | 9.58 | POS |
| | | 30 | + | 2.76 | 6.21 | POS |
| | | 32 | + | 3.39 | 7.84 | POS |
| | | 49 | + | 6.12 | 1.83 | POS |
| | | 53 | + | 6.13 | 1.93 | POS |
| | | 56 | + | 6.34 | 1.63 | POS |
| 1a | 28 Days | 0 | − | 0.13 | 1.27 | POS |
| | | 2 | − | 0.23 | 0.52 | NEG |
| | | 8 | − | 0.09 | 0.50 | NEG |
| | | 11 | + | 0.10 | 0.54 | NEG |
| | | 15 | + | 0.10 | 1.92 | POS |
| | | 18 | + | 0.11 | 1.90 | POS |
| | | 28 | + | 0.12 | 2.42 | POS |
| | | 30 | + | 0.10 | 7.04 | POS |
| | | 35 | + | 0.14 | 6.01 | POS |
| | | 37 | + | 0.98 | 13.68 | POS |
| | | 43 | + | 4.74 | 10.07 | POS |
| | | 46 | + | 5.27 | 4.91 | POS |
| 1a | 13 Days | 0 | + | 0.10 | 1.82 | POS |
| | | 3 | + | 0.10 | 1.72 | POS |
| | | 5 | + | 0.15 | 1.35 | POS |
| | | 11 | + | 0.97 | 1.70 | POS |
| | | 13 | + | 1.26 | 3.63 | POS |
| | | 19 | − | 3.70 | 2.94 | POS |
| | | 25 | − | 4.89 | 2.43 | POS |
| | | 27 | − | 5.20 | 1.61 | POS |
| | | 32 | − | 5.61 | 1.35 | POS |
| | | 35 | − | 5.86 | 1.30 | POS |
| | | 41 | − | 6.11 | 0.88 | POS |
| | | 45 | − | 5.69 | 0.67 | POS |
| | | 48 | − | 5.95 | 1.94 | POS |
| 1a | 23 Days | 0 | − | 0.09 | 0.45 | NEG |
| | | 2 | − | 0.08 | 0.45 | NEG |
| | | 17 | + | 0.07 | 20.06 | POS |
| | | 19 | + | 0.09 | 45.84 | POS |
| | | 24 | + | 0.09 | 81.03 | POS |
| | | 26 | + | 0.07 | 63.30 | POS |
| | | 36 | + | 0.31 | 74.78 | POS |
| | | 40 | + | 4.03 | 49.53 | POS |
| 1a | 33 Days | 0 | − | 0.09 | 0.54 | NEG |
| | | 3 | − | 0.08 | 0.50 | NEG |
| | | 7 | − | 0.08 | 0.58 | NEG |
| | | 12 | − | 0.09 | 0.54 | NEG |
| | | 14 | − | 0.09 | 0.56 | NEG |
| | | 19 | − | 0.10 | 0.53 | NEG |
| | | 25 | − | 0.10 | 0.51 | NEG |
| | | 28 | − | 0.09 | 0.50 | NEG |
| | | 32 | − | 0.09 | 0.50 | NEG |
| | | 35 | − | 0.10 | 0.35 | NEG |
| | | 39 | − | 0.09 | 0.53 | NEG |
| | | 45 | + | 0.10 | 9.43 | POS |

TABLE XV-continued

| | | | | | | |
|---|---|---|---|---|---|---|
| | | 47 | + | 0.11 | 42.00 | POS |
| | | 52 | + | 0.11 | 28.05 | POS |
| | | 56 | + | 0.11 | 25.63 | POS |
| | | 60 | + | 0.09 | 78.15 | POS |
| | | 73 | + | 0.18 | 9.54 | POS |
| | | 78 | + | 1.83 | 5.34 | POS |
| | | 80 | + | 2.13 | 3.40 | POS |
| 1a | 32 Days | 0 | − | 0.46 | 0.54 | NEG |
| | | 22 | − | 0.42 | 0.53 | NEG |
| | | 24 | − | 0.43 | 0.47 | NEG |
| | | 42 | + | 0.46 | 8.79 | POS |
| | | 46 | + | 0.44 | 22.26 | POS |
| | | 74 | + | 4.22 | 19.82 | POS |
| | | 76 | + | 4.50 | 23.78 | POS |
| 3a | 141 Days | 0 | + | 0.12 | 2.81 | POS |
| | | 4 | + | 0.49 | 1.95 | POS |
| | | 11 | + | 2.48 | 1.41 | POS |
| | | 13 | + | 2.54 | 1.41 | POS |
| | | 44 | + | 4.29 | 0.43 | POS |
| | | 46 | + | 4.68 | 0.43 | POS |

| Genotype | Ag earlier than Ab by | Day Number | HCV RNA Test Results | HCV Ab S/CO | HCV Ag S/CO | HCV Ab/Ag Real Combo S/CO |
|---|---|---|---|---|---|---|
| 1a | 38 Days | 0 | − | 0.09 | 0.49 | 0.38 |
| | | 24 | + | 0.11 | 10.63 | 1.60 |
| | | 27 | + | 0.10 | 43.77 | 5.32 |
| | | 31 | + | 0.11 | 72.92 | 11.04 |
| | | 62 | + | 5.19 | 44.41 | 10.95 |
| | | 64 | + | 5.22 | 69.55 | 10.16 |
| | | 69 | + | 5.91 | 12.92 | 4.51 |
| | | 71 | + | 6.29 | 7.09 | 3.68 |
| 1b | 18 Days | 0 | + | 0.09 | 76.61 | 14.09 |
| | | 4 | + | 0.09 | 56.09 | 5.59 |
| | | 7 | + | 0.08 | 39.63 | 4.75 |
| | | 13 | + | 0.34 | 32.14 | 3.81 |
| | | 18 | + | 1.53 | 14.93 | 4.16 |
| | | 21 | + | 3.20 | 19.97 | 3.81 |
| | | 164 | Not Tested | 5.86 | 0.61 | 2.72 |
| 1a | 23 Days | 0 | − | 0.09 | 0.45 | 0.31 |
| | | 2 | − | 0.08 | 0.45 | 0.48 |
| | | 17 | + | 0.07 | 20.06 | 1.36 |
| | | 19 | + | 0.09 | 45.84 | 2.72 |
| | | 24 | + | 0.09 | 81.03 | 4.57 |
| | | 26 | + | 0.07 | 63.30 | 4.15 |
| | | 36 | + | 0.31 | 74.78 | 6.90 |
| | | 40 | + | 4.03 | 49.53 | 5.11 |
| 1a | 32 Days | 0 | − | 0.46 | 0.54 | 0.48 |
| | | 22 | − | 0.42 | 0.53 | 0.31 |
| | | 24 | − | 0.43 | 0.47 | 0.32 |
| | | 42 | + | 0.46 | 8.79 | 0.99 |
| | | 46 | + | 0.44 | 22.26 | 2.11 |
| | | 74 | + | 4.22 | 19.82 | 3.99 |
| | | 76 | + | 4.50 | 23.78 | 3.27 |

* S/CO values ≥ 1.00 are considered reactive.

TABLE XVI

| Genotype | Ag earlier than Ab by | Day Number | HCV RNA Test Results | HCV Ab S/CO | HCV Ag c11-14/c11-10 S/CO | HCV Ag A5/c11-10 | HCV Ab/Ag Dual Combo S/CO |
|---|---|---|---|---|---|---|---|
| 1a | 38 Days | 0 | − | 0.09 | 0.49 | 0.53 | NEG |
| | | 24 | + | 0.11 | 10.63 | 6.47 | POS |
| | | 27 | + | 0.10 | 43.77 | 29.30 | POS |
| | | 31 | + | 0.11 | 72.92 | 64.97 | POS |
| | | 62 | + | 5.19 | 44.41 | 37.22 | POS |
| | | 64 | + | 5.22 | 69.55 | 39.55 | POS |
| | | 69 | + | 5.91 | 12.92 | 7.54 | POS |
| | | 71 | + | 6.29 | 7.09 | 4.42 | POS |
| 1b | 18 Days | 0 | + | 0.09 | 76.61 | 68.95 | POS |
| | | 4 | + | 0.09 | 56.09 | 48.69 | POS |
| | | 7 | + | 0.08 | 39.63 | 57.02 | POS |

TABLE XVI-continued

| Genotype | Ag earlier than Ab by | Day Number | HCV RNA Test Results | HCV Ab S/CO | HCV Ag c11-14/c11-10 S/CO | HCV Ag A5/c11-10 | HCV Ab/Ag Dual Combo S/CO |
|---|---|---|---|---|---|---|---|
| | | 13 | + | 0.34 | 32.14 | 34.85 | POS |
| | | 18 | + | 1.53 | 14.93 | 16.61 | POS |
| | | 21 | + | 3.20 | 19.97 | 13.78 | POS |
| | | 164 | Not Tested | 5.86 | 0.61 | 0.62 | NEG |
| 1a | 23 Days | 0 | − | 0.09 | 0.45 | 0.80 | NEG |
| | | 2 | − | 0.08 | 0.45 | 0.43 | NEG |
| | | 17 | + | 0.07 | 20.06 | 7.77 | POS |
| | | 19 | + | 0.09 | 45.84 | 17.28 | POS |
| | | 24 | + | 0.09 | 81.03 | 30.76 | POS |
| | | 26 | + | 0.07 | 63.30 | 27.95 | POS |
| | | 36 | + | 0.31 | 74.78 | 36.66 | POS |
| | | 40 | + | 4.03 | 49.53 | 21.78 | POS |
| 1a | 32 Days | 0 | − | 0.46 | 0.54 | 0.45 | NEG |
| | | 22 | − | 0.42 | 0.53 | 0.47 | NEG |
| | | 24 | − | 0.43 | 0.47 | 0.53 | NEG |
| | | 42 | + | 0.46 | 8.79 | 5.04 | POS |
| | | 46 | + | 0.44 | 22.26 | 14.18 | POS |
| | | 74 | + | 4.22 | 19.82 | 14.15 | POS |
| | | 76 | + | 4.50 | 23.78 | 8.54 | POS |

* S/CO values ≥ 1.00 are considered reactive.

TABLE XVII

| N Tested | 989* |
|---|---|
| RR | 9 |
| RRR | 0.91 |
| N negative | 980 |
| Mean S/CO Neg Pop | 0.12 |
| SD | 0.09 |
| SD to CO | 9.76 |

TABLE XVIII

| N Tested | 989* |
|---|---|
| RR | 1 |
| RRR | 0.10 |
| N negative | 988 |
| Mean S/CO Neg Pop | 0.44 |
| SD | 0.08 |
| SD to CO | 7.15 |

*Volunteer blood donors

TABLE XIX

| N Tested | 100* |
|---|---|
| RR | 0 |
| RRR | 0.00 |
| N negative | 100 |
| Mean S/CO Neg Pop | 0.56 |
| SD | 0.15 |
| SD to CO | 2.98 |

*Volunteer blood donor

TABLE XX

| | C11-10 conjugate: | | |
|---|---|---|---|
| Panel | C11-14 microparticle only | C11-3 microparticle only | C11-14 + C11-3 Blended microparticle |
| PC S/N | 213.7 | 87.8 | 179.4 |
| NC Counts | 78.8 | 90 | 93.25 |

TABLE XXI

| N Tested | 989* |
|---|---|
| RR | 9 |
| RRR | 0.91 |
| N negative | 980 |
| Mean S/CO Neg Pop | 0.12 |
| SD | 0.09 |
| SD to CO | 9.76 |

TABLE XXII

| N Tested | 92* |
|---|---|
| RR | 0 |
| RRR | 0 |
| N negative | 92 |
| Mean S/CO Neg Pop | 0.49 |
| SD | 0.15 |
| SD to CO | 3.4 |

*Volunteer blood donors

EXAMPLE X

Binding of Monoclonal Antibodies to Three Peptides

Three new peptides were synthesized, two of which are compatible with an HCV Ab/Ag combo format and one suitable for use as a control. Each peptide was synthesized with a N-terminal biotin for ease of tracking during preparation of the solid phase. Peptide aa 10-53 (ALAM-17) (KTKRNTNRRPQDVKFPGGGQIVGGVYLLPRRGPR LGVRATRKTS) (SEQ ID NO:37) contains HCV core amino acids 10–53 with no intervening deletions. Peptide aa 10-53^32-50 (ALAM-18) (KTKRNTNRRPQDVKFPGGGQIVKTS) (SEQ ID NO:38) contains HCV core amino acids 10–53 with a 19 amino acid deletion encompassing aa 32-50. Peptide aa 10-53^31-33^47-48 contains HCV core amino acids 10 through 53 where amino acids 31–33 and 47–48 were deleted (ALAM16) (KTKRNTNRRPQDVKFPGGGQIVYLLPRRGPRL GVTRKTS) (SEQ ID NO:35). Peptides ALAM-16 and ALAM-18 are both compatible with an HCV Ab/Ag combo format. In the case of ALAM-16, the deletion of amino acids 31–33 prevents monoclonal c11-10 (epitope 32-36) from binding to the antigen, and the deletion of amino acids 47 and 48 prevents binding of the c11-14 monoclonal (epitope 45-50). ALAM-18 contains a deletion that encompasses both the c11-10 and c11-14 binding regions. Data showing the lack of binding to ALAM-16 and ALAM-18 by monoclonals c11-10 and c11-14 are shown in the following table:

TABLE XXIII

| Monoclonal | Epitope (aa) | ALAM-17 Peptide aa 10-53 S/N | ALAM-18 Peptide aa 10-53^32-50 S/N | ALAM-16 Peptide aa 10-53 ^31-33^47-48 S/N |
|---|---|---|---|---|
| C11-15 | 19–27 | >125.0 | >200.0 | >153.8 |
| C11-10 | 32–36 | >125.0 | 0.9 | 0.4 |
| C11-14 | 45–50 | >125.0 | 0.4 | 0.4 |
| C11-3 | 104–110 | 1.0 | 0.4 | 0.4 |
| C11-7 | 112–124 | 0.9 | 0.5 | 0.4 |

*All monoclonals were run at a concentration of 1 ug/ml.

In addition, 254 HCV genotyped seropositive specimens, representing HCV genotypes 1, 2, 3, 4 and 6, were tested by peptide aa 10-53^31-33^47-48 (ALAM-16) to determine feasibility of this peptide as an antigenic target in an HCV Ab/Ag assay format. All 254 (100%) specimens were reactive toward this peptide. Thus, the deletions present in this peptide, which serve to eliminate binding by the monoclonals necessary for Ag detection, do not negatively impact reactivity of antibodies toward the remaining core epitopes.

---

What is claimed is:

1. A recombinant protein comprising the amino acid sequence of SEQ ID NO:32.

2. A recombinant protein comprising an amino acid sequence encoded by the nucleotide sequence of SEQ ID NO:31.

3. A vector or construct comprising the nucleotide sequence of SEQ ID NO:31.

4. An isolated host cell comprising said vector or construct of claim 3.

* * * * *